(12) United States Patent
Takatsuka et al.

(10) Patent No.: US 12,001,606 B2
(45) Date of Patent: Jun. 4, 2024

(54) CONTROL DEVICE COMPRISING DETECTION UNIT CONFIGURED TO PERFORM DETECTION OF BRAIN WAVE AND CONTROL METHOD THEREFOR

(71) Applicant: SONY GROUP CORPORATION, Tokyo (JP)

(72) Inventors: Susumu Takatsuka, Tokyo (JP); Hiroki Tetsukawa, Tokyo (JP); Itaru Shimizu, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 0 days.

(21) Appl. No.: 17/919,375

(22) PCT Filed: Apr. 9, 2021

(86) PCT No.: PCT/JP2021/014982
§ 371 (c)(1),
(2) Date: Oct. 17, 2022

(87) PCT Pub. No.: WO2021/215266
PCT Pub. Date: Oct. 28, 2021

(65) Prior Publication Data
US 2023/0161411 A1 May 25, 2023

(30) Foreign Application Priority Data
Apr. 23, 2020 (JP) ................................. 2020-076460

(51) Int. Cl.
*G06F 3/01* (2006.01)
*A61B 5/372* (2021.01)
(Continued)

(52) U.S. Cl.
CPC .............. *G06F 3/015* (2013.01); *G06F 3/012* (2013.01); *A61B 5/372* (2021.01); *A61B 5/397* (2021.01); *G06F 21/32* (2013.01)

(58) Field of Classification Search
CPC ..... A61B 5/395; A61B 5/378; A61B 5/14553; A61B 5/0075; A61B 5/117; A61B 5/6815;
(Continued)

(56) References Cited

U.S. PATENT DOCUMENTS

2014/0354534 A1* 12/2014 Mullins ................... G06F 3/015
345/156
2020/0201974 A1* 6/2020 Xiong ..................... G06F 21/31

FOREIGN PATENT DOCUMENTS

JP 2004-236682 A 8/2004
JP 2015-127851 A 7/2015
(Continued)

OTHER PUBLICATIONS

Hori, et al., "Context-based video retrieval system for the life-log applications", Proceedings of the 5th ACM SIGMM International Workshop on Multimedia Information Retrieval, MIR 2003, Berkeley, CA, USA, Nov. 7, 2003, pp. 31-38.
(Continued)

*Primary Examiner* — Deeprose Subedi
(74) *Attorney, Agent, or Firm* — CHIP LAW GROUP

(57) ABSTRACT

The present technology relates to a control device and a control method capable of providing a more convenient electroencephalogram input user interface.
Provided is a control device including a detection unit configured to perform detection of a brain wave included in a measured biometric signal of a user and detection of a user action based on information other than the brain wave included in the biometric signal, and a processing unit
(Continued)

configured to perform a predetermined process based on the brain wave in a case where the user action is a predetermined action. For example, the present technology can be applied to a measurement device capable of measuring a brain wave signal.

17 Claims, 39 Drawing Sheets

(51) Int. Cl.
*A61B 5/397* (2021.01)
*G06F 21/32* (2013.01)

(58) Field of Classification Search
CPC ... A61B 5/6898; A61B 5/4064; A61B 5/6803; A61B 5/372; A61B 2562/0233; A61B 5/38; A61B 5/397; A61B 2562/0209; A61B 2560/0406; A61B 5/381; G06F 3/016; G06F 3/015; G06F 3/012; G06F 21/32

See application file for complete search history.

(56) References Cited

FOREIGN PATENT DOCUMENTS

| JP | 2016-038904 A | 3/2016 |
| JP | 2018-190164 A | 11/2018 |
| JP | 2019-199177 A | 11/2019 |

OTHER PUBLICATIONS

International Search Report and Written Opinion of PCT Application No. PCT/JP2021/014982, dated May 25, 2021, 10 pages of ISRWO.

* cited by examiner

FIG. 17

| No | TRIGGER ACTION | TRIGGER ACTION SIGNAL |
|---|---|---|
| 1 | Trigger Action #1 (EYE CLOSING) | MYOELECTRIC SIGNAL #1 |
| 2 | Trigger Action #2 (BLINKING×2) | MYOELECTRIC SIGNAL #2 |
| 3 | Trigger Action #3 (NECK DOWN+BLINKING OF BOTH EYES×2→EYE CLOSING) | MYOELECTRIC SIGNAL #3, ACCELERATION SIGNAL #1, ANGULAR VELOCITY SIGNAL #1 |
| ⋮ | ⋮ | ⋮ |

231

FIG. 18

| No | TRIGGER ACTION | ELECTROENCEPHALOGRAM APPLICATION |
|---|---|---|
| 1 | Trigger Action #1 | ELECTROENCEPHALOGRAM PERSONAL AUTHENTICATION APPLICATION |
| 2 | Trigger Action #2 | ELECTROENCEPHALOGRAM SEARCH APPLICATION |
| ⋮ | ⋮ | ⋮ |

232

| No | ELECTROENCEPHALOGRAM APPLICATION | BRAIN WAVE SIGNAL |
|---|---|---|
| 1 | ELECTROENCEPHALOGRAM PERSONAL AUTHENTICATION APPLICATION | BRAIN WAVE SIGNAL #11 |
| | | BRAIN WAVE SIGNAL #12 |
| | | BRAIN WAVE SIGNAL #13 |
| | | ⋮ |
| 2 | ELECTROENCEPHALOGRAM SEARCH APPLICATION | BRAIN WAVE SIGNAL #21 |
| | | BRAIN WAVE SIGNAL #22 |
| | | BRAIN WAVE SIGNAL #23 |
| ⋮ | ⋮ | ⋮ |

| No | INDUCTION MEDIUM | BRAIN WAVE SIGNAL | TIME |
|---|---|---|---|
| 1 | INDUCTION SOUND #1 | BRAIN WAVE SIGNAL #31 | 2020/03/03 10:04:45 |
| 2 | INDUCTION SOUND #2 | BRAIN WAVE SIGNAL #32 | 2020/03/03 10:37:11 |
| 3 | INDUCTION SOUND #3 | BRAIN WAVE SIGNAL #33 | 2020/03/03 11:20:03 |
| 4 | INDUCTION SOUND #4 | BRAIN WAVE SIGNAL #34 | 2020/03/04 14:07:22 |
| 5 | INDUCTION SOUND #5 | BRAIN WAVE SIGNAL #35 | 2020/03/05 09:55:40 |
| 6 | INDUCTION SOUND #6 | BRAIN WAVE SIGNAL #36 | 2020/03/05 10:29:20 |
| ... | ... | ... | ... |

234

CONTROL DEVICE COMPRISING DETECTION UNIT CONFIGURED TO PERFORM DETECTION OF BRAIN WAVE AND CONTROL METHOD THEREFOR

CROSS REFERENCE TO RELATED APPLICATIONS

This application is a U.S. National Phase of International Patent Application No. PCT/JP2021/014982 filed on Apr. 9, 2021, which claims priority benefit of Japanese Patent Application No. JP 2020-076460 filed in the Japan Patent Office on Apr. 23, 2020. Each of the above-referenced applications is hereby incorporated herein by reference in its entirety.

TECHNICAL FIELD

The present technology relates to a control device and a control method, and more particularly to a control device and a control method capable of providing a more convenient electroencephalogram input user interface.

BACKGROUND ART

In recent years, research and development for analyzing brain waves and applying them to interfaces have been actively conducted.

For example, Patent Document 1 discloses a safe drive assistance system for determining whether a predetermined electroencephalogram pattern is detected in a brain wave measured by an electroencephalogram measurement unit in a case where it is determined whether a driver is in a drivable state by comparing allowable information about the driver with biometric information.

CITATION LIST

Patent Document

Patent Document 1: Japanese Patent Application Laid-Open No. 2019-199177

SUMMARY OF THE INVENTION

Problems to be Solved by the Invention

However, the electroencephalogram measurement has a large artifact due to the head myoelectric potential of the user, and the usage scene is currently limited. Therefore, a more convenient electroencephalogram input user interface has been required to be proposed.

The present technology has been made in view of such a situation, and an object thereof is to provide a more convenient electroencephalogram input user interface.

Solution to Problems

A control device according to an aspect of the present technology is a control device including a detection unit configured to perform detection of a brain wave included in a measured biometric signal of a user and detection of a user action based on information other than the brain wave included in the biometric signal, and a processing unit configured to perform a predetermined process based on the brain wave in a case where the user action is a predetermined action.

A control method according to an aspect of the present technology is a control method including a control device detecting a brain wave included in a measured biometric signal of a user and detecting a user action based on information other than the brain wave included in the biometric signal, and performing a predetermined process based on the brain wave in a case where the user action is a predetermined action.

In a control device and a control method according to an aspect of the present technology, a brain wave included in a measured biometric signal of a user is detected, a user action based on information other than the brain wave included in the biometric signal is detected, and a predetermined process based on the brain wave is performed in a case where the user action is a predetermined action.

The control device according to an aspect of the present technology may be an independent device or an internal block constituting one device.

BRIEF DESCRIPTION OF DRAWINGS

FIG. 17 is a diagram illustrating an example of a trigger action signal recording table.

FIG. 18 is a diagram illustrating an example of a trigger action-specific electroencephalogram application table.

FIG. 41 is a diagram illustrating an example of a CBPA table.

MODE FOR CARRYING OUT THE INVENTION

1. First Embodiment

Figure 1:
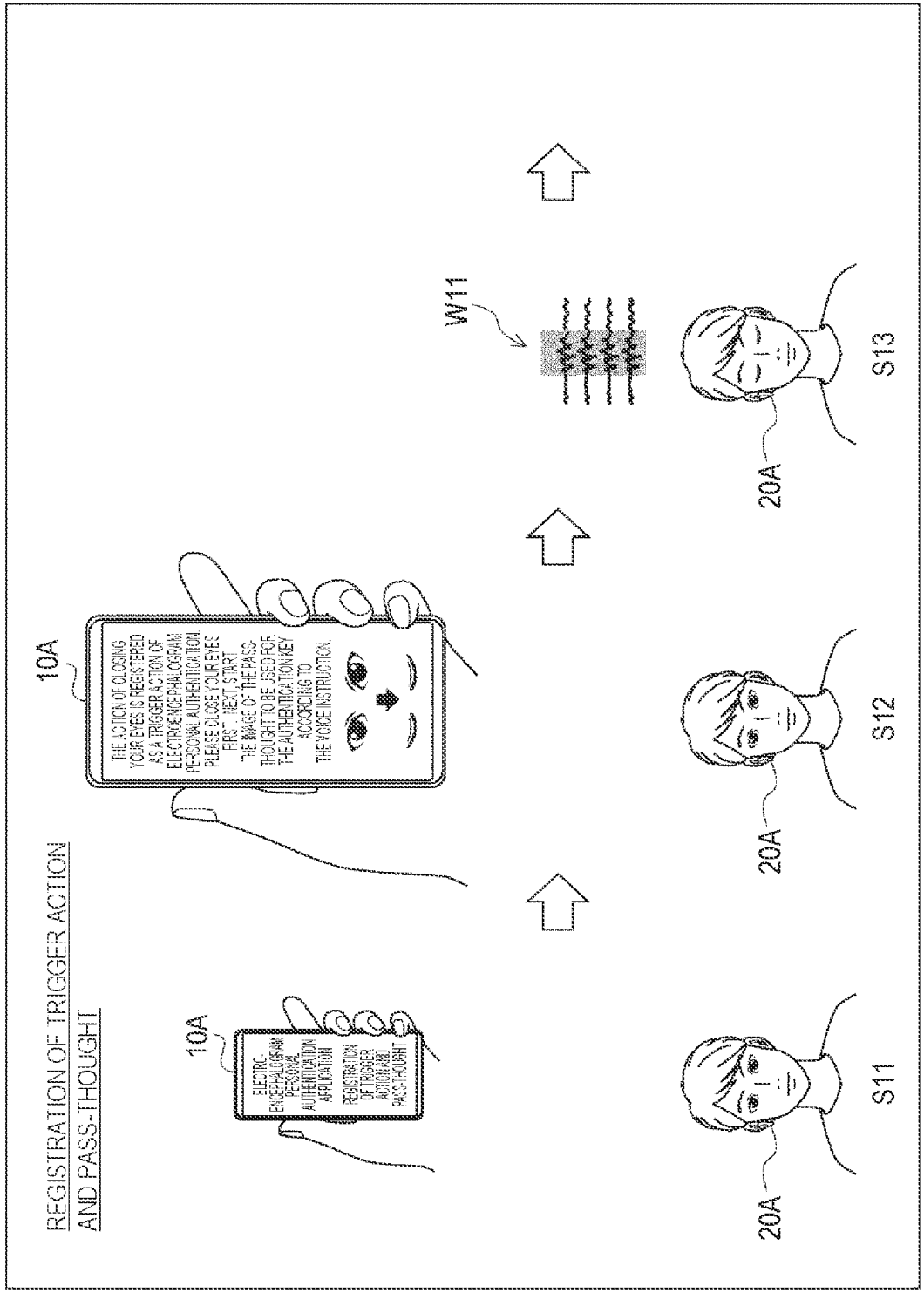
FIG. 1 is a diagram illustrating a registration example of a trigger action and a pass-thought.

Currently, a multi-factor authentication system using a plurality of verification elements is often used for authentication in which high security is required, such as in a bank. In order to perform multi-factor authentication, a user who intends to receive authentication is required to present two or more categories of authentication elements among the following (a) to (c).

(a) Knowledge: information known only by the user (for example, a password)

(b) Belongings: a thing that only the user has (for example, ATM card)

(c) Biometric information: a feature (for example, fingerprint) that only the user has However, the multi-factor authentication system is systemically complicated and expensive. In addition, from the viewpoint of user experience (UX), since there are many steps, it is hard to say that it is user-friendly.

Brain waves that can be read from electroencephalograph (EEG), and brain activities that can be read from magnetic resonance imaging (MRI) and near-infrared spectroscopy (NIRS) have features indicating individual differences.

When a pass-thought known only by the user can be read with accuracy with which it is possible to discriminate between individuals, authentication can be performed in one process by using knowledge known only by the user corresponding to the above-described (a) as a first authentication element and biometric information such as a brain feature amount of the user corresponding to the above-described (c) as a second authentication element at the same time.

The pass-thought is brain activity information specific to a case where an arbitrary object is perceived and recalled. The arbitrary object includes a voice, an image, an odor, a tactile sense, a taste sense, and the like. These may be actually recognized and perceived, or may be recalled or imagined although not actually perceived.

The recalling or imagining may be performed on the basis of a direct or specific instruction indicating the object, or may be performed on the basis of an abstract instruction. As an example of the former case, a case where the user imagines an apple on the basis of an instruction to imagine an apple is assumed. In addition, as an example of the latter, a case where the user imagines an apple on the basis of an instruction to imagine a favorite fruit is assumed. The brain activity information is information obtained by brain wave, MRI, or the like, and may be defined as a measurement signal, or a feature amount extracted from the measurement signal, or a space including the feature amount.

On the other hand, the electroencephalogram measurement has a large artifact due to the head myoelectric potential of the user, and the usage scene is currently limited.

That is, at the time of electroencephalogram measurement, an artifact caused by blinking or myoelectric potential of the chin is a problem. Therefore, in normal electroencephalogram measurement, measurement with the eyes closed is performed in a resting state. For this reason, there is a problem that a user interface (UI) using a brain wave signal as an input signal has a limited use scene and is difficult to implement in society.

Therefore, in the present technology, by providing a user interface of an electroencephalogram measurement machine using a head myoelectric potential, processing regarding a brain wave such as electroencephalogram personal authentication having a user interface (UI) that is natural and easy for all people to understand is realized while solving these problems. Hereinafter, a first embodiment will be described with reference to the drawings.

First Example

Figure 2:
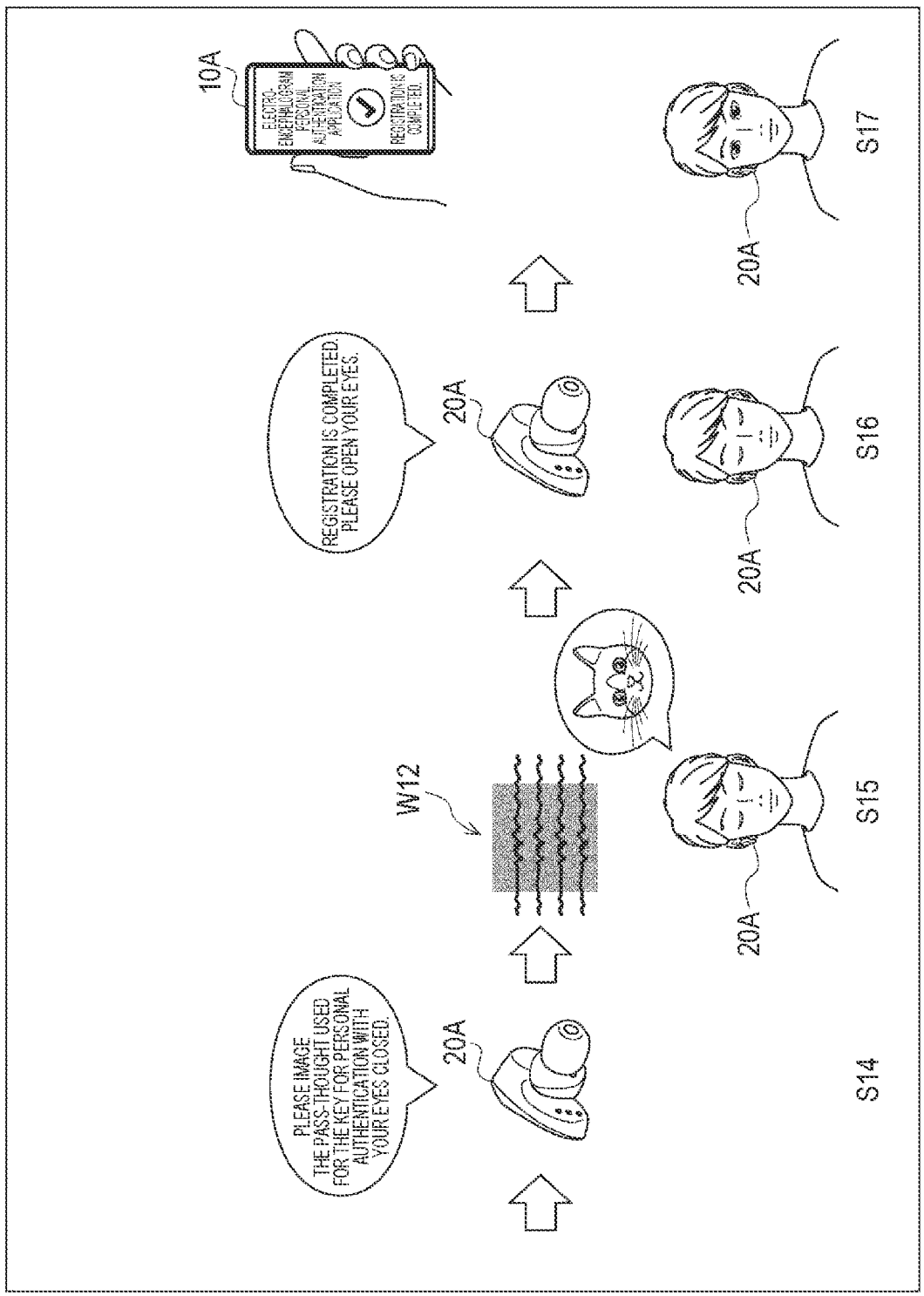
FIG. 2 is a diagram illustrating a registration example of a trigger action and a pass-thought.

FIGS. 1 and 2 illustrate a registration example of a trigger action and a pass-thought used in electroencephalogram personal authentication.

In FIGS. 1 and 2, the user holds a mobile terminal 10A such as a smartphone in the hand, and wears on the ear an earphone 20A connected to the mobile terminal 10A in a wireless or wired manner. Although details will be described later, the earphone 20A is provided with a plurality of electrodes, and can measure a biometric signal such as a myoelectric signal or a brain wave signal from the head of the user.

The user operates the menu screen of the electroencephalogram personal authentication application being activated on the mobile terminal 10A to select registration of a trigger action and a pass-thought (S11). The electroencephalogram personal authentication application is an application that performs personal authentication using a brain wave measured from the head of the user, and is an example of the electroencephalogram application. The trigger action is an action (a predetermined action or the like of the user) serving as a trigger when the predetermined process based on the brain wave is performed.

In response to this selection operation, the mobile terminal 10A presents a user interface that prompts the user to take a predetermined action with an image, text, sound, or the like (S12). In this example, a screen including a message prompting to close eyes and start an image of a pass-thought according to a voice instruction is displayed by an image and text. The voice instruction is an instruction by voice and is an example of an instruction that is an explicit instruction from the system.

When the user closes the eyes according to the message displayed on mobile terminal 10A, the myoelectric signal corresponding to the action is measured by the electrode of the earphone 20A (S13). In this example, in response to the user's eye closing, the myoelectric signal including the waveform W11 of FIG. 1 is measured and recorded as a trigger action signal.

Thereafter, a voice instruction that prompts the user with the eyes closed to image a pass-thought to be used as a key for electroencephalogram personal authentication is output from the earphone 20A (S14).

When the user imagines a pass-thought according to the voice instruction, the brain wave signal is measured by the electrode of the earphone 20A (S15). In this example, when the user images a cat, a brain wave signal including the waveform W12 in FIG. 2 is measured and recorded in association with an electroencephalogram personal authentication application as an electroencephalogram application and eye closing as a trigger action.

When the trigger action and the pass-thought are registered, a voice notifying the user that the registration is completed and that the eyes may be opened is output from the earphone 20A (S16). In addition, a user interface indicating that the registration is completed is presented in the mobile terminal 10A by an image, text, sound, or the like (S17). In this example, a screen including a message indicating completion of registration is displayed by an image and a text.

In this manner, the user performs an action or the like serving as a trigger action according to the user interface (UI) such as a voice instruction or images a thing or the like used as a pass-thought, whereby the trigger action and the pass-thought used in the electroencephalogram personal authentication are registered.

Figure 3:
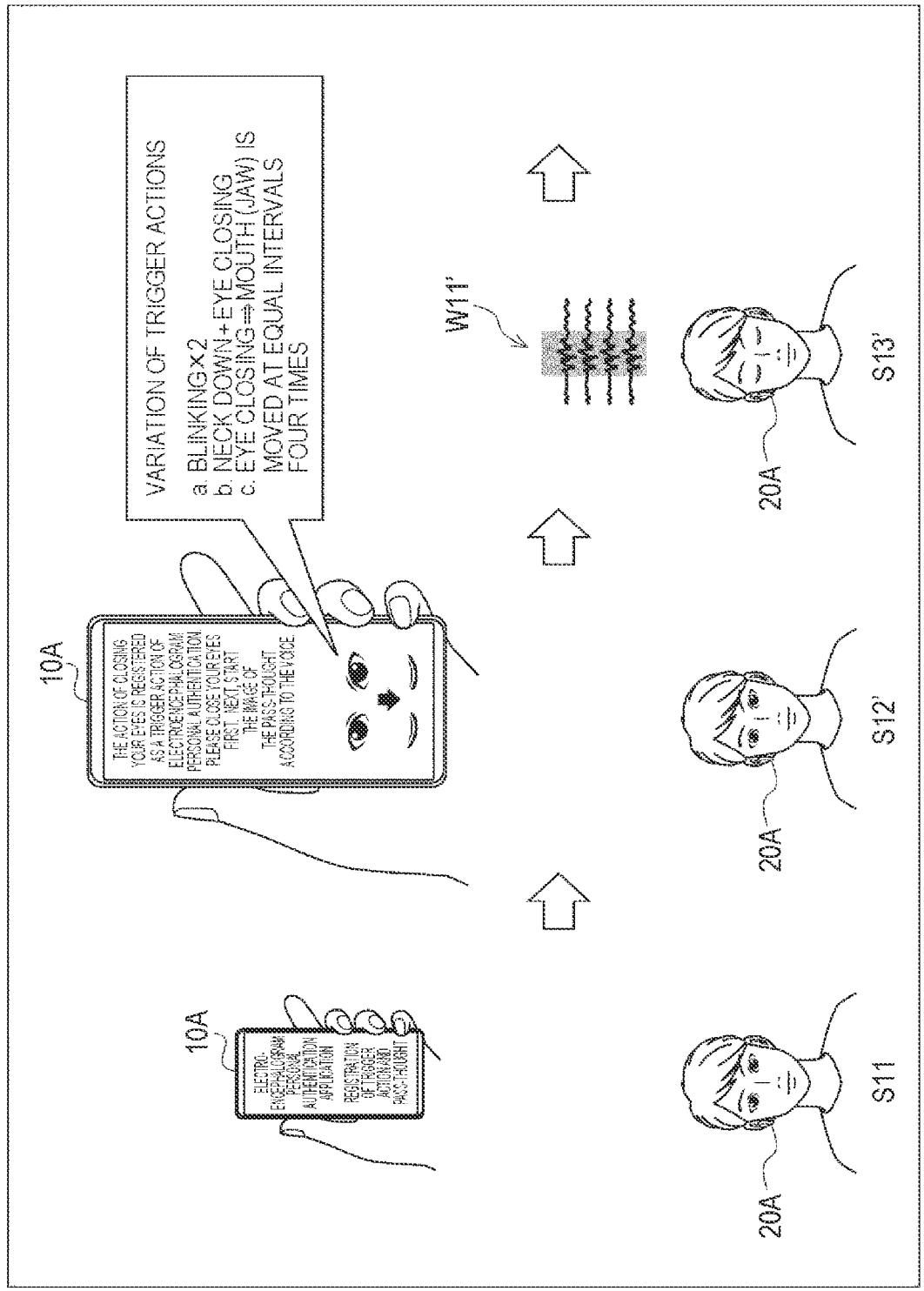
FIG. 3 is a diagram illustrating an example of a variation of a trigger action.

In the above description, the example in which the user registers the eye closing action as the trigger action (S12 and S13 in FIG. 1) is described. However, as illustrated in FIG. 3, another action by the user may be registered as the trigger action by presenting a user interface that prompts an action such as blinking twice, closing the eyes with the neck down, or closing the eyes and moving the mouth (jaw) only four times at predetermined intervals (S12').

As a result, according to the presented user interface, the user performs an action such as blinking twice, closing the eyes with the neck down, or moving the mouth (jaw) four times after closing the eyes, whereby the myoelectric signal including the waveform W11' corresponding to the action is measured and recorded as the trigger action signal (S13'). That is, the user interface presented here is an instruction that is an explicit instruction from the system, and prompts the user to perform a trigger action.

Figure 4:
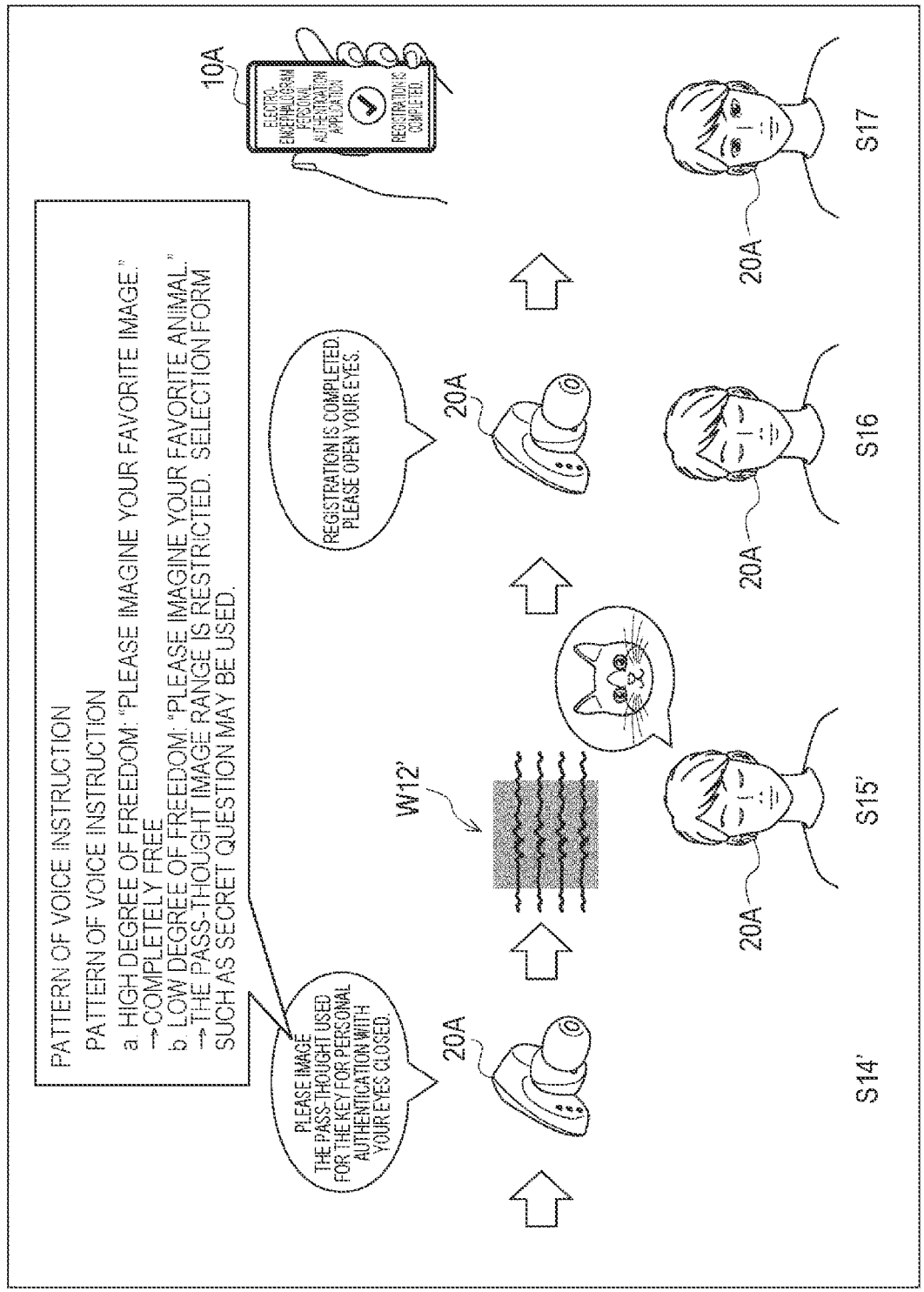
FIG. 4 is a diagram illustrating an example of a pattern of a voice instruction.

In addition, in the above description, the example in which the user images an arbitrary object (thing or the like) as the pass-thought (S14 and S15 in FIG. 2) is described. However, as illustrated in FIG. 4, it is not limited to a voice instruction that prompts the user to completely freely imagine a favorite image, but the image range of the pass-thought may be restricted by a voice instruction such as "please imagine an animal you like", and the degree of freedom may be lowered. Alternatively, a person, a scene, a motion of the body of the user, a word, a number, a melody, a song, or the like may be imagined, or a selection form such as a secret question may be used.

As a result, a brain wave signal including a waveform W12' corresponding to the image of the answer of the user to the more limited favorite animal or secret question is measured and recorded in association with the electroencephalogram application and the trigger action (S15').

Note that, at the time of registering the trigger action and the pass-thought described above, by repeatedly performing the processes of steps S12 to S17 in FIGS. 1 and 2 a plurality of times, it is possible to register the trigger action signal and the brain wave signal with higher accuracy, and it is possible to increase the accuracy of the electroencephalogram personal authentication using the trigger action and the pass-thought.

Figure 5:
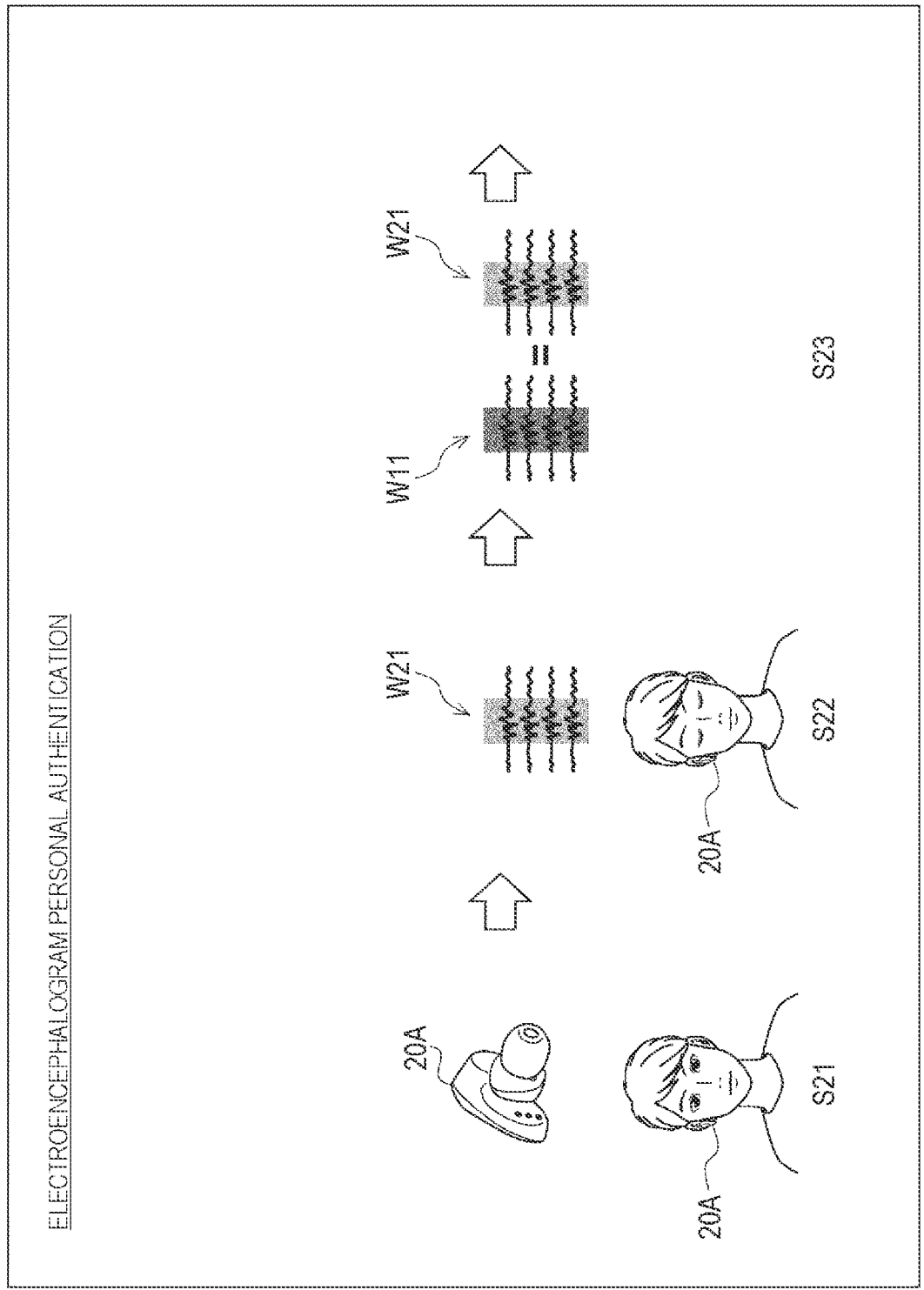
FIG. 5 is a diagram illustrating an authentication example of electroencephalogram personal authentication.
Figure 6:
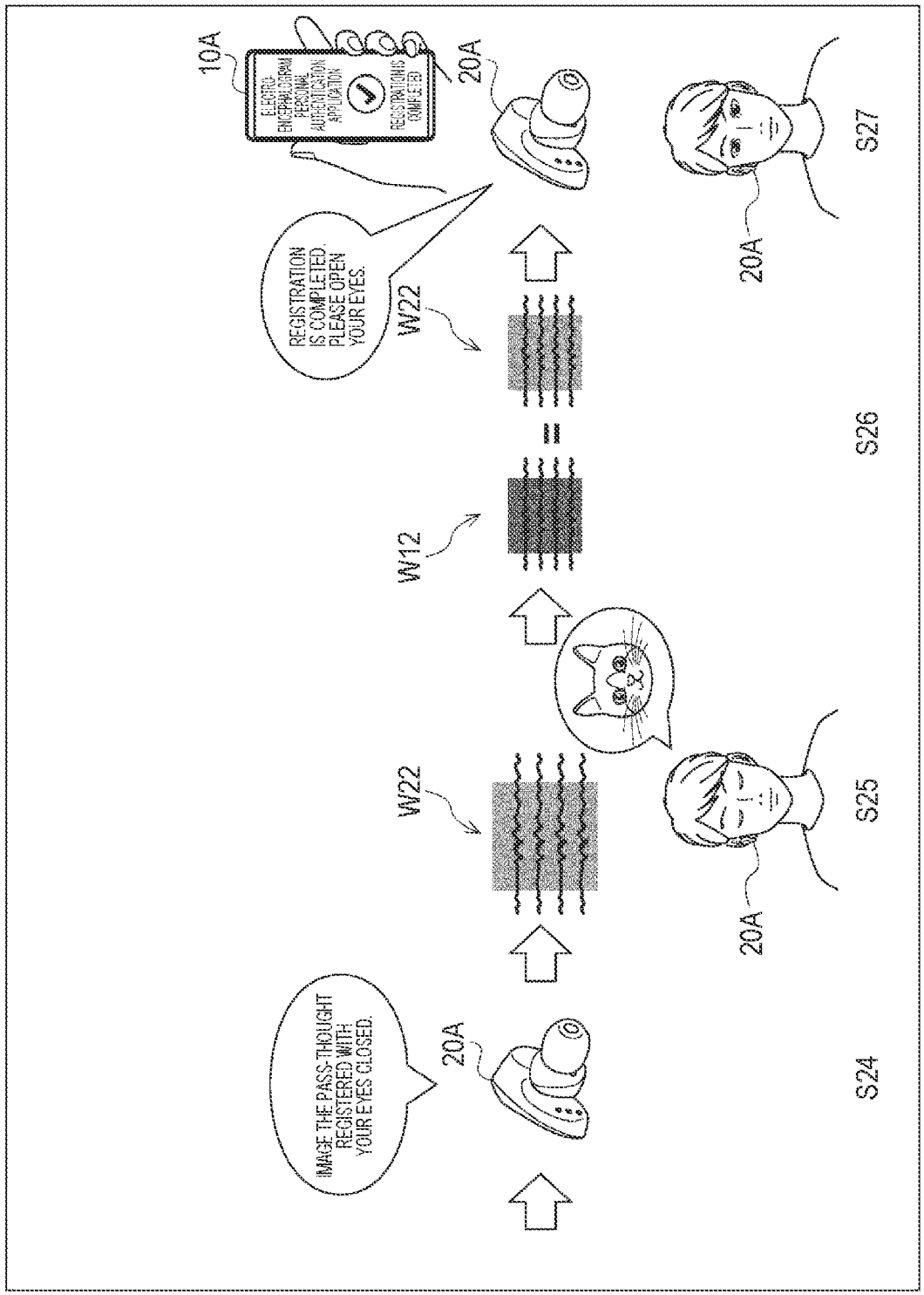
FIG. 6 is a diagram illustrating an authentication example of electroencephalogram personal authentication.

FIGS. 5 and 6 illustrate an authentication example of electroencephalogram personal authentication (pass-thought authentication) using a trigger action and a pass-thought.

In FIGS. 5 and 6, the user holds the mobile terminal 10A such as a smartphone in the hand, and wears on the ear the earphone 20A connected to the mobile terminal 10A in a wireless or wired manner. The earphone 20A is operating in a trigger action measurement mode (S21).

At this time, when the user closes the eyes, the myoelectric signal corresponding to the action is measured by the electrode of the earphone 20A (S22). In this example, the myoelectric signal including a waveform W21 of FIG. 5 is detected as the trigger action signal, and the trigger action recognition process is initiated in the earphone 20A.

In this trigger action recognition process, it is checked whether a trigger action signal having a similarity within a predetermined threshold value range exists in the trigger action signal recorded at the time of registration. In addition, from the relationship between the recorded trigger action signal and the electroencephalogram application, notification of the detection of the trigger action signal is provided to the corresponding electroencephalogram application.

In this example, since the waveform W21 of the myoelectric signal detected as the trigger action signal at the time of authentication has a similarity within the predetermined threshold value range with the waveform W11 of the myoelectric signal recorded as the trigger action signal at the time of registration, the trigger action is eye closing, and the corresponding electroencephalogram application is the electroencephalogram personal authentication application (S23).

When the trigger action and the electroencephalogram application are identified, a voice instruction that prompts the user with the eyes closed to image the registered pass-thought is output from the earphone 20A (S24). In the earphone 20A, the measurement mode is changed from the trigger action measurement mode to the electroencephalogram measurement mode.

When the user imagines the pass-thought according to the voice instruction, the brain wave signal is measured by the electrode of the earphone 20A (S25). In this example, since the user has imaged a cat, the brain wave signal including the waveform W22 in FIG. 6 is measured, and the pass-thought recognition process is started.

In this pass-thought recognition process, it is checked whether there is a signal having a similarity within a predetermined threshold value in the brain wave signal recorded for each corresponding electroencephalogram application.

In this example, since the waveform W22 of the brain wave signal measured at the time of authentication has a similarity within the range of the predetermined threshold value with the waveform W12 of the brain wave signal recorded as the brain wave signal of the electroencephalogram personal authentication application, the electroencephalogram personal authentication application is notified that the brain wave signals match (S26).

Note that, in a case where there is no brain wave signal having a similarity within a range of a predetermined threshold value with the waveform W22 of the measured brain wave signal, the electroencephalogram personal authentication application is notified that the brain wave signals do not match.

When the pass-thought recognition process is completed, a voice notifying the user that the authentication is completed and that the eyes may be opened is output from the earphone 20A (S27). Further, the mobile terminal 10A displays a screen including a message indicating that the authentication is completed by an image or a text (S27).

In this manner, the user performs an action or the like serving as a trigger action according to the user interface (UI) such as a voice instruction, or images a thing or the like used as a pass-thought, whereby the electroencephalogram personal authentication is performed.

Example of External Induction

In the above description, an example in which the user actively images the pass-thought at the time of registration and authentication in the electroencephalogram personal authentication is described, but the pass-thought imaged by the user may be induced from the outside. First, an example of electroencephalogram personal authentication using an auditory induction response will be described with reference to FIGS. 7 and 8.

Figure 7:
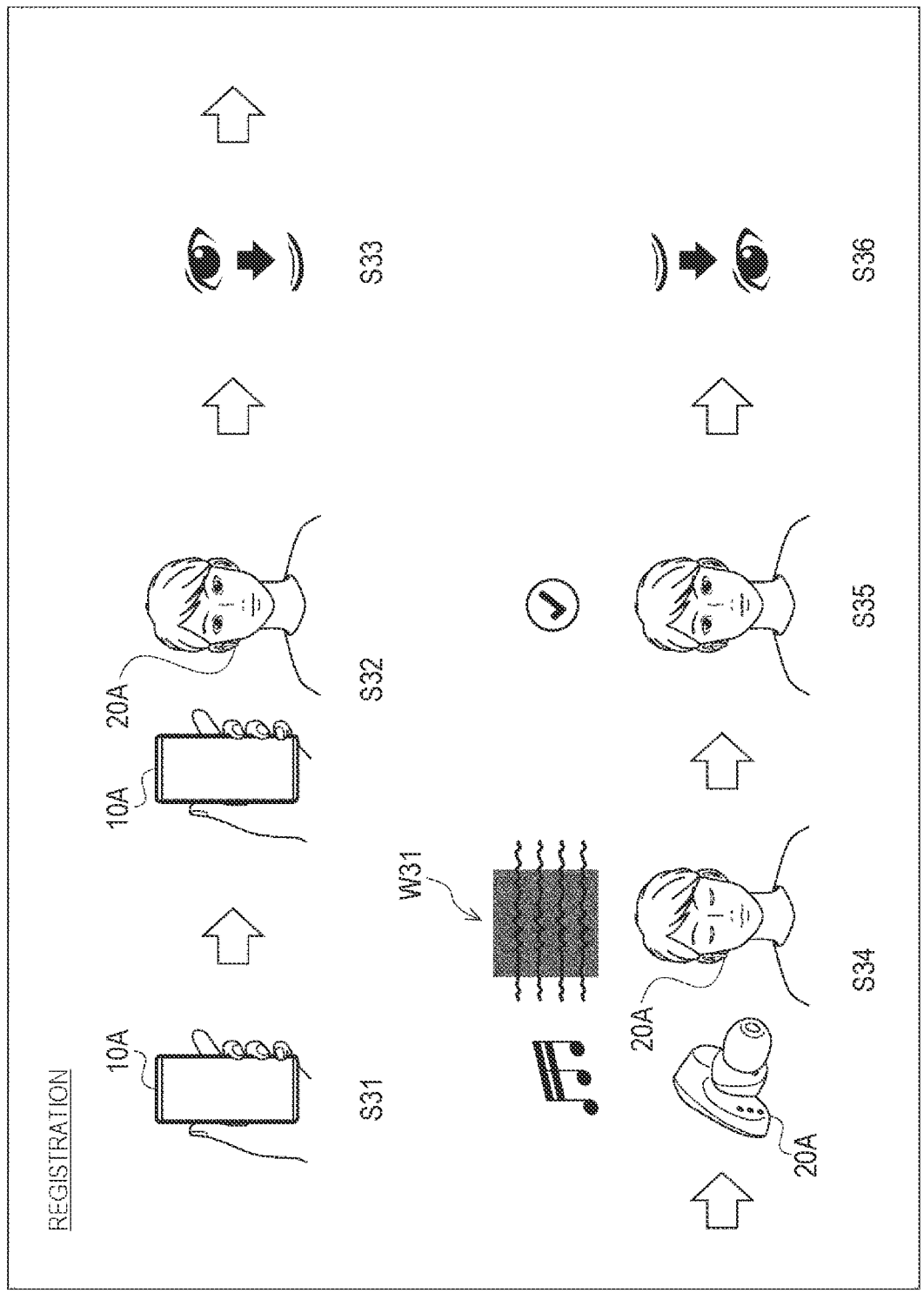
FIG. 7 is a diagram illustrating a registration example of electroencephalogram personal authentication using an auditory induction response.

FIG. 7 illustrates a registration example of electroencephalogram personal authentication using an auditory induction response.

The user operates the menu screen of the electroencephalogram personal authentication application being activated on the mobile terminal 10A to select registration of a trigger action and a pass-thought (S31). Note that it is possible to select to use the auditory induction response on this menu screen.

In response to this selection operation, the mobile terminal 10A presents a message prompting the user to close the eyes and listen to the sound output from the earphone 20A with an image, a text, a sound, or the like (S32).

When the user closes the eyes according to the message presented to the mobile terminal 10A, the myoelectric signal corresponding to the action is measured by the electrode of the earphone 20A and recorded as a trigger action signal (S33).

Thereafter, the induction sound is output from the earphone 20A to the user with the eyes closed, and when the user responds to the induction sound, the brain wave signal corresponding to the response is measured by the electrode of the earphone 20A, and recorded in association with the electroencephalogram personal authentication application and the trigger action (S34).

When the pass-thought corresponding to the auditory induction response is registered, a voice notifying the user that the registration is completed and that the eyes may be opened is output from the earphone 20A (S35).

According to the voice instruction, when the user opens the eye, the myoelectric signal corresponding to the action is measured by the electrode of earphone 20A, and is recorded as the trigger action signal (S36). That is, in this example, by recording a series of actions when the user closes the eyes and when the user opens the eyes, the opening/closing action of the eyes is recorded as the trigger action.

Note that it is possible to register the pass-thought according to the auditory induction response with higher accuracy by repeating the processes of steps S32 to S34 described above a plurality of times and checking whether a waveform matches (or is similar to) the previous waveform.

Figure 8:
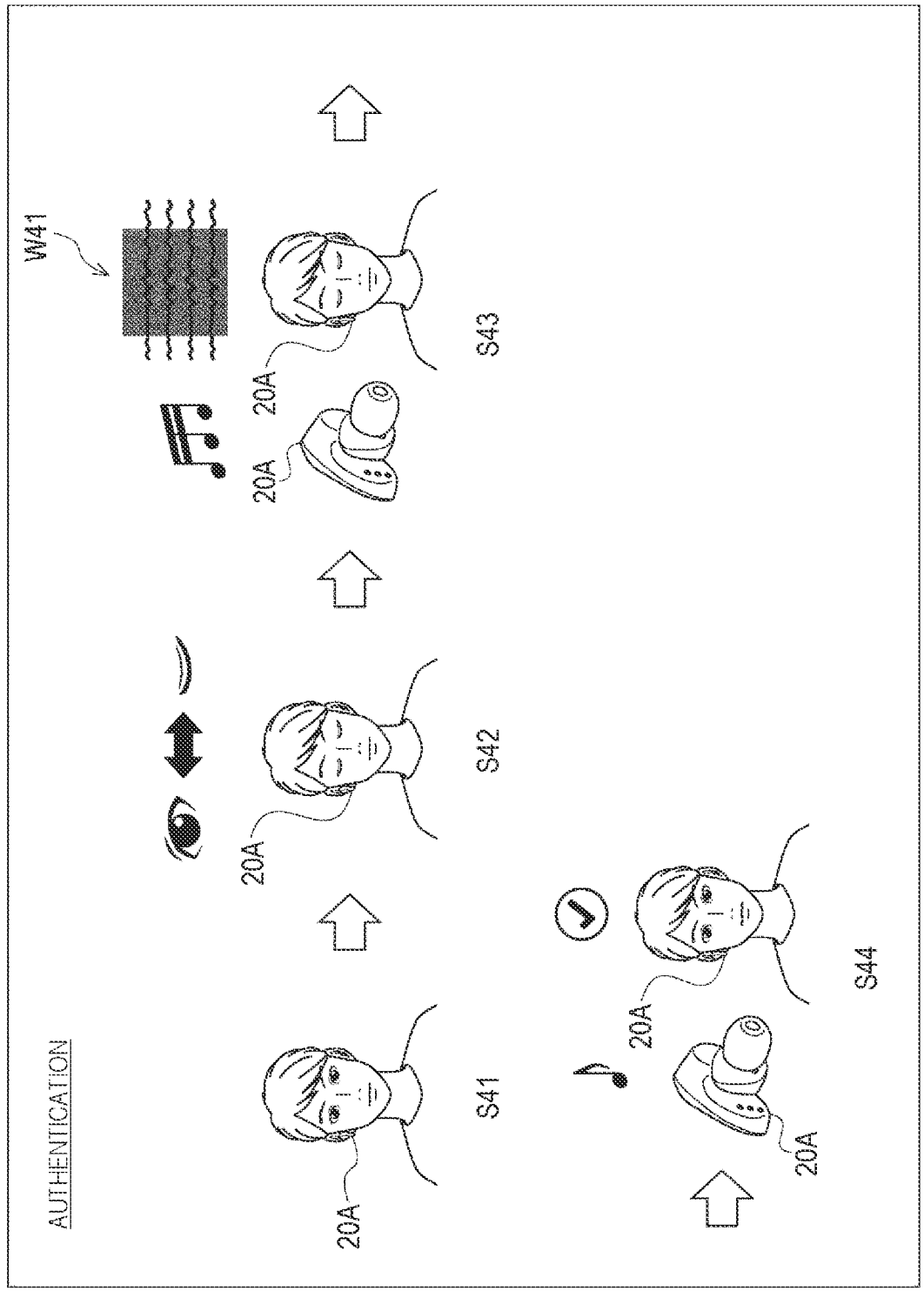
FIG. 8 is a diagram illustrating an authentication example of electroencephalogram personal authentication using an auditory induction response.

FIG. 8 illustrates an authentication example of electroencephalogram personal authentication using an auditory induction response.

The earphone 20A worn on the ear by the user is operating in a trigger action measurement mode (S41). When the user opens and closes the eyes, a myoelectric signal corresponding to the action is detected as a trigger action signal, and a trigger action recognition process is started.

In this example, in the trigger action recognition process, since the myoelectric signal detected as the trigger action signal at the time of authentication has a similarity within the range of the predetermined threshold value with the myoelectric signal recorded as the trigger action signal at the time of registration described above, the trigger action is opening and closing of the eyes, and the corresponding electroencephalogram application is the electroencephalogram personal authentication application (S42).

Once the trigger action and electroencephalogram application are identified, the measurement mode is changed to the electroencephalogram measurement mode. Then, the induction sound is output from the earphone 20A to the user with the eyes closed, and when the user responds to the induction sound, the brain wave signal corresponding to the response is measured by the electrode of the earphone 20A, and the ERP recognition process is started (S43). The event-related potential (ERP) is a brain response (typological electrophysiological response to internal and external stimuli) measured in some form as a result of a thought or cognition of a user.

In this example, in the ERP recognition process, since the brain wave signal measured at the time of authentication has a similarity within a range of a predetermined threshold value with the brain wave signal recorded as the brain wave signal of the electroencephalogram personal authentication application, the electroencephalogram personal authentication application is notified that the brain wave signals match.

When the ERP recognition process is completed, a sound (authentication clear sound) indicating that the authentication is completed and a voice making notification that the eyes may be opened are output from the earphone 20A to the user (S44).

In this way, by using the auditory induction response, the user can realize the electroencephalogram personal authentication only by listening to the induction sound output from the outside without imaging the pass-thought used for the authentication key by himself/herself.

Note that various sounds can be used as the induction sound, but an odd ball task in which an abnormal sound is mixed with a normal sound may be used. The odd ball task is to present two or more kinds of sounds in a random order with different appearance frequencies.

Next, an example of electroencephalogram personal authentication using a visual induction response will be described with reference to FIGS. 9 and 10.

Figure 9:
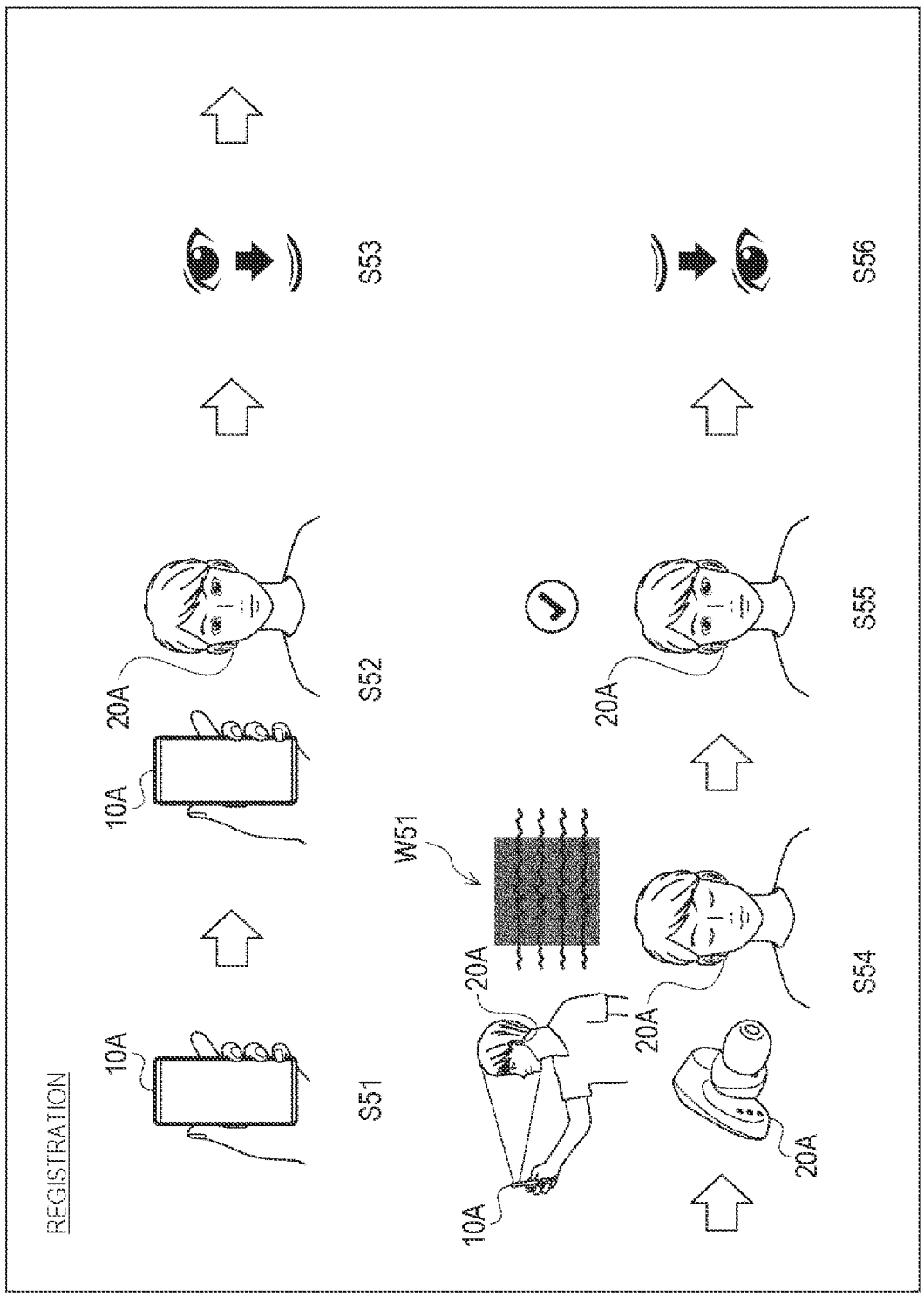
FIG. 9 is a diagram illustrating a registration example of electroencephalogram personal authentication using a visual induction response.

FIG. 9 illustrates a registration example of electroencephalogram personal authentication using a visual induction response.

As in steps S31 to S33 of FIG. 7, in steps S51 to S53 of FIG. 9, when the user closes the eyes according to the message presented by the mobile terminal 10A or the earphone 20A, the myoelectric signal corresponding to the action is measured by the electrode of the earphone 20A and recorded as the trigger action signal.

The user with the eyes closed is irradiated with the inductive light using the visual induction illumination function of the mobile terminal 10A, and when the user responds to the inductive light, the brain wave signal corresponding to the response is measured by the electrode of the earphone 20A, and recorded in association with the electroencephalogram personal authentication application and the trigger action (S54).

For example, as the visual induction illumination, flash illumination with a specific pulse is used, and flash is only required to be enabled at a speed at which the user is not conscious, but at which an induction response occurs in the brain wave signal. Note that the visual induction illumination function is described as a function of the mobile terminal 10A, but may be provided as a function of another device.

As in steps S35 and S36 of FIG. 7, in steps S55 to S56 of FIG. 9, after notification of the completion of the registration is provided, the myoelectric signal corresponding to the action when the user opens the eyes is measured and recorded as the trigger action signal. That is, in this example, by recording a series of actions when the user closes the eyes and when the user opens the eyes, the opening/closing action of the eyes is recorded as the trigger action.

Note that it is possible to register the pass-thought according to the visual induction response with higher accuracy by repeating the processes of steps S52 to S54 described above a plurality of times and checking whether a waveform matches (or is similar to) the previous waveform.

Figure 10:
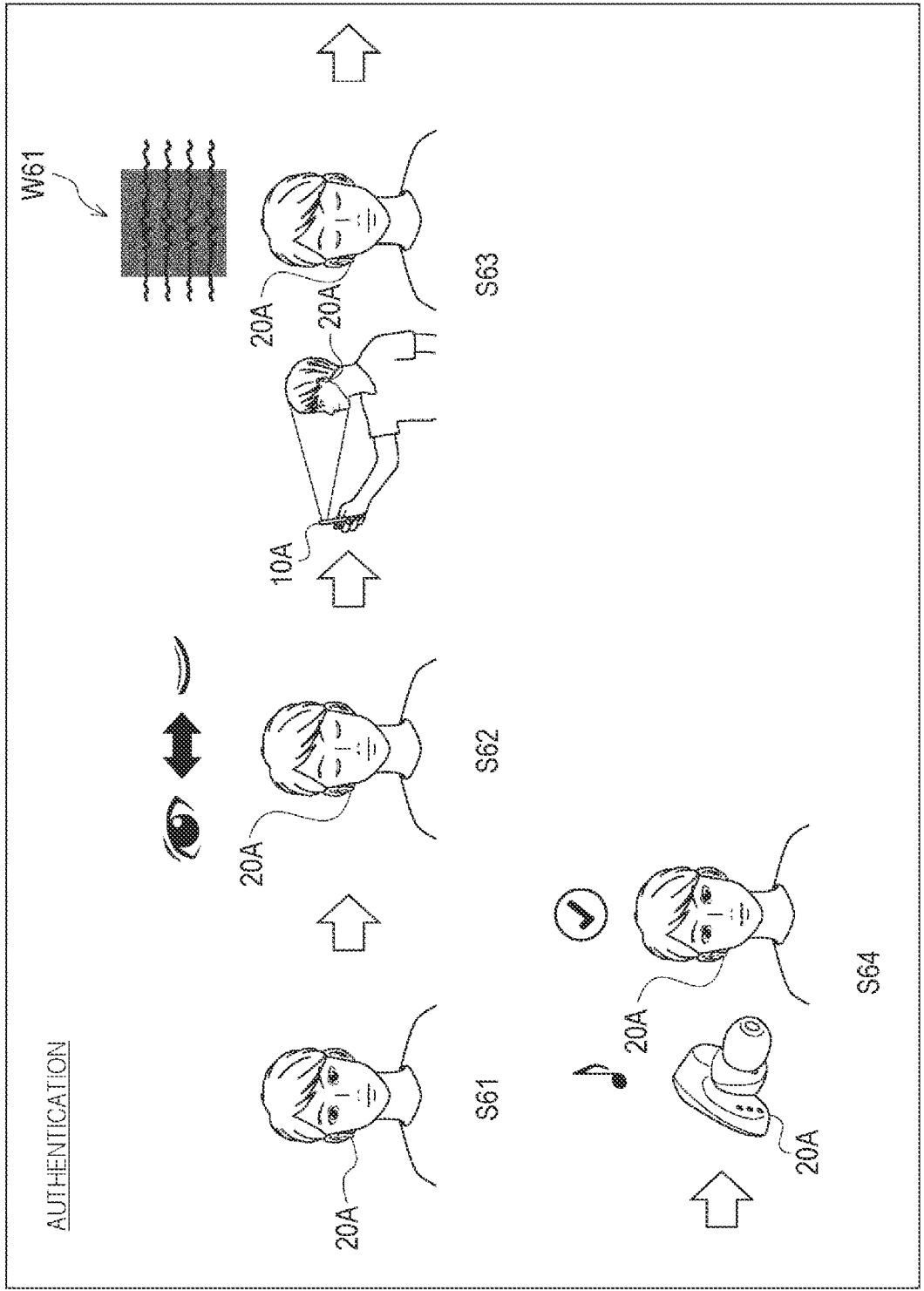
FIG. 10 is a diagram illustrating an authentication example of electroencephalogram personal authentication using a visual induction response.

FIG. 10 illustrates an authentication example of electroencephalogram personal authentication using a visual induction response.

As in steps S41 to S42 of FIG. 8, in steps S61 to S62 of FIG. 10, in a case where the myoelectric signal corresponding to the action when the user opens and closes the eyes is detected as the trigger action signal, and has a similarity within a predetermined threshold value range with the trigger action signal recorded at the time of registration, the ERP recognition process is started (S63).

In this ERP recognition process, when the user responds to the inductive light radiated by the mobile terminal 10A, the brain wave signal corresponding to the response is measured. Therefore, in a case where the measured brain wave signal has a similarity within a predetermined threshold value range with the brain wave signal recorded as the brain wave signal of the electroencephalogram personal authentication application, the electroencephalogram personal authentication application is notified that the brain wave signals match.

As in step S44 of FIG. 8, in step S64 of FIG. 10, when the authentication of the pass-thought is completed, a sound (authentication clear sound) indicating that the authentication is completed and a voice making notification that the eyes may be opened are output from the earphone 20A to the user.

In this way, by using the visual induction response, the user can realize the electroencephalogram personal authentication only by receiving the radiation of the inductive light output from the outside without imaging the pass-thought used for the authentication key by himself/herself.

Note that continuous and sustained electroencephalogram personal authentication may be performed when a pulse at a speed at which the user is not conscious is inserted into a signal, for example, in a room light, and the signal matches the brain wave signal of the visual induction response registered in advance. In addition, at this time, the concentration of the user by the brain wave signal of the visual induction response may be measured.

Furthermore, since the room light or the like is used, the electroencephalogram personal authentication can be simultaneously performed not only for one user but also for a plurality of users in the room. For example, by providing the function of the electroencephalogram personal authentication as a function of the conference room application, in a case where the conference room is used by a plurality of users, the electroencephalogram personal authentication is performed on the users in the conference room, and it is possible to grasp the participation status of the conference.

In addition, in the above description, the electroencephalogram personal authentication using the auditory induction response and the visual induction response has been exemplified, but in addition to this, a tactile induction response by vibration of a device such as the mobile terminal 10A, an olfactory induction response by a scent generation device, or the like may be used. Such a brain wave signal induced by hearing, vision, touch, or smell can also be said to be an event-related potential (ERP).

Second Example

In the above description, the example in which the electroencephalogram personal authentication application is executed as the electroencephalogram application is described, but the present technology can be applied even in a case where another electroencephalogram application is used. An example of the recall search (brain log search) using the electroencephalogram search application will be described with reference to FIGS. 11 and 12.

Figure 11:
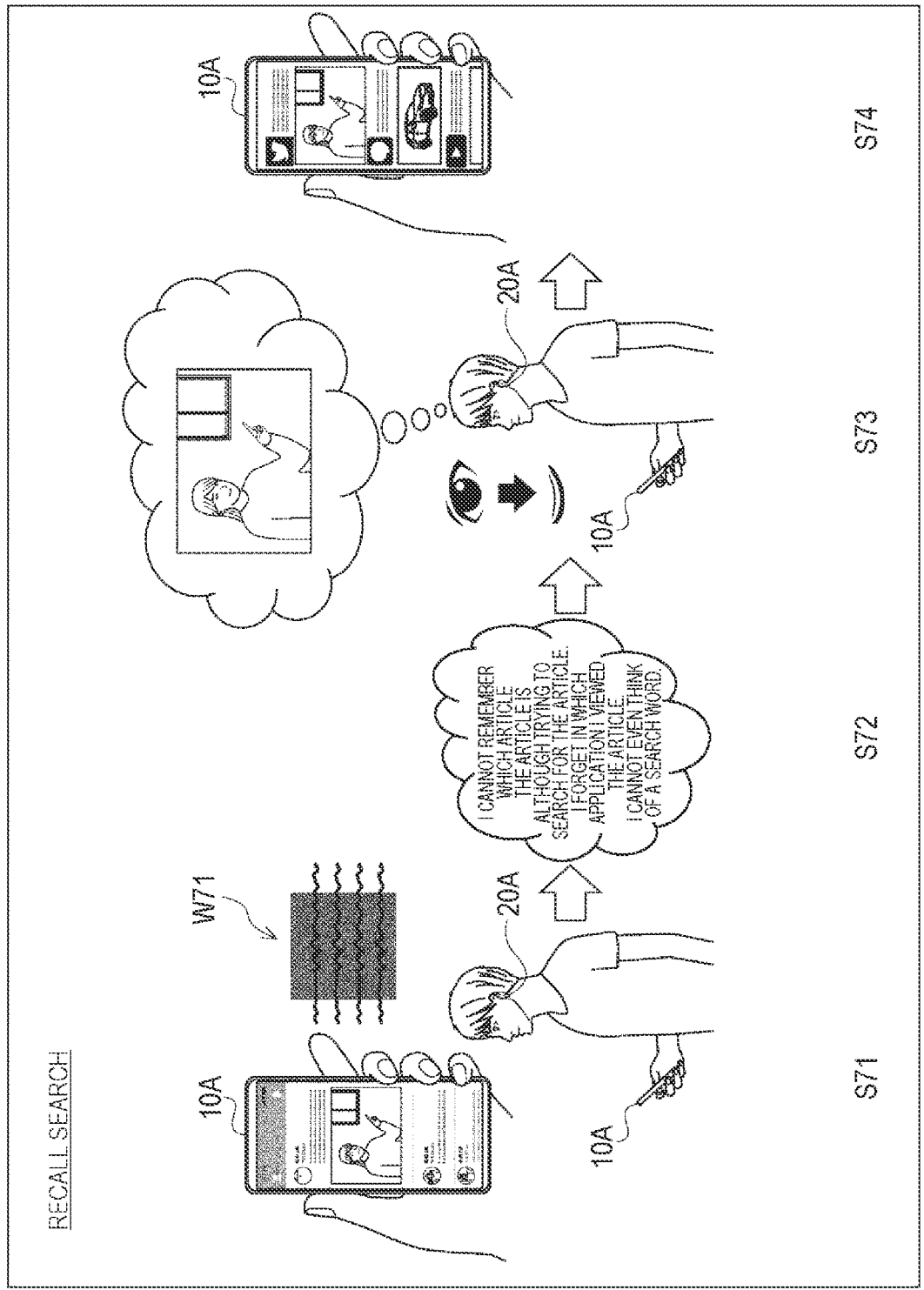
FIG. 11 is a diagram illustrating a first example of recall search.

FIG. 11 illustrates a first example of the recall search using the electroencephalogram search application.

In FIG. 11, the user holds the mobile terminal 10A such as a smartphone in the hand, and wears on the ear the earphone 20A connected to the mobile terminal 10A in a wireless or wired manner. In addition, in the mobile terminal 10A, applications such as a social networking service (SNS) application and a news application are activated.

At this time, in a case where the user operates the mobile terminal 10A and browses an article of an SNS application and the like, a scene in which there is an article of interest is assumed (S71).

In this scene, the brain wave signal of the user when browsing the article of interest is measured and recorded by the electrode of the earphone 20A.

Regarding the timing of recording the brain wave signal, for example, when an article fixedly displayed for a certain period of time or more is detected on the mobile terminal 10A, it is estimated that the user has been paying attention to and browsing the article, and the brain wave signal at that time is automatically recorded.

In this example, a brain wave signal including a waveform W71 in FIG. 11 is measured and recorded as a brain wave signal of the user when an article fixedly displayed for a certain period of time or more is detected. Recording of the brain wave signal can be associated with the electroencephalogram search application. In addition, the information regarding the recorded brain wave signal is associated with the information regarding the article of interest by information such as history information.

Thereafter, a scene is assumed in which the user tries to browse the article of interest again, but cannot remember which article it is although trying to search for the article of interest (S72). At this time, it is assumed that the user cannot even think of a search word on which application the user has browsed.

At this time, when the user closes the eyes, the myoelectric signal corresponding to the action is detected as a trigger action signal by the electrode of the earphone 20A, and the trigger action recognition process is started (S73). Note that, in this example, it is assumed that a user's eye closing action (eye closing) is registered in advance as a trigger action of the electroencephalogram search application.

In this trigger action recognition process, in a case where the detected trigger action signal has a similarity within a predetermined threshold value range with the recorded trigger action signal, the trigger action is eye closing, and the corresponding electroencephalogram application is an electroencephalogram search application.

When a trigger action and an electroencephalogram application are identified, and a user with the eyes closed thinks of an image of an article of interest, a brain wave signal corresponding to the image of the article of interest is measured by an electrode of the earphone 20A, and a brain log search process is started (S73).

In this brain log search process, matching is performed as to whether there is a waveform having a similarity within a predetermined threshold value range with the measured waveform of the brain wave signal among the waveforms of the brain wave signals recorded as the brain wave signals of the electroencephalogram search application. In this example, since the waveform of the measured brain wave signal has a similarity within a range of a predetermined threshold value with the waveform W71 of the recorded brain wave signal, the electroencephalogram search application is notified of information regarding the brain wave signal.

In the mobile terminal 10A, the electroencephalogram search application identifies information regarding the article of interest associated with the information regarding the brain wave signal notification of which is to be provided on the basis of the information such as the history information, and presents the article of interest on the basis of the information regarding the article of interest (S74). For example, the article of interest can be presented using a history option function or the like of the mobile terminal 10A. In addition, at the time of presenting the article of interest, in a case where there is a plurality of histories (records) in which the similarity of the waveform of the brain wave signal falls within the range of the threshold value, a plurality of matching results may be presented in descending order of the similarity.

In this manner, it is possible to realize the recall search (brain log search) by matching the brain wave signal automatically recorded when the user browses the article with the brain wave signal when the user recalled the storage of the article. As a result, even in a case where the user does not clearly remember the information regarding the article that the user has browsed, the user can browse the article again by recalling the memory of the article in his/her head.

Figure 12:
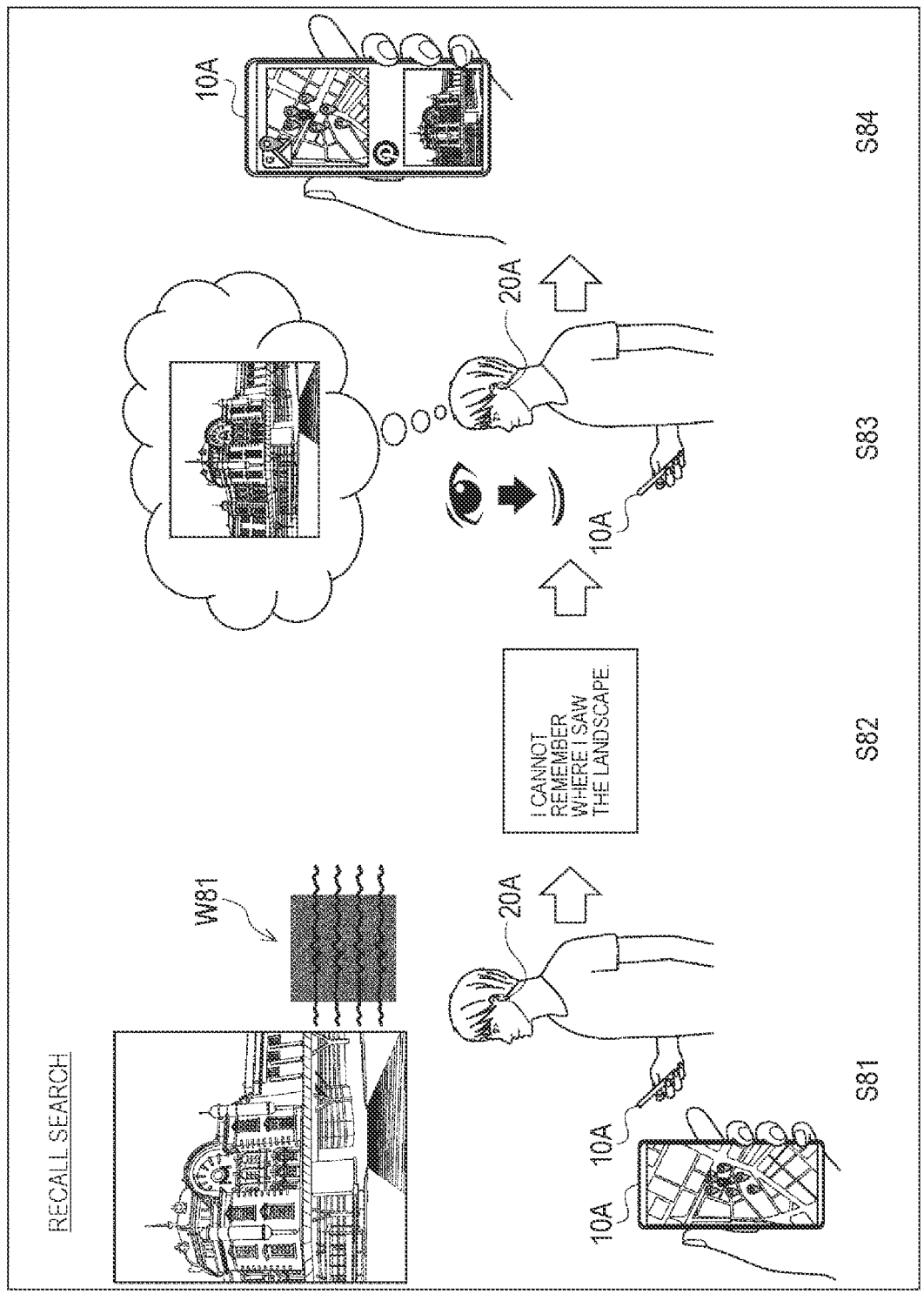
FIG. 12 is a diagram illustrating a second example of recall search.

FIG. 12 illustrates a second example of the recall search using the electroencephalogram search application.

In FIG. 12, a scene is assumed in which the user is heading to a destination such as a meeting destination while confirming the map application activated on the mobile terminal 10A held in the hand outdoors (S81).

In this scene, the brain wave signal of the user when the appearance of the building is confirmed on the way to the destination is measured and recorded by the electrode of the earphone 20A.

Regarding the timing at which the brain wave signal is recorded, for example, it is estimated that when a time for the user to stop for a certain period of time is detected after a map is displayed by a map application activated on the mobile terminal 10A, the appearance of the building is checked at that place, and the brain wave signal at that time is automatically recorded.

In this example, a brain wave signal including a waveform W81 in FIG. 12 is measured and recorded as a brain wave signal of the user when a time for the user to stop for a certain period of time is detected. Recording of the brain wave signal can be associated with the electroencephalogram search application. In addition, the information regarding the recorded brain wave signal is associated with information (position information or the like) regarding a place where the appearance of the building is estimated to have been confirmed on the basis of information such as history information.

Thereafter, a scene is assumed in which the user remembers the appearance of the building but cannot remember where the scene is seen (S82).

At this time, when the user closes the eyes, the myoelectric signal corresponding to the action is measured by the electrode of the earphone 20A, and the trigger action recognition process is started (S83). Note that, also in this example, it is assumed that eye closing is registered in advance as the trigger action.

In this trigger action recognition process, in a case where the detected trigger action signal has a similarity within a predetermined threshold value range with the recorded trigger action signal, the trigger action is eye closing, and the corresponding electroencephalogram application is an electroencephalogram search application.

When a trigger action and an electroencephalogram application are identified, and a user with the eyes closed thinks of an image of an impressive building, a brain wave signal corresponding to the image of the impressive building is measured by the electrode of the earphone 20A, and a brain log search process is started (S83).

In this brain log search process, matching is performed as to whether there is a waveform having a similarity within a predetermined threshold value range with the measured waveform of the brain wave signal among the waveforms of the brain wave signals recorded as the brain wave signals of the electroencephalogram search application. In this example, since the waveform of the measured brain wave signal has a similarity within a range of a predetermined threshold value with the waveform W81 of the recorded brain wave signal, the electroencephalogram search application is notified of information regarding the brain wave signal.

In the mobile terminal 10A, the electroencephalogram search application identifies a place (position information or the like) associated with the information regarding the brain wave signal notification of which is to be provided on the basis of the information such as the history information, and presents a map of the place, information regarding a building, or the like (S84). For example, a map of a specific place or information regarding a building can be presented by using a history option function of the mobile terminal 10A.

In this manner, it is possible to realize the recall search (brain log search) by matching the brain wave signal automatically recorded when the user visits a specific place with the brain wave signal when the user recalls the memory of a building or the like with an impression. As a result, even in a case where the user does not clearly memorize information regarding a building or the like with an impression at the place where the user has visited, the user can browse the information regarding the building or the like by using the mobile terminal 10A by recalling the memory of the building or the like in his/her head.

Note that FIGS. 11 and 12 illustrate a case where the trigger action of the electroencephalogram search application is eye closing for convenience of description. However, for example, another action such as blinking twice may be registered. That is, trigger actions of the electroencephalogram personal authentication application and the electroencephalogram search application can be different. In addition, in the above-described example, the brain wave signal regarding a thought of the user for the same object such as a specific article or a specific place is described as the brain wave signal to be subjected to the matching process. The same object can include information, such as a still image, a moving image, a contact address, music, or an application, that can be presented by a device such as the mobile terminal 10A and that is provided by a specific medium.

(System Configuration)

Figure 13:
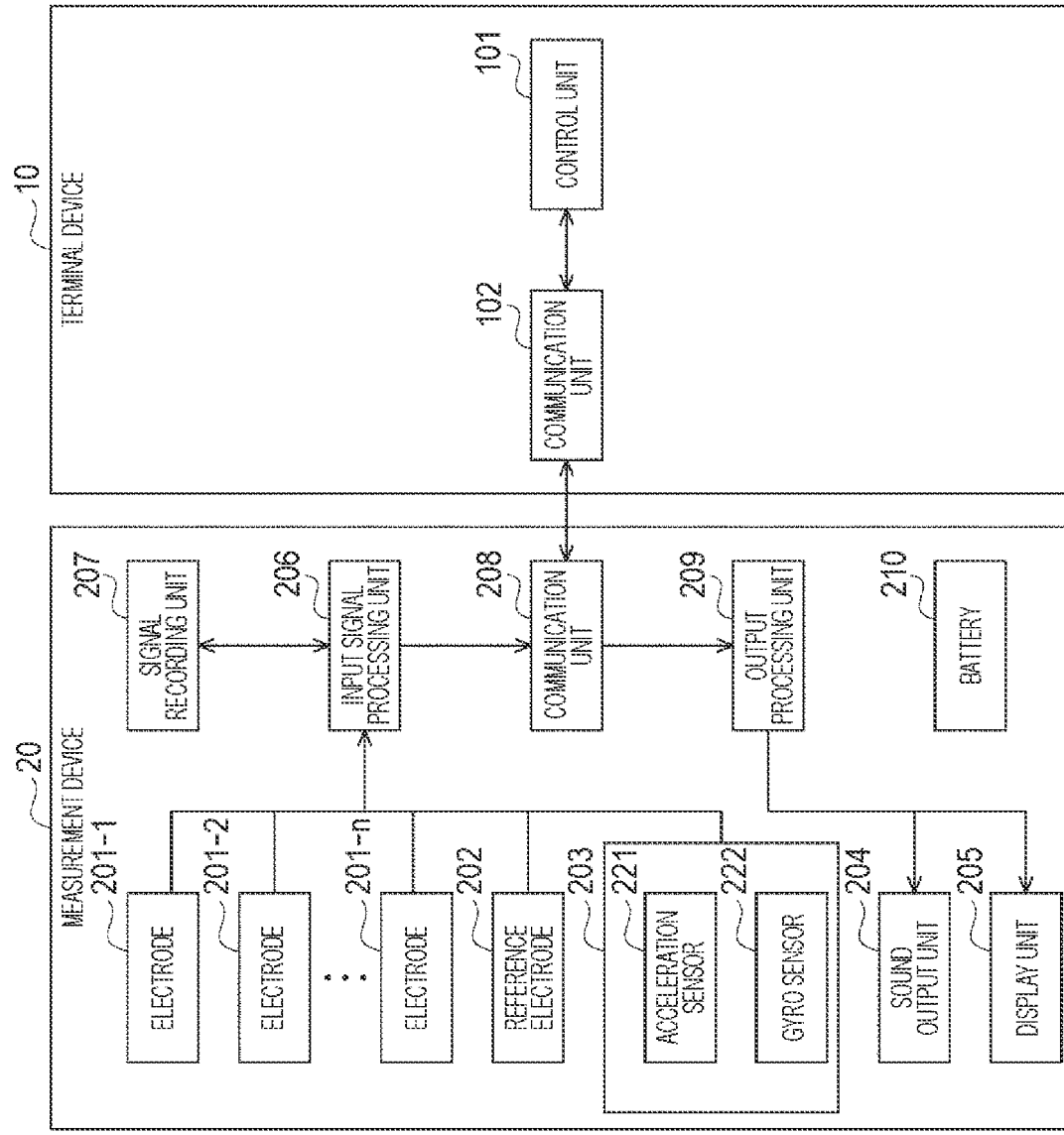
FIG. 13 is a block diagram illustrating a configuration example of an electroencephalogram system to which the present technology is applied.

FIG. 13 illustrates a configuration example of an electroencephalogram system to which the present technology is applied.

The electroencephalogram system is a system capable of providing various services using a brain wave signal measured from the head of the user. In FIG. 13, the electroencephalogram system includes a terminal device 10 and a measurement device 20.

The terminal device 10 is an electronic apparatus such as the mobile terminal 10A such as the above-described smartphone, a game machine, a controller, a personal computer (PC), a display device, or a portable music player. In FIG. 13, the terminal device 10 includes a control unit 101 and a communication unit 102.

The control unit 101 is a main control device that controls various operations and performs various types of arithmetic processing. The control unit 101 includes a processor such as a central processing unit (CPU). The control unit 101 can activate and execute the electroencephalogram application.

The communication unit 102 communicates with other devices such as the measurement device 20 under the control of the control unit 101. The communication unit 102 is configured as a communication module compatible with wireless communication or wired communication conforming to a predetermined communication scheme.

For example, the wireless communication includes wireless communication according to a short-distance wireless communication standard such as Bluetooth (registered trademark) or near field communication (NFC), wireless communication such as a wireless local area network (LAN), and cellular communication such as LTE-Advanced or a fifth generation (5G). In addition, the wired communication includes communication compatible with a communication interface such as a high definition multimedia interface (HDMI) (registered trademark).

The measurement device 20 is an electronic apparatus such as the earphone 20A described above, a head mounted display (HMD) 20B described below, and a wearable terminal such as a glasses-type wearable device.

In FIG. 13, the measurement device 20 includes electrodes 201-1 to 201-$n$ (n: an integer of one or more), a reference electrode 202, a sensor unit 203, a sound output unit 204, a display unit 205, an input signal processing unit 206, a signal recording unit 207, a communication unit 208, an output processing unit 209, and a battery 210.

The electrodes 201-1 to 201-$n$ are measurement electrodes that measure biometric signals. The reference electrode 202 is a reference electrode that measures a reference potential used for calculating a difference from the potentials measured by the electrodes 201-1 to 201-$n$.

The electrodes 201-1 to 201-$n$ and the reference electrode 202 are attached so as to be in close contact with parts such as the head and the ear of the user. The biometric signals measured by the electrodes 201-1 to 201-$n$ and the reference electrode 202 are supplied to the input signal processing unit 206.

The electrode may include a ground electrode. The ground electrode here is not a common ground electrode (electrode having a ground potential), but refers to an electrode having a potential serving as a reference potential for a user. In the following description, the electrodes 201-1 to 201-$n$ will be simply referred to as the electrode 201 in a case where it is not particularly necessary to distinguish them.

The sensor unit 203 performs sensing of space information, time information, and the like, and supplies a sensor signal obtained as a result of the sensing to the input signal processing unit 206. For example, the sensor unit 203 includes an acceleration sensor 221 and a gyro sensor 222.

The acceleration sensor 221 measures accelerations in three directions of the XYZ axes. The gyro sensor 222 measures angular velocities around three axes of the XYZ axes. Note that an inertial measurement unit (IMU) may be provided to measure a three-dimensional acceleration and an angular velocity with a three directions accelerometer and a three axes gyroscope.

The sound output unit 204 outputs a sound corresponding to the sound signal from the output processing unit 209. The sound output unit 204 includes a mechanism such as a driver unit constituting an earphone, a speaker, or the like.

The display unit 205 displays an image corresponding to the image signal from the output processing unit 209. The display unit 205 includes a panel unit such as a liquid crystal panel or an organic light emitting diode (OLED) panel, a signal processing unit, and the like.

The input signal processing unit 206 processes the biometric signals from the electrodes 201-1 to 201-$n$ and the reference electrode 202, and reads a myoelectric signal which is a weak signal generated in a nerve when a human moves a muscle or a brain wave signal which is a signal corresponding to electrical activity generated from a human brain.

The input signal processing unit 206 performs a predetermined signal process on the basis of the read myoelectric signal or the read brain wave signal. Note that the input signal processing unit 206 may use the sensor signal from the sensor unit 203 together with the myoelectric signal at the time of detecting the trigger action.

That is, the input signal processing unit 206 has a function as a detection unit that detects a brain wave included in the biometric signal of the user and detects a motion based on information (such as a myoelectric signal and a sensor signal) other than the brain wave included in the biometric signal. In addition, the input signal processing unit 206 has a function as a processing unit that performs the predetermined process based on brain wave.

The input signal processing unit 206 records data related to the read myoelectric signal or the read brain wave signal in the signal recording unit 207. The input signal processing unit 206 performs matching between the read myoelectric signal or the read brain wave signal and the myoelectric signal or brain wave signal recorded in the signal recording unit 207, and supplies data related to the matching result to the communication unit 208.

The signal recording unit 207 records data related to various signals under the control of the input signal processing unit 206. The signal recording unit 207 is configured as an auxiliary storage device such as a semiconductor memory. The signal recording unit 207 may be configured as an internal storage or may be an external storage such as a memory card.

The communication unit 208 communicates with another device such as the terminal device 10. The communication unit 208 transmits the data from the input signal processing unit 206 to the terminal device 10. In addition, the communication unit 208 receives data transmitted from the terminal device 10 and supplies the data to the output processing unit 209.

The communication unit 208 is configured as a communication module compatible with wireless communication or wired communication conforming to a predetermined communication scheme. For example, the wireless communication includes wireless communication according to a short-distance wireless communication standard such as Bluetooth (registered trademark), wireless communication such as a wireless LAN, and cellular communication such as LTE-Advanced or 5G. The wired communication includes communication compatible with a communication interface such as an HDMI (registered trademark).

The output processing unit 209 processes the data from the communication unit 208, supplies a sound signal to the sound output unit 204, and supplies an image signal to the display unit 205.

The battery 210 is detachably attached to the measurement device 20, and supplies power to each unit of the measurement device 20 via a predetermined terminal.

Note that the configuration illustrated in FIG. 13 is an example of the terminal device 10 and the measurement device 20, and the illustrated components may be removed or new components may be added.

For example, in the measurement device 20, there is a case where the sensor unit 203 including the acceleration sensor 221, the gyro sensor 222, and the like is not mounted. In addition, in a case where the measurement device 20 is the earphone 20A, the display unit 205 is not mounted. Furthermore, in a case where the measurement device 20 is an HMD 20B, the sound output unit 204 may not be mounted.

In addition, although the configuration of the terminal device 10 is the minimum configuration, an output processing unit, a sound output unit, a display unit, a signal recording unit, a battery, and the like may be provided as in the measurement device 20.

Arrangement Example of Electrodes

Figure 14:
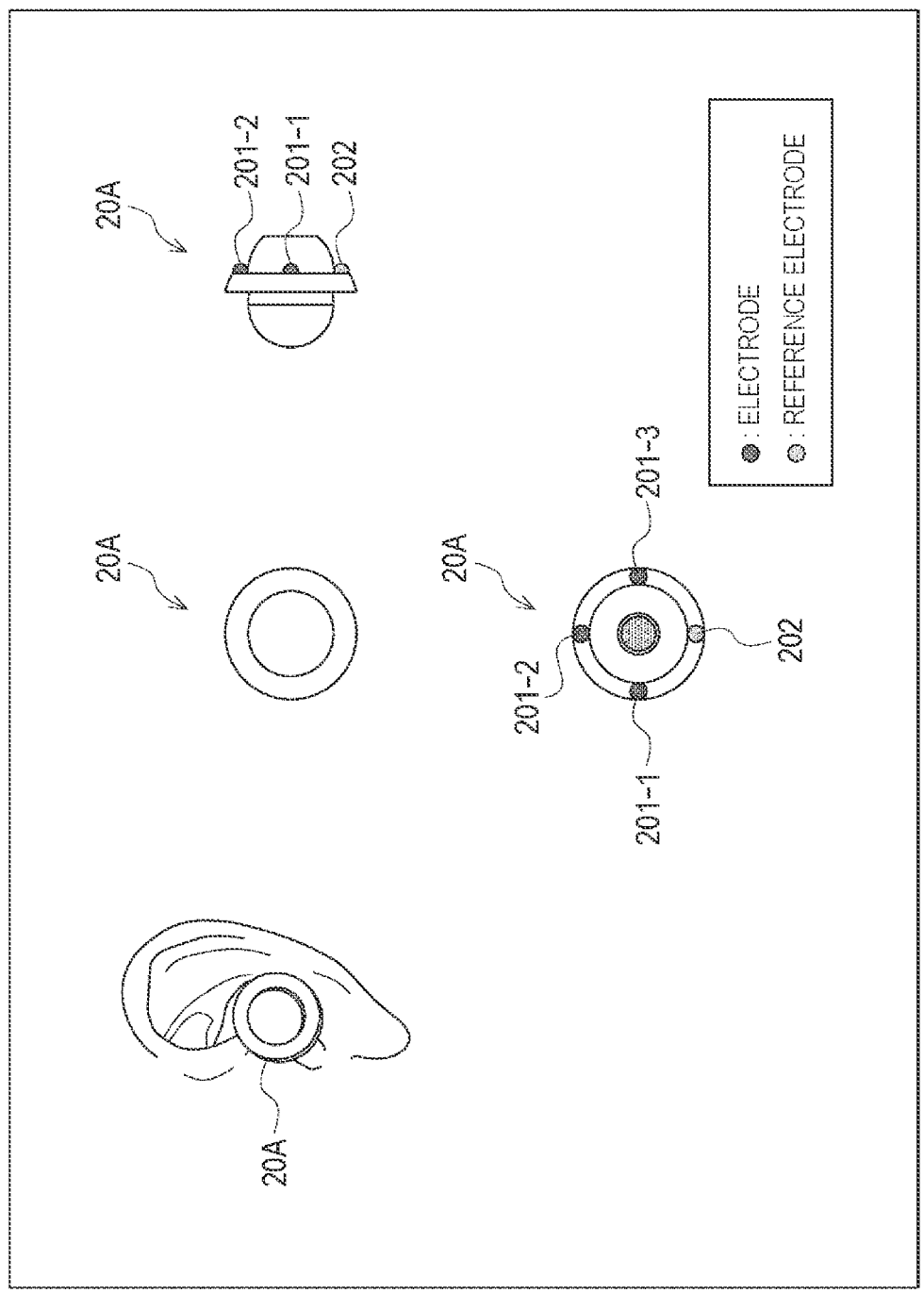
FIG. 14 is a view illustrating an arrangement example of an electrode and a reference electrode provided in an earphone.

FIG. 14 illustrates an arrangement example of the electrode 201 and the reference electrode 202 provided in the earphone 20A.

As illustrated in FIG. 14, in the earphone 20A, four electrodes of the electrodes 201-1 to 201-3 and the reference electrode 202 are disposed at substantially equal intervals on the same circumference around the portion that outputs a sound on the face in contact with the ear portion of the user, and the biometric signal of the user can be measured.

Figure 15:
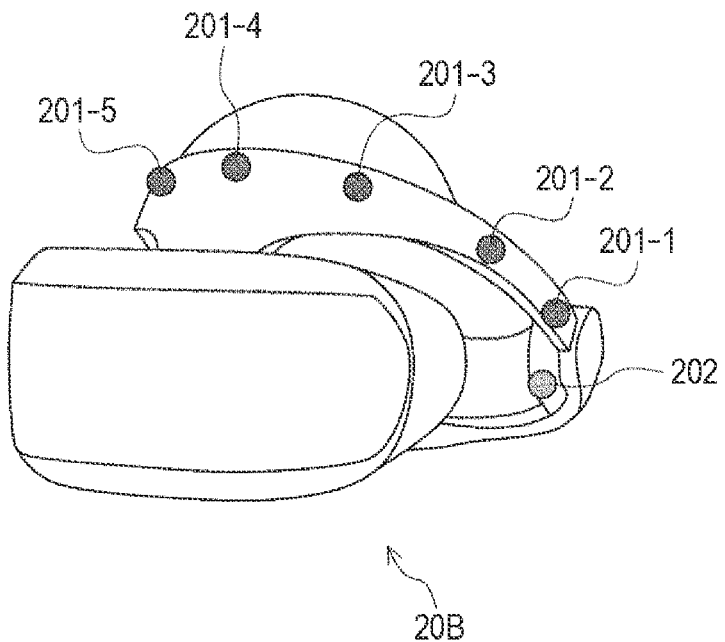
FIG. 15 is a view illustrating an arrangement example of an electrode and a reference electrode provided in an HMD.

FIG. 15 illustrates an arrangement example of the electrode 201 and the reference electrode 202 provided in the HMD 20B.

As illustrated in FIG. 15, in the HMD 20B, eight electrodes 201-1 to 201-8 are disposed at substantially equal intervals in a straight line on the face in contact with the forehead of the user, and the reference electrode 202 is disposed, away from the eight electrodes, at a predetermined position on the face in contact with the back of the head, and the biometric signal of the user can be measured.

Note that, in the perspective view of FIG. 15, among the electrodes 201-1 to 201-8, three sensors of the electrodes 201-6 to 201-8 are not illustrated because they are in blind spots. In addition, for convenience of explanation, the electrode 201 is illustrated to appear in the appearance of the HMD 20B, but is actually provided on the face in contact with the forehead of the user, that is, at a position not visible in the perspective view of FIG. 15.

Configuration Example of Table

Figure 16:
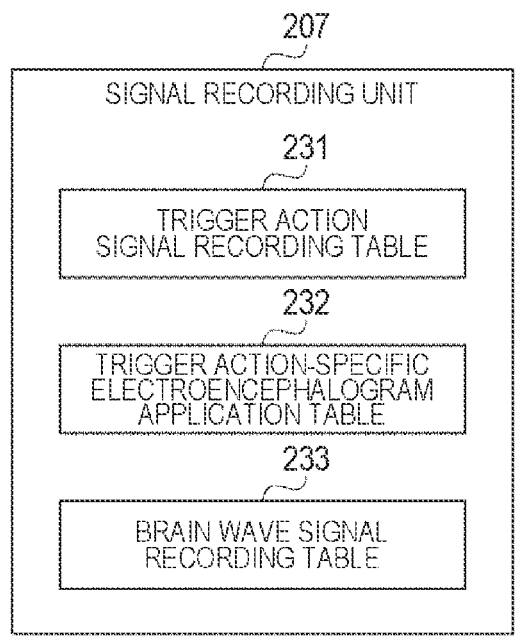
FIG. 16 is a diagram illustrating a configuration example of a table recorded in a signal recording unit.

FIG. 16 illustrates a configuration example of a table recorded in the signal recording unit 207 of FIG. 13.

The signal recording unit 207 records a trigger action signal recording table 231, a trigger action-specific electroencephalogram application table 232, and a brain wave signal recording table 233.

The trigger action signal recording table 231 is a table in which data of trigger action signals including a combination of head myoelectric potentials by parts such as the eyes, the jaw, and the neck of the user is recorded.

As illustrated in FIG. 17, in the trigger action signal recording table 231, the trigger action and the trigger action signal are recorded in association with each other.

For example, data of the myoelectric signal #1 is recorded as a trigger action signal of a trigger action (Trigger Action #1) that is eye closing, data of the myoelectric signal #2 is recorded as a trigger action signal of a trigger action (Trigger Action #2) that is blinking twice, and data of the myoelectric signal #3, the acceleration signal #1, and the angular velocity signal #1 are recorded as a trigger action signal of a trigger action (Trigger Action #3) that is eye closing after two blinks of both eyes with the neck down.

Note that a representative trigger action is eye closing, and the brain wave signal is read in a state where the user closes the eyes, but the brain wave signal may be read in a state where the eyes are opened, that is, the user opens the eyes. In the example of FIG. 17, only the data of the myoelectric signal is recorded as the trigger action signal for the trigger action of Trigger Action #1 and Trigger Action #2, but data indicating that the input values of the acceleration signal and the angular velocity signal are 0 (0 input value) may be recorded.

The trigger action-specific electroencephalogram application table 232 is a table in which the data of the electroencephalogram application for each trigger action recorded in the trigger action signal recording table 231 is recorded.

For example, as illustrated in FIG. 18, in the trigger action-specific electroencephalogram application table 232, Trigger Action #1 in FIG. 17 is associated with the electroencephalogram personal authentication application, and Trigger Action #2 in FIG. 17 is associated with the electroencephalogram search application.

The authentication in the electroencephalogram personal authentication application is not limited to the user's identity authentication. In addition, this electroencephalogram personal authentication may be applied to personal authentication implemented in Internet banking, Internet shopping, user selection at the time of viewing a content distributed via the Internet, an answer of a questionnaire via the Internet, a test or an interview using the Internet, or the like. Further, the present invention may be applied to personal authentication of a professional driver of a vehicle such as an automobile, an airplane, or a train.

The brain wave signal recording table 233 is a table in which data of a brain wave signal registered for each electroencephalogram application recorded in the trigger action-specific electroencephalogram application table 232 is recorded.

Figure 19:
FIG. 19 is a diagram illustrating an example of a brain wave signal recording table.

As illustrated in FIG. 19, in the brain wave signal recording table 233, an electroencephalogram application and a brain wave signal are recorded in association with each other.

For example, data such as the brain wave signal #11, the brain wave signal #12, and the brain wave signal #13 is recorded as the brain wave signal of the electroencephalogram personal authentication application, and data such as the brain wave signal #21, the brain wave signal #22, and the brain wave signal #23 is recorded as the brain wave signal of the electroencephalogram search application.

Another Configuration Example

Figure 20:
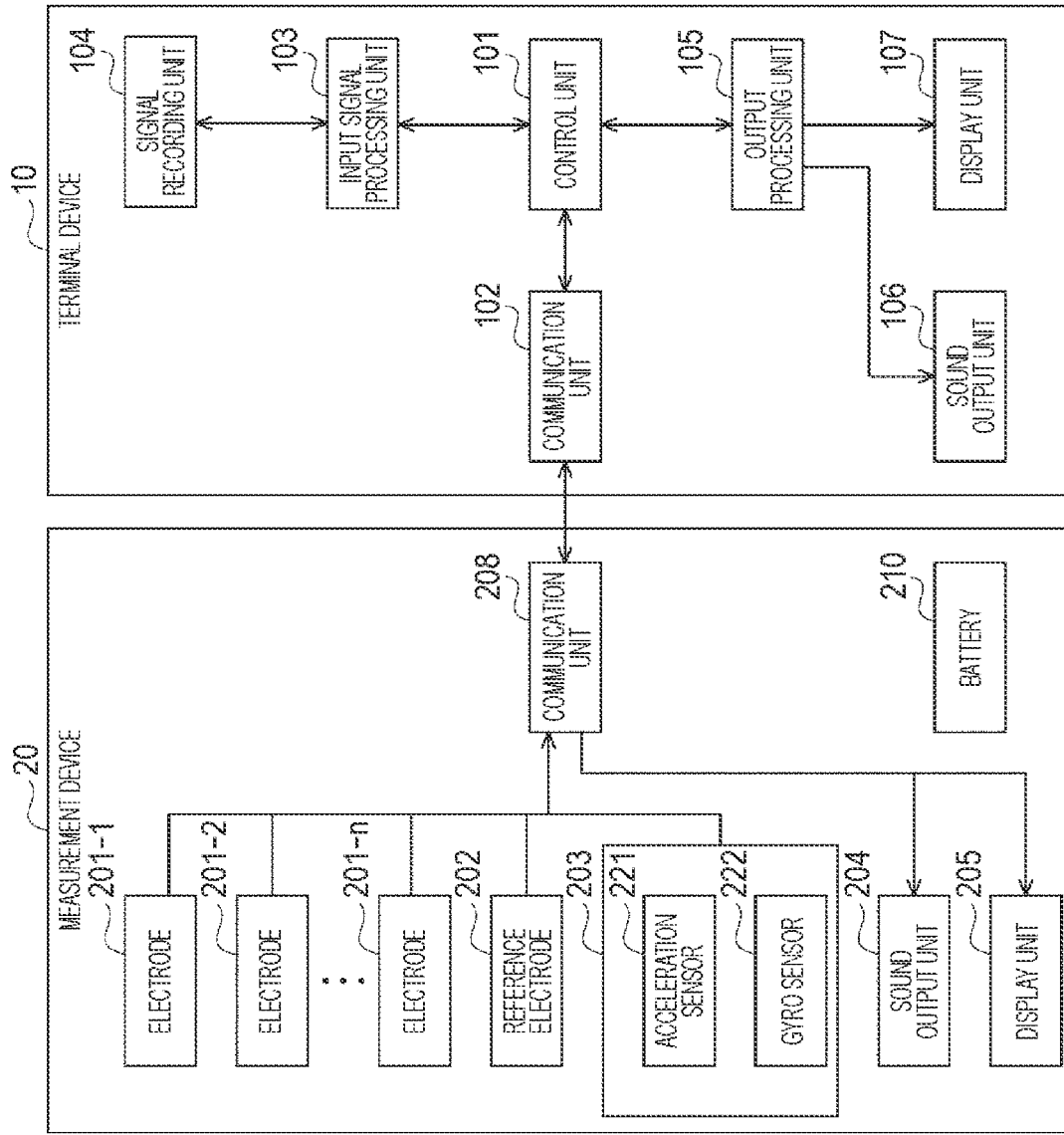
FIG. 20 is a block diagram illustrating another configuration example of the electroencephalogram system to which the present technology is applied.
Figure 21:
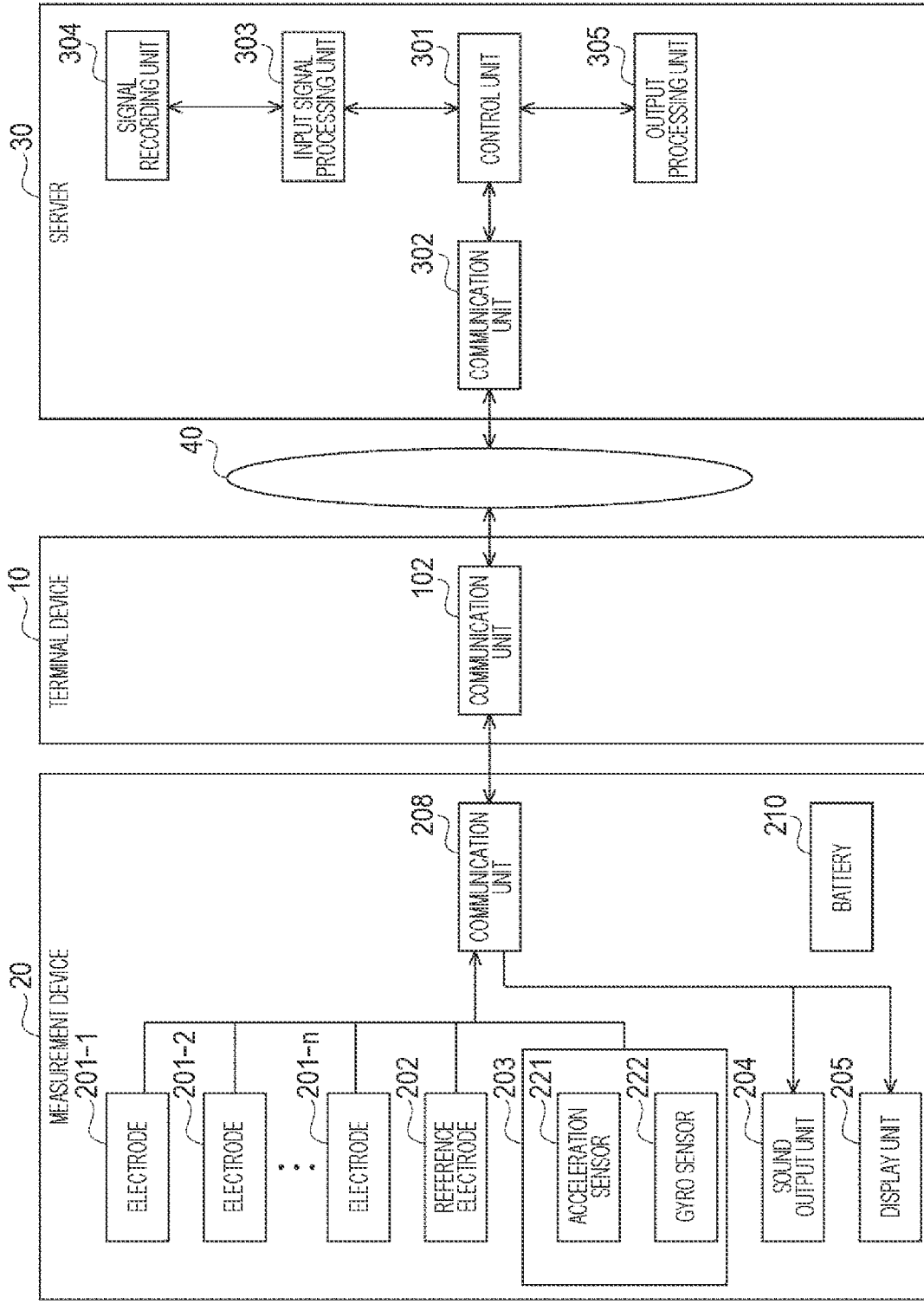
FIG. 21 is a block diagram illustrating another configuration example of the electroencephalogram system to which the present technology is applied.
Figure 22:
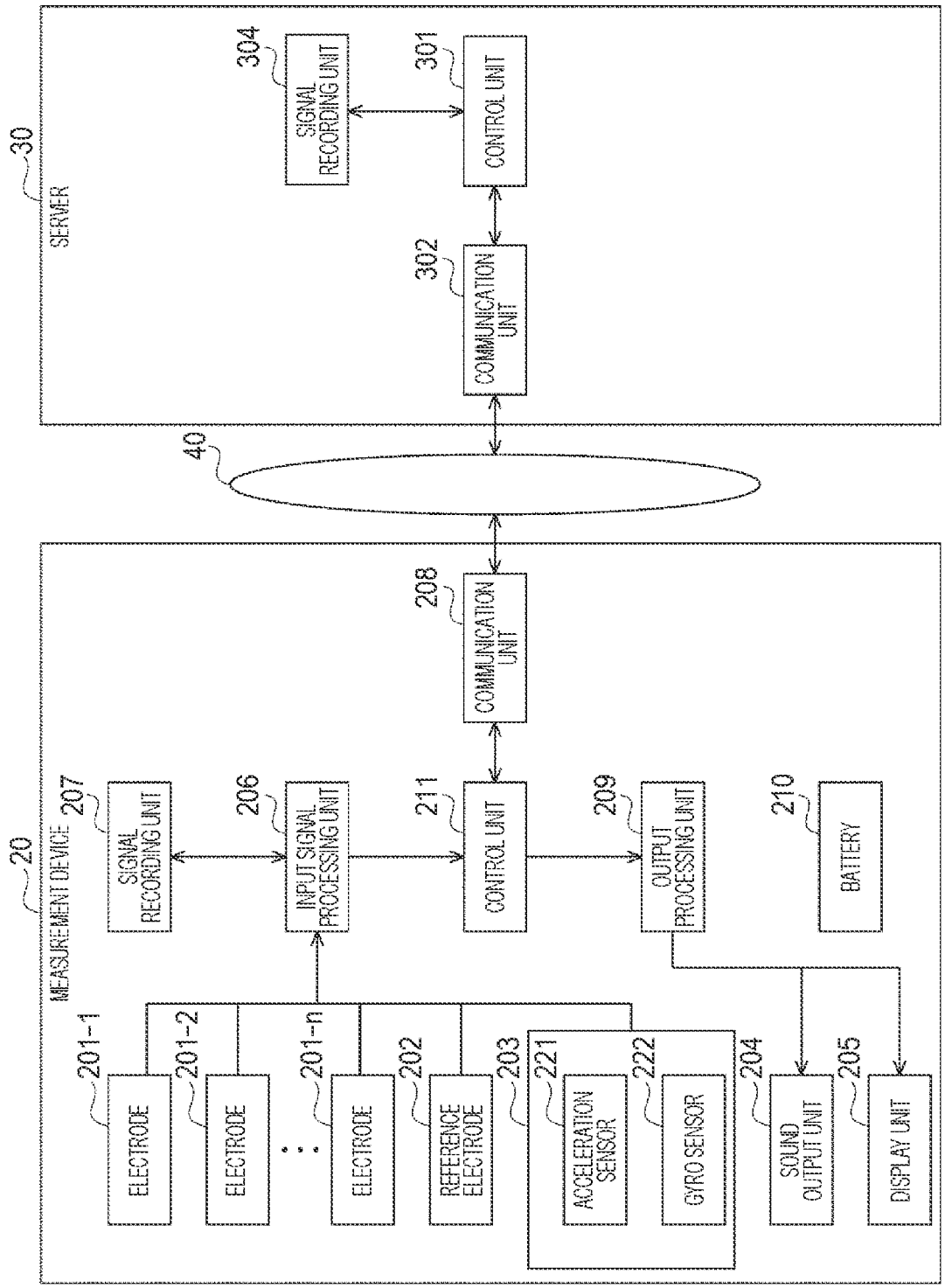
FIG. 22 is a block diagram illustrating another configuration example of the electroencephalogram system to which the present technology is applied.

FIGS. 20 to 22 illustrate other configuration examples of the electroencephalogram system to which the present technology is applied.

FIG. 20 illustrates a first example of another configuration of the electroencephalogram system to which the present technology is applied.

In FIG. 20, the electroencephalogram system includes the terminal device 10 and the measurement device 20. The same portions as those in the configuration example in FIG. 13 are denoted by the same reference numerals, and the description thereof will be omitted because it is repeated.

In FIG. 20, the terminal device 10 includes an input signal processing unit 103, a signal recording unit 104, an output processing unit 105, a sound output unit 106, and a display unit 107 in addition to the control unit 101 and the communication unit 102. The measurement device 20 includes the electrodes 201-1 to 201-n, the reference electrode 202, the sensor unit 203, the sound output unit 204, the display unit 205, the communication unit 208, and the battery 210.

That is, the configuration example of FIG. 20 is different from the configuration example of FIG. 13 in that the input signal processing unit 103, the signal recording unit 104, and the output processing unit 105 are provided in the terminal device 10 instead of the input signal processing unit 206, the signal recording unit 207, and the output processing unit 209 in the measurement device 20 in FIG. 13.

In the measurement device 20, the communication unit 208 transmits the biometric signals from the electrodes 201-1 to 201-n and the reference electrode 202 to the terminal device 10.

On the other hand, in the terminal device 10, the communication unit 102 receives the biometric signal transmitted from the measurement device 20 and supplies the biometric signal to the input signal processing unit 103 via the control unit 101.

The input signal processing unit 103 processes the biometric signal received by the communication unit 102, reads the myoelectric signal or the brain wave signal, and performs a predetermined signal process. The input signal processing unit 103 records data related to the read myoelectric signal or the read brain wave signal in the signal recording unit 104 such as a semiconductor memory.

The input signal processing unit 103 performs matching between the read myoelectric signal or the read brain wave signal and the myoelectric signal or brain wave signal recorded in the signal recording unit 104, and supplies data related to the matching result to the communication unit 102 or the output processing unit 105 via the control unit 101.

The output processing unit 105 processes the data from the input signal processing unit 103 and supplies the processed data to the communication unit 102. The communication unit 102 transmits the data from the control unit 101 to the measurement device 20. In the measurement device 20, the communication unit 208 receives data transmitted from the terminal device 10, supplies a sound signal to the sound output unit 204, and supplies an image signal to the display unit 205.

The sound output unit 204 outputs a sound corresponding to the sound signal from the communication unit 208. The display unit 205 displays an image corresponding to the image signal from the communication unit 208.

Note that the output processing unit 105 may process data input thereto, supply a sound signal to the sound output unit 106, and supply an image signal to the display unit 107. At this time, the sound output unit 106 outputs a sound corresponding to the sound signal from the output processing unit 105. In addition, the display unit 107 displays an image corresponding to the image signal from the output processing unit 105.

FIG. 21 illustrates a second example of another configuration of the electroencephalogram system to which the present technology is applied.

In FIG. 21, the electroencephalogram system includes the terminal device 10, the measurement device 20, and a server 30. In FIG. 21, the same components as those in the configuration example of FIG. 13 are denoted by the same reference numerals, and the description thereof will be omitted because it is redundant.

In FIG. 21, the terminal device 10 includes the communication unit 102. The measurement device 20 includes the electrodes 201-1 to 201-n, the reference electrode 202, the sensor unit 203, the sound output unit 204, the display unit 205, the communication unit 208, and the battery 210. The server 30 includes a control unit 301, a communication unit 302, an input signal processing unit 303, a signal recording unit 304, and an output processing unit 305.

That is, the configuration of FIG. 21 is different from the configuration example of FIG. 13 in that the input signal processing unit 303, the signal recording unit 304, and the output processing unit 305 are provided in the server 30 instead of the input signal processing unit 206, the signal recording unit 207, and the output processing unit 209 in the measurement device 20 in FIG. 13.

In the measurement device 20, the communication unit 208 transmits the biometric signals from the electrodes 201-1 to 201-*n* and the reference electrode 202 to the terminal device 10. In the terminal device 10, the communication unit 102 receives the biometric signal transmitted from the measurement device 20 to transmit the biometric signal to the server 30 via the network 40.

In the server 30, the communication unit 302 receives the biometric signal transmitted from the terminal device 10 and supplies the biometric signal to the input signal processing unit 303 via the control unit 301.

The input signal processing unit 303 processes the biometric signal received by the communication unit 302, reads the myoelectric signal or the brain wave signal, and performs the predetermined process. The input signal processing unit 303 records data related to the read myoelectric signal or the read brain wave signal in the signal recording unit 304 such as a semiconductor memory or a hard disk drive (HDD).

The input signal processing unit 303 performs matching between the read myoelectric signal or the read brain wave signal and the myoelectric signal or brain wave signal recorded in the signal recording unit 304, and supplies data related to the matching result to the communication unit 302 or the output processing unit 305 via the control unit 301.

The output processing unit 305 processes the data from the input signal processing unit 303 and supplies the processed data to the communication unit 302. The communication unit 302 transmits the data from the control unit 301 to the measurement device 20 via a network 40 and the terminal device 10. In the measurement device 20, the communication unit 208 receives data transmitted from the server 30, supplies a sound signal to the sound output unit 204, and supplies an image signal to the display unit 205.

The sound output unit 204 outputs a sound corresponding to the sound signal from the communication unit 208. The display unit 205 displays an image corresponding to the image signal from the communication unit 208.

The network 40 includes a communication network such as the Internet, an intranet, or a mobile phone network, and enables interconnection between devices using a communication protocol such as a transmission control protocol/internet protocol (TCP/IP).

FIG. 22 illustrates a third example of another configuration of the electroencephalogram system to which the present technology is applied.

In FIG. 22, the electroencephalogram system is configured by the measurement device 20 and the server 30. The same portions as those in the configuration examples of FIGS. 13 and 21 are denoted by the same reference numerals, and the description thereof will be omitted because it is repeated.

In FIG. 22, the measurement device 20 includes a control unit 211 in addition to the electrodes 201-1 to 201-*n*, the reference electrode 202, the sensor unit 203, the sound output unit 204, the display unit 205, the input signal processing unit 206, the signal recording unit 207, the communication unit 208, the output processing unit 209, and the battery 210. The server 30 includes the control unit 301, the communication unit 302, and the signal recording unit 304.

That is, the configuration of FIG. 22 is different from the configuration example of FIG. 13 in that (the control unit 101 of) the terminal device 10 is not provided, but the control unit 211 is provided in the measurement device 20, and the measurement device 20 also has the function of the terminal device 10.

In addition, the configuration of FIG. 22 is different from the configuration example of FIG. 21 in that only the signal recording unit 304 in addition to the control unit 301 and the communication unit 302 is provided in the server 30, and the server 30 operates as a database server on a cloud.

Although other configuration examples of the electroencephalogram system to which the present technology is applied have been described above, the configurations illustrated in FIGS. 20 to 22 are merely examples, and other configurations may be used. That is, in the electroencephalogram system, the input signal processing unit (103,206,303), the signal recording unit (104,207,304), and the output signal processing unit (105,209,305) may be provided in any of the terminal device 10, the measurement device 20, and the server 30.

In addition, the terminal device 10, the measurement device 20, and the server 30 can also be said to be control devices since functions of the input signal processing unit (103,206,303) and the output signal processing unit (105, 209,305) are each implemented by a processor such as a CPU executing a program.

(Flow of Processing)

Figure 23:
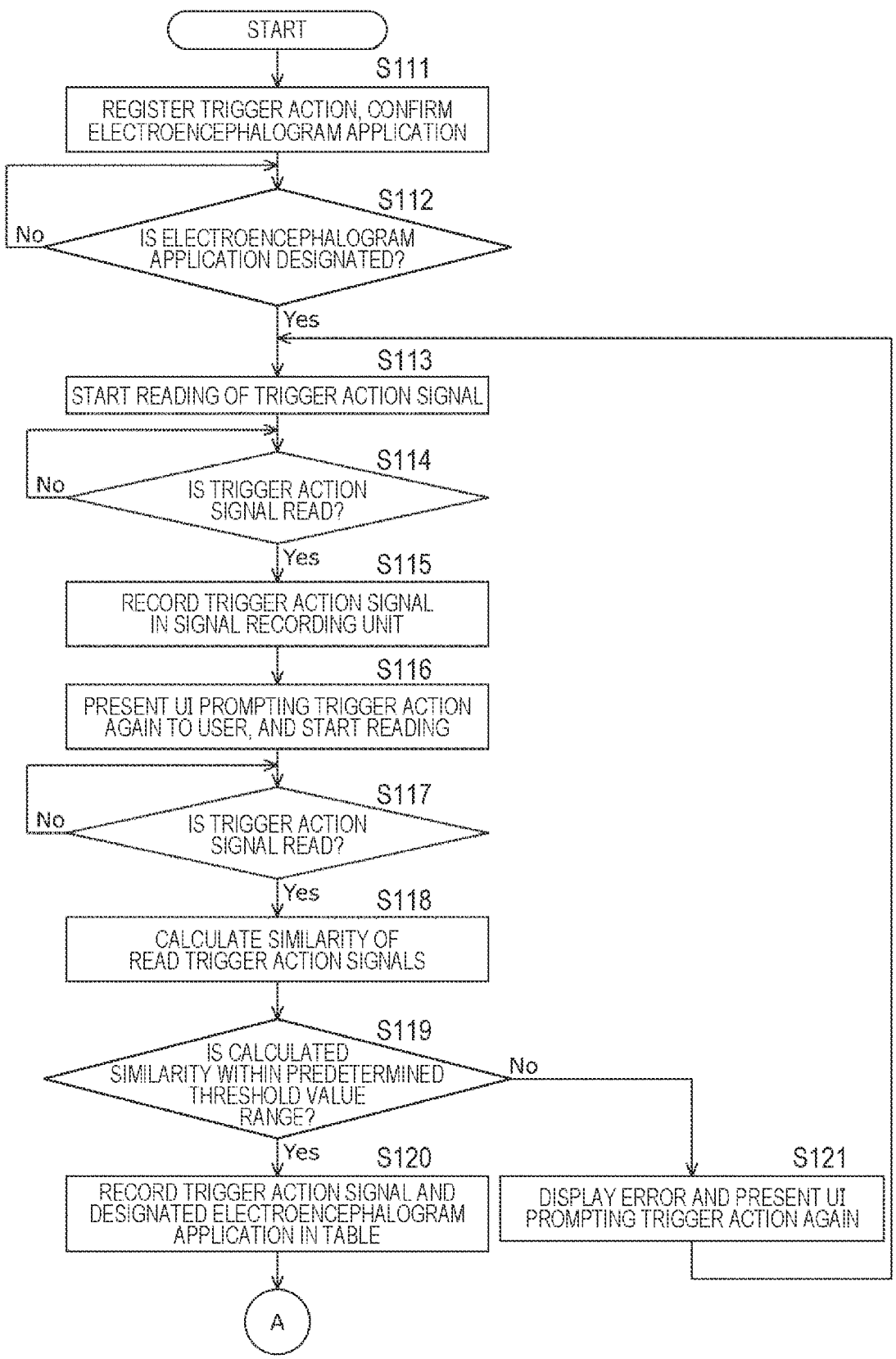
FIG. 23 is a flowchart illustrating a flow of a registration process of a trigger action and a pass-thought.

The registration process of the trigger action and the pass-thought will be described with reference to the flowcharts of FIGS. 23 and 24.

In this registration process, the terminal device 10 or the measurement device 20 confirms the electroencephalogram application for registering the trigger action with respect to the user (S111), and after designating the electroencephalogram application to be registered ("Yes" in S112), the process proceeds to step S113.

In step S113, the input signal processing unit 206 starts reading the trigger action signal detected as the myoelectric signal.

In step S114, the input signal processing unit 206 processes the biometric signal from the electrode 201 and the reference electrode 202, and determines whether the trigger action signal has been read. In the determination process of step S114, the process proceeds to step S115 after it is determined that the trigger action signal has been read.

In step S115, the input signal processing unit 206 records the read trigger action signal in the signal recording unit 207.

In step S116, the output processing unit 209 controls the sound output unit 204 or the display unit 205 to present a user interface (UI) prompting the trigger action again to the user, and the input signal processing unit 206 starts to read the trigger action signal.

In step S117, the input signal processing unit 206 processes the biometric signal from the electrode 201 and the reference electrode 202, and determines whether the trigger action signal has been read. In the determination process of step S117, the process proceeds to step S118 after it is determined that the trigger action signal has been read.

In step S118, the input signal processing unit 206 calculates a similarity between the trigger action signals read in the process of steps S114 and S117.

In step S119, the input signal processing unit 206 determines whether the calculated similarity of the trigger action signals falls within a predetermined threshold value range.

In a case where it is determined in the determination process of step S119 that the similarity falls within the predetermined threshold value range, the process proceeds to step S120. In step S120, the input signal processing unit 206 records the trigger action signal and the designated electroencephalogram application in the table of the signal recording unit 207.

For example, in the trigger action signal recording table 231 of FIG. 17, a myoelectric signal is recorded as a trigger action signal in association with a trigger action such as eye closing or blinking twice. In addition, in the trigger action-specific electroencephalogram application table 232 of FIG. 18, a designated electroencephalogram application such as an electroencephalogram personal authentication application is recorded in association with a trigger action such as eye closing or blinking twice.

On the other hand, in a case where it is determined in the determination process of step S119 that the similarity is out of the range of the predetermined threshold value, the process proceeds to step S121. In step S121, the output processing unit 209 controls the sound output unit 204 or the display unit 205, and presents a user interface (UI) prompting the trigger action again to the user. Then, the process returns to step S113, and the subsequent processes are repeated.

Figure 24:
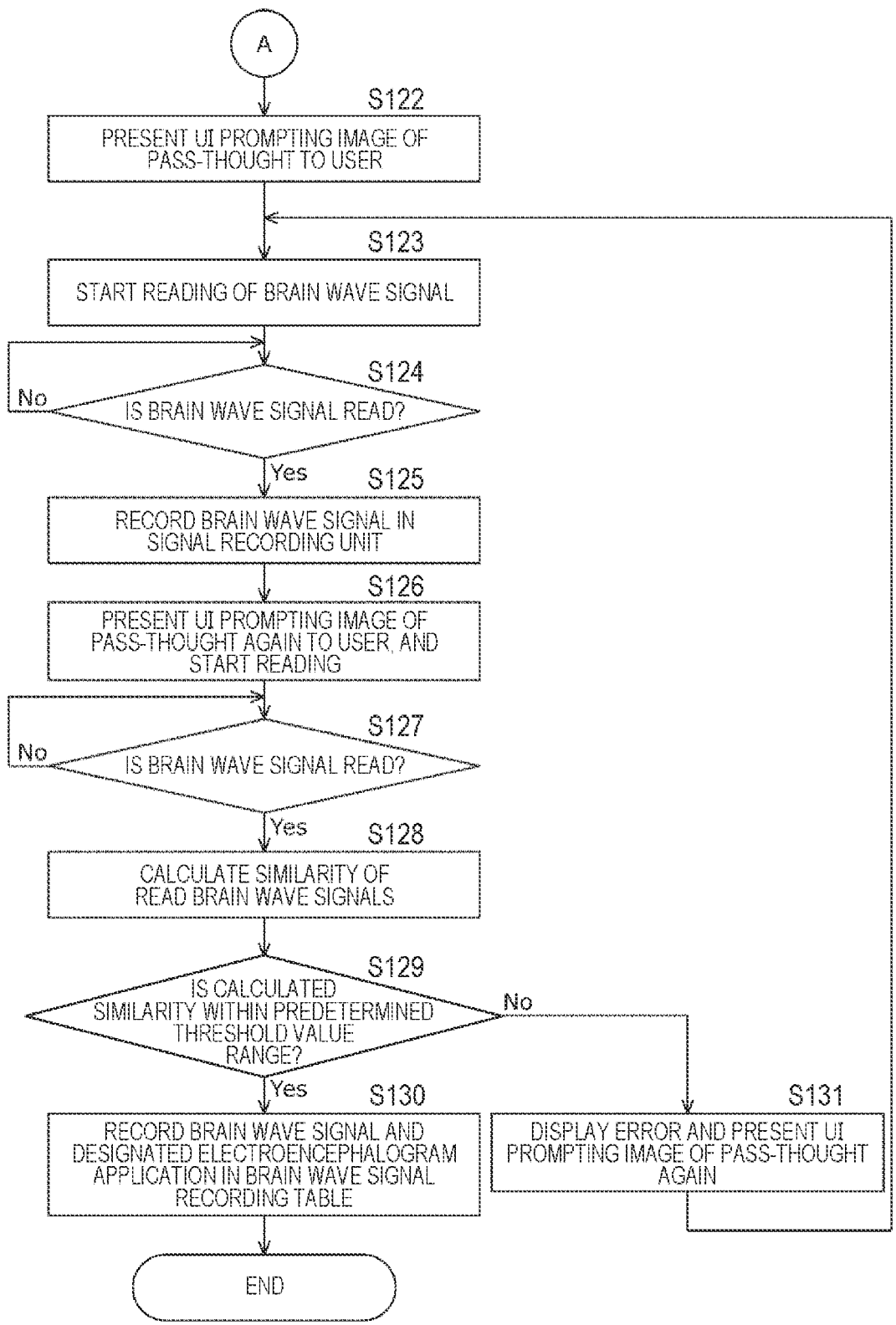
FIG. 24 is a flowchart illustrating a flow of a registration process of a trigger action and a pass-thought.

When the process of step S120 ends, the process proceeds to step S122 of FIG. 24. In step S122, the output processing unit 209 controls the sound output unit 204 or the display unit 205 to present a user interface (UI) prompting an image of a pass-thought.

In step S123, the input signal processing unit 206 starts reading the brain wave signal.

In step S124, the input signal processing unit 206 processes the biometric signal from the electrode 201 and the reference electrode 202, and determines whether the brain wave signal has been read. In the determination process of step S124, the process proceeds to step S125 after it is determined that the brain wave signal has been read.

In step S125, the input signal processing unit 206 records the read brain wave signal in the signal recording unit 207.

In step S126, the output processing unit 209 controls the sound output unit 204 or the display unit 205 to present the user with a user interface (UI) that prompts an image of the pass-thought again, and the input signal processing unit 206 starts to read the brain wave signal.

In step S127, the input signal processing unit 206 processes the biometric signal from the electrode 201 and the reference electrode 202, and determines whether the brain wave signal has been read. In the determination process of step S127, the process proceeds to step S128 after it is determined that the brain wave signal has been read.

In step S128, the input signal processing unit 206 calculates a similarity of the brain wave signals read by the process in steps S124 and S127.

In step S129, the input signal processing unit 206 determines whether the calculated similarity of the brain wave signals falls within a predetermined threshold value range.

In a case where it is determined in the determination process of step S129 that the similarity falls within the predetermined threshold value range, the process proceeds to step S130. In step S130, the input signal processing unit 206 records the brain wave signal and the designated electroencephalogram application in the brain wave signal recording table 233.

For example, in the brain wave signal recording table 233 of FIG. 19, a brain wave signal is recorded in association with a designated electroencephalogram application such as an electroencephalogram personal authentication application.

On the other hand, in a case where it is determined in the determination process of step S129 that the similarity is out of the range of the predetermined threshold value, the process proceeds to step S131. In step S131, the output processing unit 209 controls the sound output unit 204 or the display unit 205 to present the user with a user interface (UI) that prompts the image of a pass-thought again. Then, the process returns to step S123, and the subsequent processes are repeated.

When the process of step S130 ends, the registration process of the trigger action and the pass-thought ends.

Figure 25:
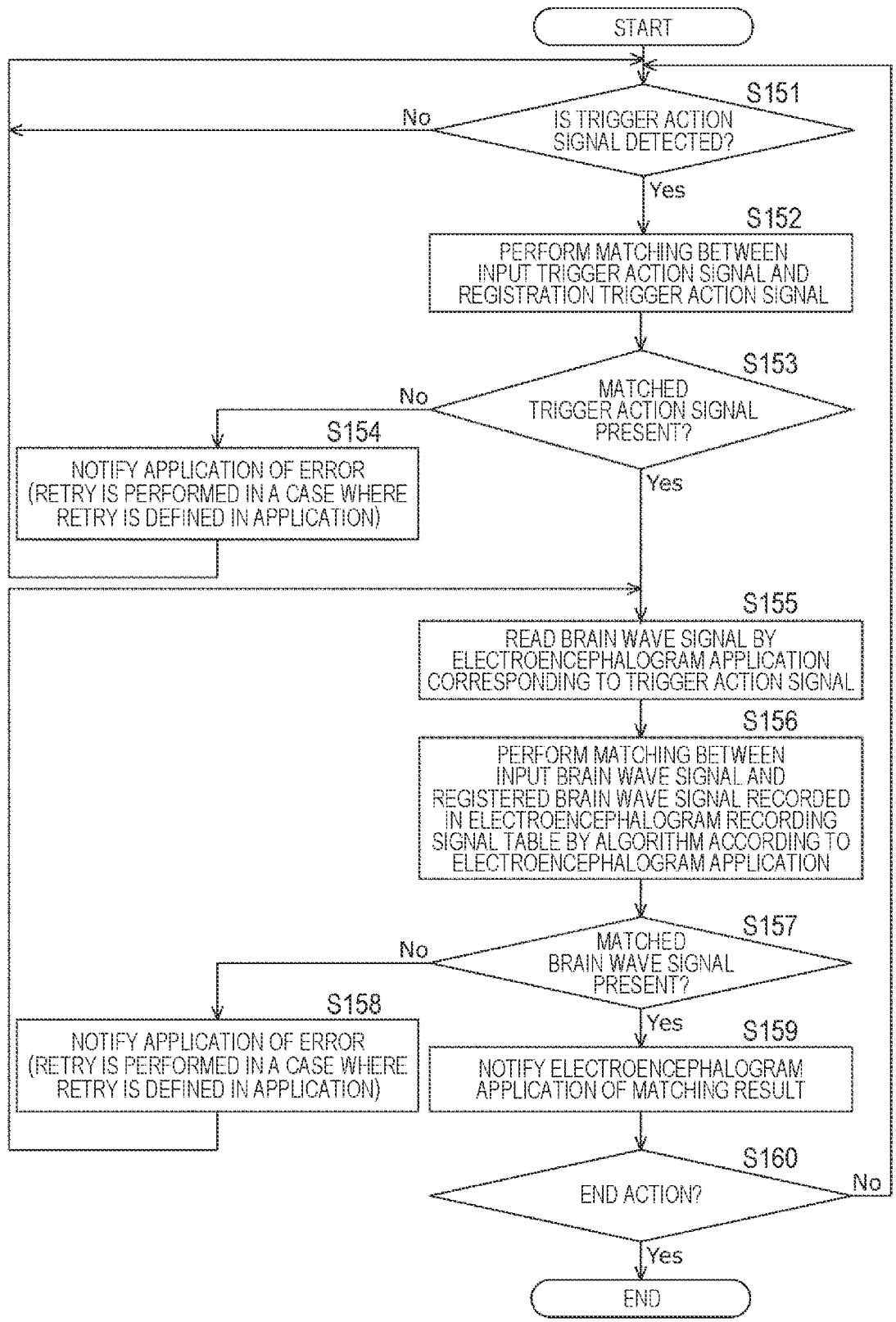
FIG. 25 is a flowchart illustrating a flow of an electroencephalogram personal authentication process.

Next, the personal electroencephalogram authentication process will be described with reference to the flowchart of FIG. 25.

In step S151, the input signal processing unit 206 determines whether a trigger action signal has been detected as a myoelectric signal on the basis of the biometric signals from the electrode 201 and the reference electrode 202. In the determination process of step S151, the process proceeds to step S152 after detecting the trigger action signal.

In step S152, the input signal processing unit 206 performs matching between the input trigger action signal and the registration trigger action signal with reference to the trigger action signal recording table 231 of the signal recording unit 207.

In step S153, the input signal processing unit 206 determines whether there is a matched trigger action signal on the basis of the matching result of the trigger action signal.

In a case where it is determined in the determination process of step S153 that there is no matched trigger action signal, the process proceeds to step S154. In step S154, notification of an error is provided to the electroencephalogram application executed by the terminal device 10 or the measurement device 20.

Note that, in a case where retry is defined by the electroencephalogram application, the process returns to step S151, the subsequent processes are repeated, and matching of the trigger action signal is retried.

On the other hand, in a case where it is determined in the determination process of step S153 that there is a matched trigger action signal, the process proceeds to step S155. In step S155, the input signal processing unit 206 reads the brain wave signal by the electroencephalogram application corresponding to the trigger action.

In step S156, the input signal processing unit 206 performs matching between the input brain wave signal and the registered brain wave signal recorded in the brain wave signal recording table 233 by an algorithm according to the corresponding electroencephalogram application.

In step S157, the input signal processing unit 206 determines whether there is a matched brain wave signal on the basis of the matching result of the brain wave signal.

In a case where it is determined in the determination process of step S157 that there is no matched brain wave signal, the process proceeds to step S158. In step S158, notification of an error is provided to the electroencephalogram application executed by the terminal device 10 or the measurement device 20.

Note that, in a case where retry is defined by the electroencephalogram application, the process returns to step S155, the subsequent processes are repeated, and the matching of the brain wave signal is retried.

On the other hand, in a case where it is determined in the process of step S157 that there is a matched brain wave signal, the process proceeds to step S159. In step S159, notification of the matching result is provided to the electroencephalogram application executed by the terminal device 10 or the measurement device 20. As a result, in the terminal device 10 or the measurement device 20, the electroencephalogram application executes various types of processing according to the matching result.

In step S160, it is determined whether to end the action. In a case where it is determined in the determination process of step S160 that the action is not to be ended, the process returns to step S151, and the subsequent processes are repeated. In addition, in a case where it is determined in the determination process of step S160 that the action is to be ended, the personal electroencephalogram authentication process is ended.

As the trigger action described above, a response of an event-related potential (ERP) may be used. In a case where the event-related potential is used as the trigger action, for example, the following sequence (S91 to S94) is obtained.

(1) An event inducing the event-related potential is presented (S91).

(2) Generation of the event-related potential in the user's brain wave is identified as a trigger action (S92).

(3) An instruction or the like for the pass-thought is presented (S93).

(4) Processing related to the pass-thought or the like is performed on the basis of a waveform of a brain wave of the user for presentation of an instruction or the like (S94).

In step S91, as the presentation of the event, for example, generation of a specific sound, presentation of a human face, presentation that induces a sense of discomfort, or the like is performed. These presentations correspond to types of event-related potentials. The event-related potential includes, for example, N170 in which a brain wave response occurs after about 170 milliseconds for recognition of a face, MMN regarding acoustic deviation for auditory stimulation, P300 in which a brain wave response occurs after about 300 milliseconds from recognition of an event causing unnatural or uncomfortable feeling, and N400 in which a brain wave response occurs after about 400 milliseconds from recognition of deviation in meaning in language.

Since the event-related potentials such as N170, MMN, P300, and N400 are generated by the presentation of the event, the generation of the event-related potential is recognized as the trigger action in step S92.

That is, in a case where the user is conscious of the presentation event, the event-related potential serving as the trigger action is generated, but in a case where the user is not conscious of the presentation event, the event-related potential does not occur, and the event-related potential does not serve as the trigger action.

This can be understood as, for example, depending on whether or not the user pays attention to the object content, and in a case where the user does not pay attention, such as looking at another content, a response of the event-related potential does not occur. This is effective in a case where the user pays attention to the object content and wants to perform processing related to the subsequent pass-thought. Conversely, in a case where the user does not pay attention to the object content, such processing can be suppressed in a case where the user does not want to perform the processing related to the subsequent pass-thought.

In addition, by using the response of the event-related potential, the processing can be performed by completing the brain wave of the user even when there is not an explicit action of the user such as blinking. For example, the subsequent processing can be performed only by embedding the event that induces the event-related potential as the trigger action so as not to be conspicuous (casually) in the object content without an explicit instruction.

As in steps S24, S25 to S26 (FIG. 6) described above, in steps S93 and S94, processing such as a pass-thought recognition process is performed on the basis of the waveform of the user's brain wave for the presentation of the instruction or the like.

Note that, in the above description, an example in which a user-specific response including an event-related potential is used is described. However, this is electroencephalogram acquisition for performing the process related to the pass-thought or the like, and description made here is different from an example described above, and is not for acquiring the brain wave of the user for a process related to the pass-thought or the like, but an example in which an event-related potential of the brain wave of the user is used as a trigger action.

As described above, the measurement device 20 includes the electrode 201, the reference electrode 202, and the sensor unit 203 including the acceleration sensor 221 and the gyro sensor 222 in order to read the brain wave signal and the myoelectric signal from the head of the user, and records the trigger action (any combination of movements of both eyelids, eyeballs, a jaw, and the like of the user and a movement of the head) for each electroencephalogram application using the brain wave, and the user selectively uses the trigger action, so that reading of the brain wave signal immediately after the trigger action is performed only for the corresponding electroencephalogram application. Therefore, the convenience and accuracy of the user interface by the electroencephalogram input can be improved.

For example, in a case where the trigger action is "eye closing" and the electroencephalogram application is "electroencephalogram personal authentication application", it is possible to naturally transition from the action of closing the eyes to the electroencephalogram measurement with less artifact by using the head myoelectric potential generated when the user closes the eyes as a trigger. Specifically, with this flow, the user can naturally perform the resting state and the action as a series of flows.

That is, in the present technology, the action of the user is detected on the basis of the myoelectric signal (information other than a brain wave) which is a biometric signal having a larger variation range of the potential difference than the brain wave signal measured from the user, and in a case where the action of the user is a predetermined action, the predetermined process based on the brain wave signal measured from the user is performed. Therefore, a more convenient electroencephalogram input user interface can be provided. In addition, it is possible to realize processing related to brain waves such as electroencephalogram personal authentication having a natural user interface that is easy for all people to understand. Note that the artifact is so-called noise at the time of measuring a biometric signal such as a brain wave signal or a myoelectric signal.

In general, the myoelectric signal of the head used for the trigger action is larger than the brain wave signal and is characteristic. Therefore, in the measurement device 20, it is possible to contribute to low power consumption by performing operation in the trigger action measurement mode at the normal time and setting the time resolution and the amplification factor of the signal amplifier at the time of reading the myoelectric signal to be lower than those at the time of reading the brain wave signal in the electroencephalogram measurement mode.

2. Second Embodiment

The biometric personal authentication is personal authentication performed using information regarding a physical feature or a behavioral feature of an individual as a key for personal authentication. Normally, in this type of personal authentication, first, key information is registered on the basis of biometric information about the user at the time of registration, and then, at the time of authentication, the biometric information about the user is acquired, matching it with the biometric authentication that has been originally registered is performed, and a process of permitting authentication is performed in a case where there is a certain level of correlation or greater.

A specific brain wave for a specific stimulus such as hearing or vision is referred to as an event-related potential, and various studies have been conducted. As described above, N170, MMN, P300, N400, and the like are known as the event-related potentials.

In addition, authentication can be performed by detecting waveforms of these event-related potentials and, in addition, response components peculiar to the user. For example, in a case where a sound or a video for giving a stimulus to the user is used as an induction medium, a user individually outputs a characteristic and unique response brain wave for a specific induction medium, so that there is electroencephalogram personal authentication for authenticating an individual by performing matching it with a past response brain wave.

Various techniques have been proposed as personal authentication techniques using event-related potentials. However, in the current technology, since the personal authentication is performed on the basis of the registration result of the brain wave at the event-related potential performed for the first time, there remains a risk of spoofing in a case where the information about the induction medium and the response brain wave leaks to the outside due to hacking or the like.

Therefore, in the present technology, the induction medium is generated randomly with unpredictable contents, and the above-described authentication and registration process is continuously performed in a form compatible with the service, so that the security is enhanced while changing the induction medium, and the risk of spoofing due to leakage of confidential information such as a key is reduced. Hereinafter, a second embodiment will be described with reference to the drawings.

First Example

Figure 26:
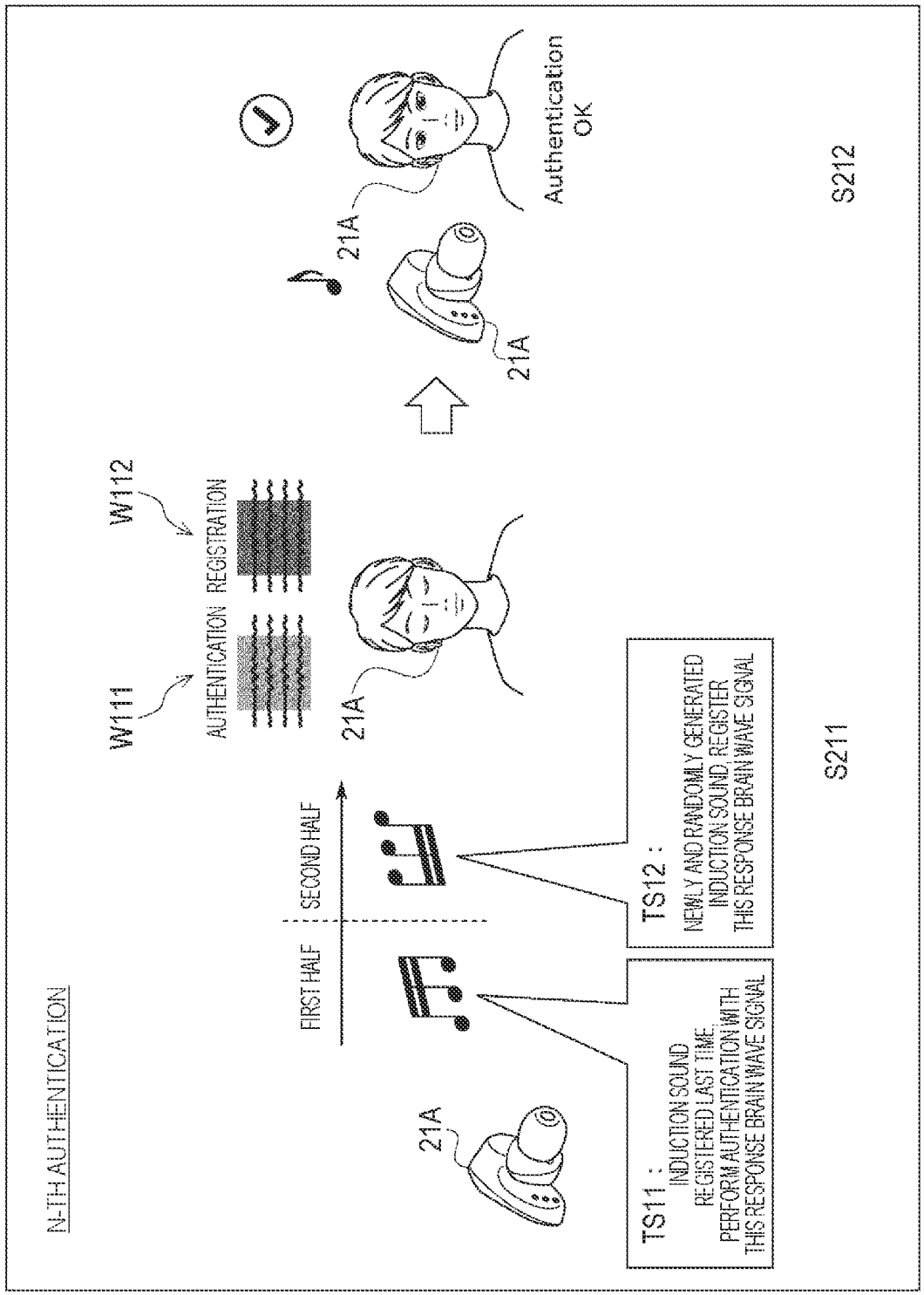
FIG. 26 is a diagram illustrating an authentication registration example of personal authentication using auditory induction.
Figure 27:
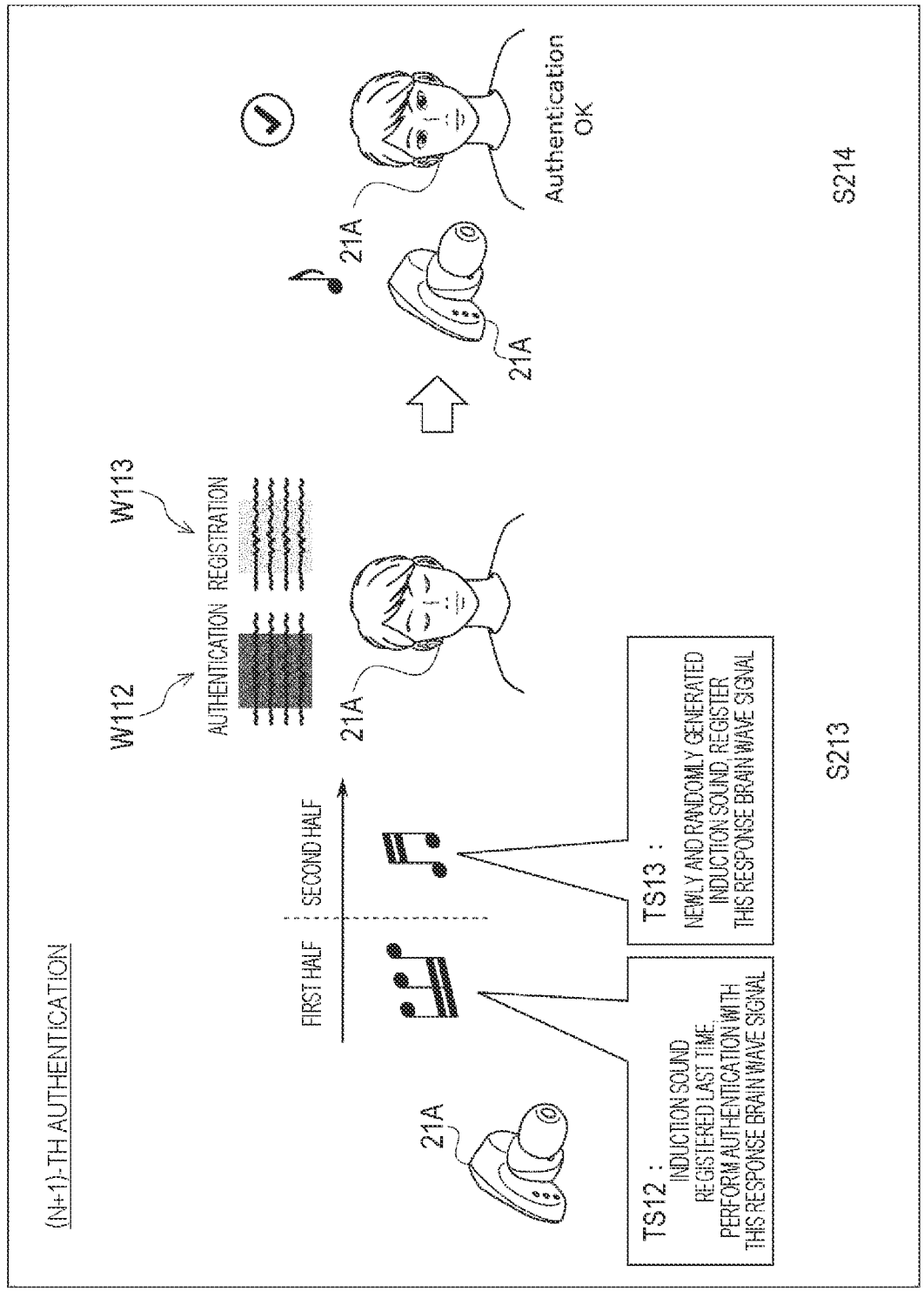
FIG. 27 is a diagram illustrating an authentication registration example of personal authentication using auditory induction.

FIGS. 26 and 27 illustrate an authentication registration example of electroencephalogram personal authentication using auditory induction.

In FIGS. 26 and 27, the user wears on the ear an earphone 21A connected to a mobile terminal 11A such as a smartphone in a wireless or wired manner. The earphone 21A is provided with a plurality of electrodes, and can measure a brain wave signal from the head of the user.

Although details will be described later, an fNIRS signal measured by a measurement method applying the principle of optical functional imaging in which brain functions are non-invasively mapped from the scalp using near-infrared light, which is referred to as functional near-infrared spectroscopy (fNIRS), may be measured. That is, cerebral blood flow information measured using a measurement method for measuring a cerebral blood flow such as fNIRS may be used in addition to the brain wave signal as brain wave information. Examples of a method for measuring a cerebral blood flow include NIRS and MRI, fNIRS is included in NIRS, and fMRI is included in MRI. In the following description, a case where fNIRS is used will be described as an example of a method of measuring a cerebral blood flow.

FIG. 26 illustrates an authentication registration example of N-th (N: an integer of one or more) electroencephalogram personal authentication.

When an induction sound is output from the earphone 21A, and the user responds to the auditory induction by the induction sound, a brain wave signal corresponding to the response is measured (S211).

At this time, different sounds are output in the first half and the second half of the induction sound. That is, the induction sound is a combination of the registered sound and the new sound, and a different combination of sounds is replayed each time.

The first half induction sound TS11 is an induction sound in which a brain wave signal is registered last time ((N−1)-th time), and the current (N-th) authentication is performed using a brain wave signal corresponding to a response of the user to the induction sound. The second half induction sound TS12 is an induction sound that is newly and randomly generated, and a brain wave signal corresponding to a response of the user to the induction sound is registered for use in the next ((N+1)-th) authentication. Note that the induction sound TS12 is not limited to a newly randomly generated induction sound, and may be replayed by randomly selecting an induction sound generated in advance.

In this example, the brain wave signal for authentication including a waveform W111 corresponding to the induction sound TS11 and the brain wave signal for registration including a waveform W112 corresponding to the induction sound TS12 are measured, and the authentication process and the registration process are started.

In the authentication process, matching is performed as to whether the waveform W111 of the brain wave signal for authentication (input brain wave signal) has a similarity within a predetermined threshold value range with the waveform of the brain wave signal (registered brain wave signal) recorded in the previous registration process, and in a case where there is a matched brain wave signal, the user is authenticated as a valid user. In the registration process, the brain wave signal for registration including the waveform W112 is recorded for use in the next authentication process.

When the authentication using the induction sound is completed, a sound (authentication clear sound) or the like indicating that the authentication is completed is output from the earphone 21A to the user (S212).

FIG. 27 illustrates an authentication registration example of the (N+1)-th electroencephalogram personal authentication.

When an induction sound is output from the earphone 21A and the user responds to the auditory induction, a brain wave signal corresponding to the response is measured. A combination of the (N+1)-th induction sounds is different from the combination of the above-described N-th induction sounds (S213).

That is, the first half induction sound TS12 is an induction sound in which a brain wave signal is registered last time (N-th time), and the current ((N+1)-th) authentication is performed using the brain wave signal corresponding to the response of the user to the induction sound. The second half induction sound TS13 is an induction sound that is newly and randomly generated, and a brain wave signal corresponding to a response of the user to the induction sound is registered for use in the next ((N+2)-th) authentication.

In this example, the brain wave signal for authentication including the waveform W112 corresponding to the induction sound TS12 and the brain wave signal for registration including a waveform W113 corresponding to the induction sound TS13 are measured, and the authentication process and the registration process are started.

In the authentication process, matching is performed as to whether the waveform W112 of the brain wave signal for authentication (input brain wave signal) has a similarity within a predetermined threshold value range with the waveform of the brain wave signal (registered brain wave signal) recorded in the previous registration process, and in a case where there is a matched brain wave signal, the user is authenticated as a valid user. In the registration process, the brain wave signal for registration including the waveform W113 is recorded for use in the next authentication process.

When the authentication using the induction sound is completed, a sound (authentication clear sound) or the like indicating that the authentication is completed is output from the earphone 21A to the user (S214).

In this way, it is possible to perform authentication with further enhanced security by continuously performing authentication using the brain wave signal corresponding to the auditory induction response by the induction sound by changing the combination of the induction sounds such as by performing authentication using the registered brain wave signal registered at the time of the previous ((N−1)-th) authentication and the input brain wave signal measured at the time of the current (N-th) authentication, and further performing authentication using the registered brain wave signal registered at the time of the current (N-th) authentication and the input brain wave signal measured at the time of the next ((N+1)-th) authentication.

Second Example

Figure 28:
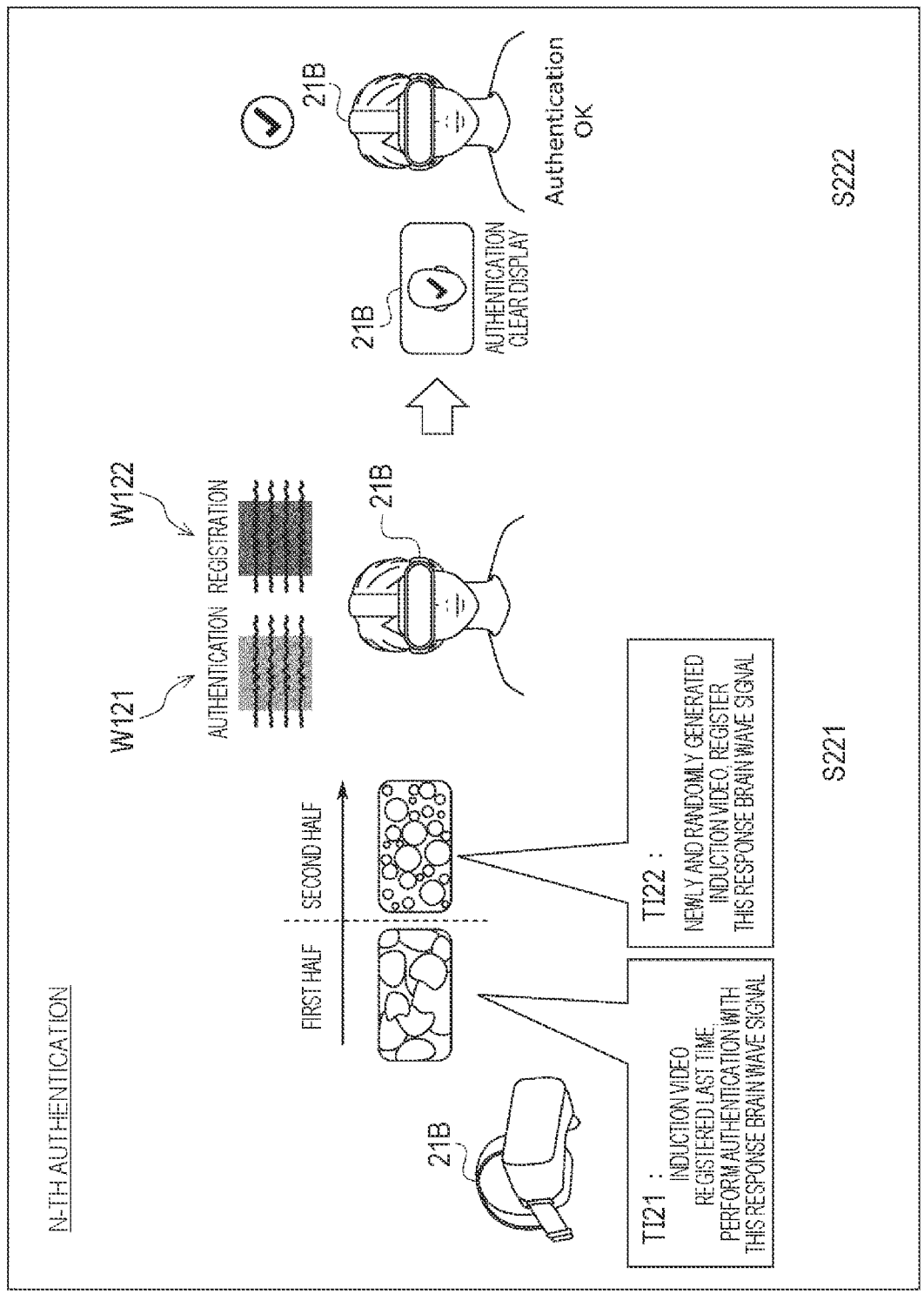
FIG. 28 is a diagram illustrating an authentication registration example of personal authentication using visual induction.
Figure 29:
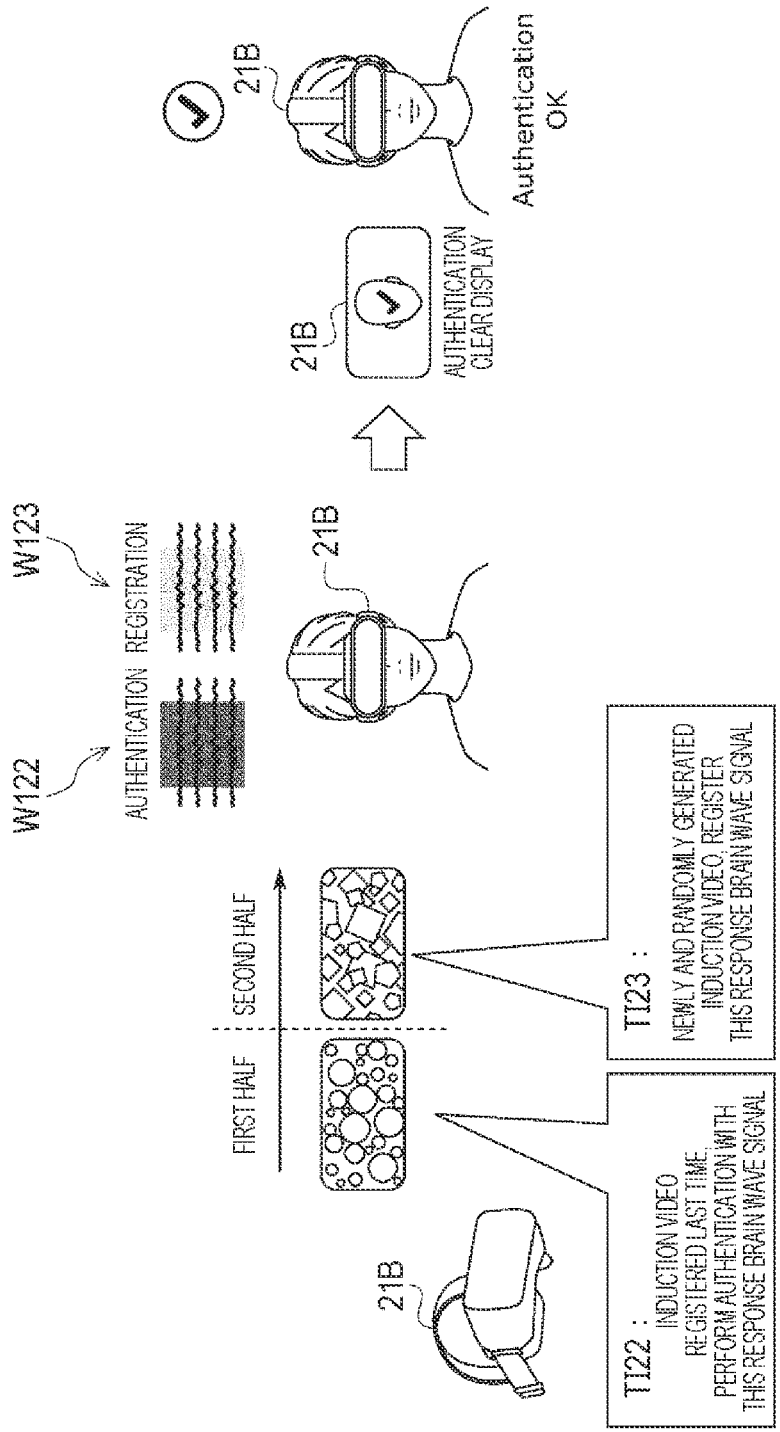
FIG. 29 is a diagram illustrating an authentication registration example of personal authentication using visual induction.

FIGS. 28 and 29 illustrate an authentication registration example of electroencephalogram personal authentication using visual induction.

In FIGS. 28 and 29, the user wears on the head an HMD 21B connected to a terminal device 11 such as a game machine in a wireless or wired manner. The HMD 21B is provided with a plurality of electrodes, and can measure a brain wave signal from the head of the user. Note that an fNIRS signal may be measured instead of the brain wave signal.

FIG. 28 illustrates an authentication registration example of the N-th electroencephalogram personal authentication.

When an induction video is displayed on the display of the HMD 21B and the user responds to visual induction by the induction video, a brain wave signal corresponding to the response is measured (S221).

At this time, different videos are displayed in the first half and the second half of the induction video. That is, the induction video is a combination of the registered video and the new video, a different combination of videos is replayed each time.

The first half induction video TI21 is an induction video in which a brain wave signal is registered last time ((N−1)-th time), and the current (N-th) authentication is performed using the brain wave signal corresponding to the response of the user to the induction video. The second half induction video TI22 is an induction video newly and randomly generated, and a brain wave signal corresponding to a response of the user to the induction video is registered for use in the next ((N+1)-th) authentication.

In this example, the brain wave signal for authentication including a waveform W121 corresponding to the induction video TI21 and the brain wave signal for registration including a waveform W122 corresponding to the induction video TI22 are measured, and the authentication process and the registration process are started.

In the authentication process, matching is performed as to whether the waveform W121 of the brain wave signal for authentication (input brain wave signal) has a similarity within a predetermined threshold value range with the waveform of the brain wave signal (registered brain wave signal) recorded in the previous authentication process, and in a case where there is a matched brain wave signal, the user is authenticated as a valid user. In the registration process, the brain wave signal for registration including the waveform W122 is recorded for use in the next authentication process.

When the authentication by the induction video is completed, a video (authentication clear video) or the like indicating that the authentication is completed are displayed on the display of the HMD 21B for the user (S222).

FIG. 29 illustrates an authentication registration example of the (N+1)-th electroencephalogram personal authentication.

When an induction video is displayed on the display of the HMD 21B and the user responds to this visual induction, a brain wave signal corresponding to the response is measured, but a combination of the (N+1)-th induction videos is different from the above-described combination of the N-th induction videos (S223).

That is, the first half induction video TI22 is an induction video in which the brain wave signal is registered last time (N-th time), and the current ((N+1)-th) authentication is performed using the brain wave signal corresponding to the response of the user to the induction video. The second half induction video TI23 is an induction video newly and randomly generated, and a brain wave signal corresponding to a response of the user to the induction video is registered for use in the next ((N+2)-th) authentication.

In this example, the brain wave signal for authentication including the waveform W122 corresponding to the induction video TI22 and the brain wave signal for registration including a waveform W123 corresponding to the induction video TI23 are measured, and the authentication process and the registration process are started.

In the authentication process, matching is performed as to whether the waveform W122 of the brain wave signal for authentication (input brain wave signal) has a similarity within a predetermined threshold value range with the waveform of the brain wave signal (registered brain wave signal) recorded in the previous registration process, and in a case where there is a matched brain wave signal, the user is authenticated as a valid user. In the registration process, the brain wave signal for registration including the waveform W123 is recorded for use in the next authentication process.

When the authentication by the induction video is completed, a video (authentication clear video) indicating that the authentication is completed is displayed on the display of the HMD 21B for the user for the user (S224).

In this way, it is possible to perform authentication with further enhanced security by continuously performing authentication using the brain wave signal corresponding to the visual induction response by the induction video by changing the combination of the induction videos such as by performing authentication using the registered brain wave signal registered at the time of the previous ((N−1)-th) authentication and the input brain wave signal measured at the time of the current (N-th) authentication, and further performing authentication using the registered brain wave signal registered at the time of the current (N-th) authentication and the input brain wave signal measured at the time of the next ((N+1)-th) authentication.

Note that, in the description of FIGS. 26 and 27 and FIGS. 28 and 29, the example using the brain wave signal is described above, but, as described above, an fNIRS signal may be used. In this case, the "brain wave signal" described above may be replaced with the "fNIRS signal". The brain wave signal and the fNIRS signal are examples of brain information. In addition, it is possible to perform the electroencephalogram personal authentication for each electroencephalogram application.

Application Example of Content

By inserting an induction medium such as an induction sound or an induction video into a content provided by a music distribution service, a game, or the like, continuous personal authentication and registration can be performed.

Figure 30:
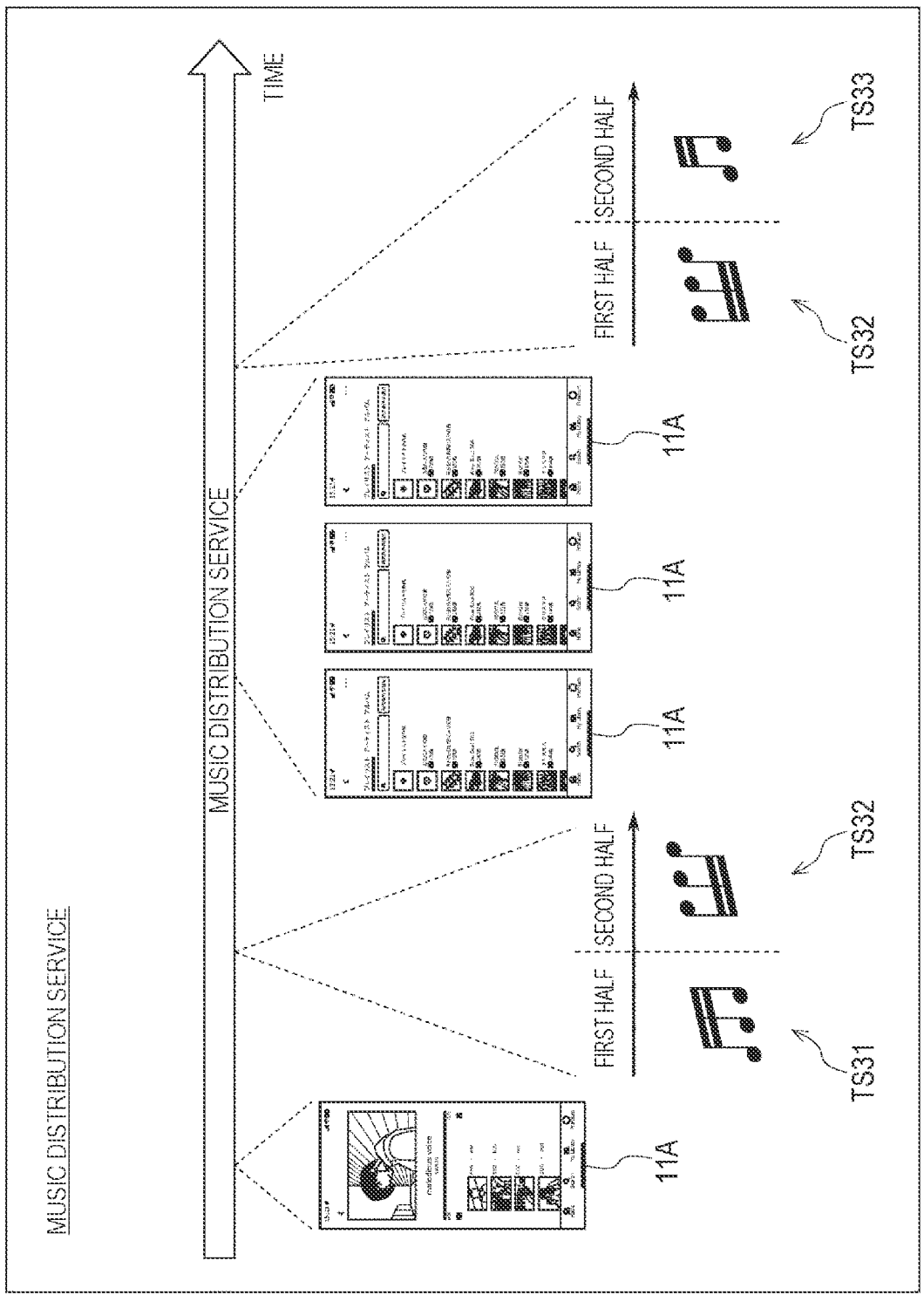
FIG. 30 is a diagram illustrating an application example of a music distribution service.

FIG. 30 illustrates an application example of a music content distributed by a music distribution service. In FIG. 30, screens of a music application displayed on the display of the mobile terminal 11A such as a smartphone or a mobile music player are illustrated in time series.

In FIG. 30, it is possible to perform authentication using the brain wave signal according to the response of the user by the auditory induction by including the induction sound between the music and the music or in the operation sound according to the operation of the user in a case where the user wearing the earphone 21A is listening to the music content replayed by the mobile terminal 11A. Furthermore, the induction sound may be inserted at the time of selecting, purchasing, downloading, or the like of the music content.

In this example, as a combination of the N-th induction sounds replayed between the pieces of music, the first half induction sound TS31 is an induction sound registered last time ((N−1)-th time), and the current (N-th) authentication is performed using the brain wave signal corresponding to the response of the induction sound. The second half induction sound TS32 is a newly generated induction sound, and a brain wave signal corresponding to a response of the induction sound is registered for use in the next ((N+1)-th) authentication.

Thereafter, as a combination of the (N+1)-th induction sounds included in the operation sound according to the user's operation, the first half induction sound TS32 is an induction sound registered last time (N-th time), and the current ((N+1)-th) authentication is performed using the brain wave signal according to the response of the induction sound. The second half induction sound TS33 is a newly generated induction sound, and a brain wave signal corresponding to a response of the induction sound is registered for use in the next ((N+2)-th) authentication.

As described above, during the replay of the music content, the induction sound is replayed with the expression that fits the music content and does not give a feeling of strangeness, so that the user can continuously perform the personal authentication and the registration of the authentication brain wave without being conscious. As a result, for example, it is possible for the provider of the music distribution service to appropriately authenticate the user who is viewing the music content.

Figure 31:
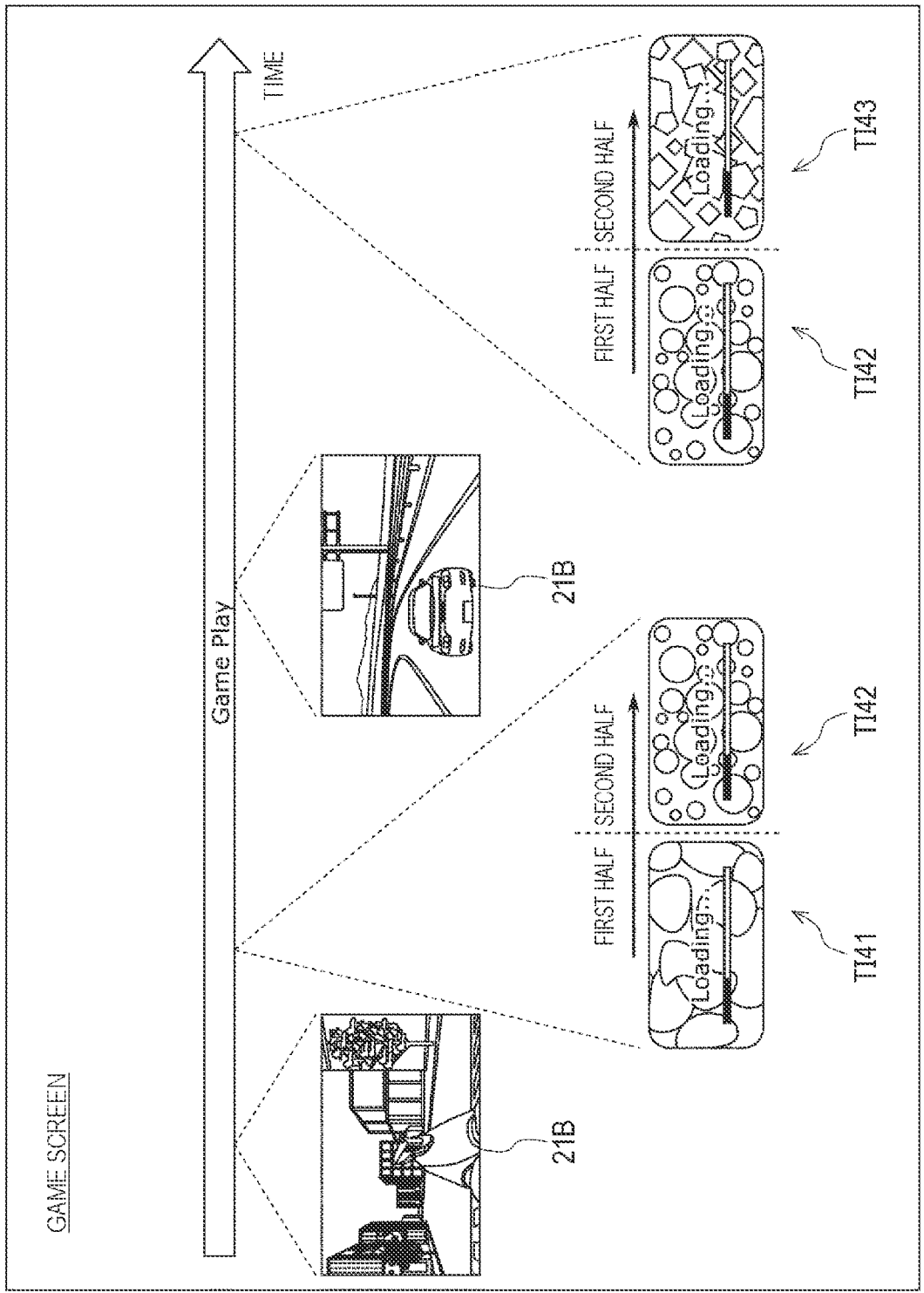
FIG. 31 is a diagram illustrating an application example of a game screen.

FIG. 31 illustrates an application example of the game content. In FIG. 31, game screens displayed on the display of the HMD 21B are illustrated in time series.

In FIG. 31, it is possible to perform the authentication using the brain wave signal corresponding to the user's response by the visual induction by including the induction video in a screen on which a scene of a game screen is being switched, and in a loading screen at the time of data reading or the like in a case where the user wearing the HMD 21B on the head is viewing the game content displayed on the display of the HMD 21B.

In this example, as a combination of the N-th induction videos included in a certain loading screen, the first half induction video TI41 is an induction video registered last time ((N−1)-th time), and the current (N-th) authentication is performed using the brain wave signal corresponding to the response of the induction video. The second half induction video TI42 is a newly generated induction video, and a brain wave signal corresponding to a response of the induction video is registered for use in the next ((N+1)-th) authentication.

Thereafter, as a combination of the (N+1)-th induction videos included in the next and subsequent loading screens, the first half induction video TI42 is an induction video registered last time (N-th time), and the current ((N+1)-th) authentication is performed using the brain wave signal corresponding to the response of the induction video. The second half induction video 1143 is a newly generated induction video, and a brain wave signal corresponding to a response of the induction video is registered for use in the next ((N+2)-th) authentication.

As described above, during the play of the game content, the induction video is displayed with the expression that fits the game content and does not give a feeling of strangeness, so that the user can continuously perform the personal authentication and the registration of the authentication brain wave without being conscious. As a result, for example, it is possible for the provider of the game content to appropriately perform authentication for the user playing the game content.

In a screen presented in a game content, an online service, or the like, a loading screen, a user selection screen, or the like is often included in the content. By reproducing the induction medium such as the induction video as the background of the function display and options of these screens, the processes of the electroencephalogram personal authentication and registration can be performed without the user's consciousness. Application examples of such a screen are illustrated in FIGS. 32 to 34.

Figure 32:
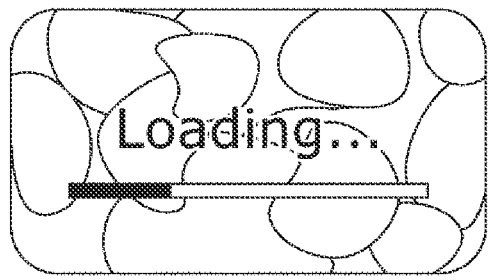
FIG. 32 is a diagram illustrating an application example of a loading screen.

FIG. 32 illustrates an application example of the loading screen. FIG. 32 illustrates an example in which in a case where a loading screen is displayed in the game content or the online service, the screen including the induction video TI51 is displayed. In this example, the induction video TI51 is displayed as the background of the text indicating the progress of loading and the progress bar.

Figure 33:
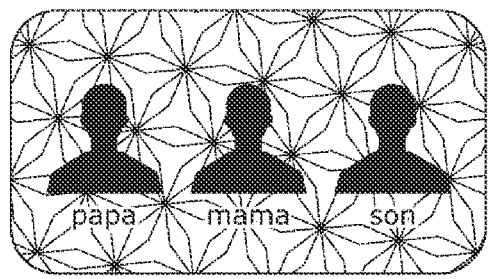
FIG. 33 is a diagram illustrating an application example of a user selection screen.

FIG. 33 illustrates an application example of the user selection screen. FIG. 33 illustrates an example in which in a case where a user selection screen is displayed in the game content or the online service, the screen including the induction video TI61 is displayed. In this example, the induction video TI61 is displayed as the background of the selectable icons corresponding to the three users.

Figure 34:
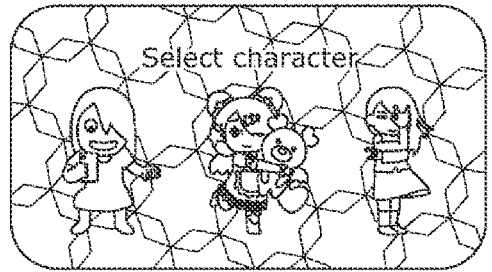
FIG. 34 is a diagram illustrating an application example of a user selection screen.

FIG. 34 illustrates an application example of the user selection screen. FIG. 34 illustrates an example in which in a case where a user selection screen is displayed in the game content, the screen including the induction video TI71 is displayed. In this example, the induction video TI71 is displayed as the background of the selectable characters corresponding to the three users.

Note that, in the above description, the HMD 21B has been exemplified as the device that executes the game content, but the induction video may be displayed on a screen of a television receiver connected to the game machine, a screen of a portable game machine, or a screen of a display device. The game content can include various contents such as, for example, a virtual reality (VR) content and an augmented reality (AR) content in addition to a 2D content and a 3D content.

As described above, the induction medium is information for inducing and measuring the user's brain information according to the replay. The induction medium includes an induction sound, an induction video, or the like, and is provided together with, for example, a distribution content (music content, game content, or the like) distributed by a content distribution service (music distribution service, Internet radio, podcast, game distribution service, and the like).

This providing method may include distributing the data of the induction sound or the induction video as data of one type of content constituting the distribution content (distributing data of a music content or a game content as another type), or inserting the data into data of the replay content constituting the distribution content (inserting the data between music and music, an operation sound according to user's operation, or the like). However, in the case of providing it as the one type of content, the data of the induction sound or the induction video may be generated by the device such as the mobile terminal 11A or the HMD 21B. Alternatively, the data of the induction sound or the induction video may be added (for example, added in a superimposed manner to the beginning or end of the music, the video or music being played in the game) by processing the data of the replay content constituting the distribution content.

(System Configuration)

Figure 35:
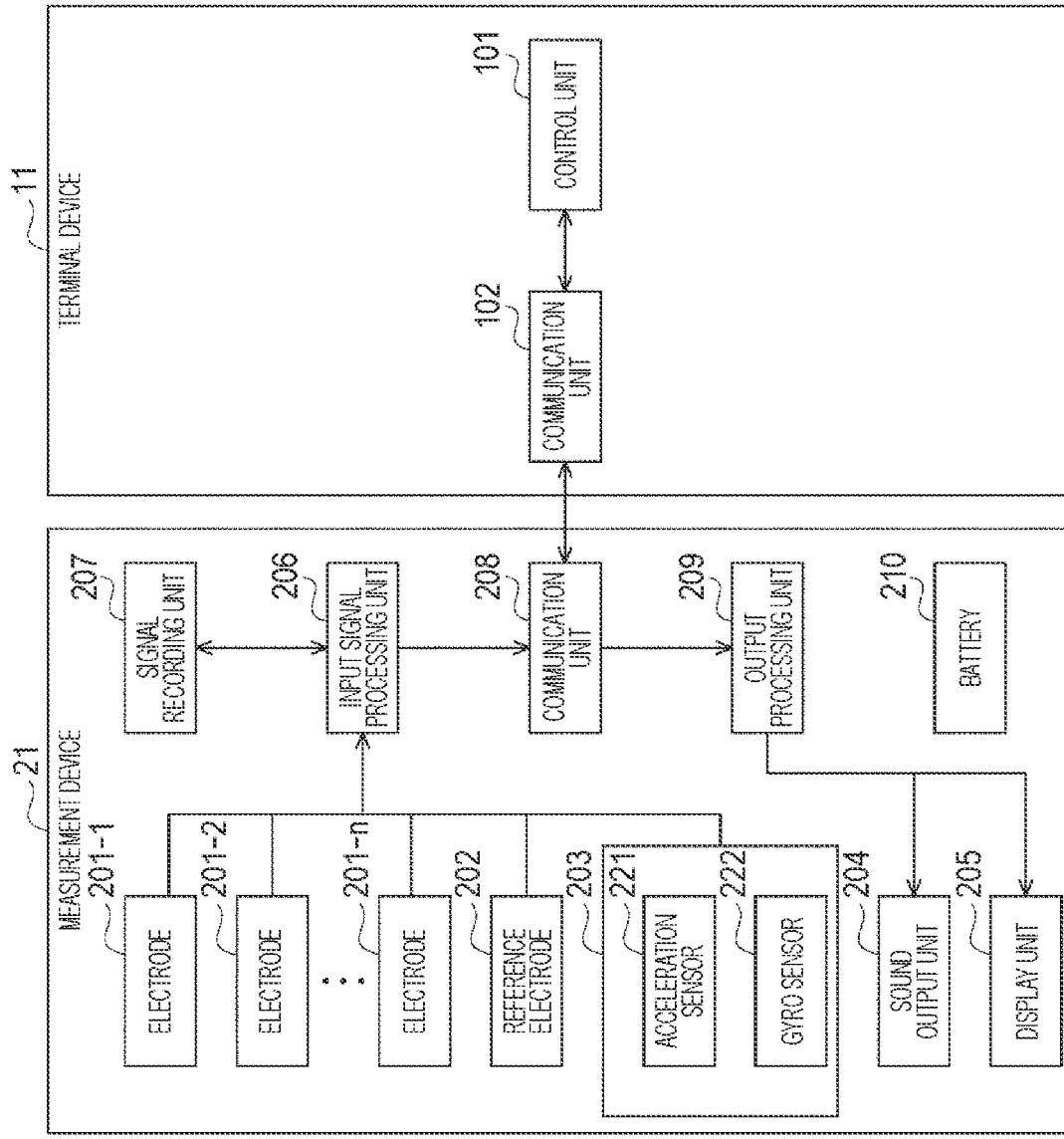
FIG. 35 is a block diagram illustrating a configuration example of a brain information system to which the present technology is applied.

FIG. 35 illustrates a configuration example of a brain information system to which the present technology is applied.

The brain information system is a system capable of providing various services using a brain wave signal measured from the head of the user. In FIG. 35, the brain information system includes the terminal device 11 and a measurement device 21. The same reference numerals are given to portions corresponding to those of the configuration example in FIG. 13, and the description thereof will be appropriately omitted.

The terminal device 11 is an electronic apparatus such as the above-described mobile terminal 11A such as a smartphone or a mobile music player. As in the terminal device 10 in FIG. 13, the terminal device 11 includes the control unit 101 and the communication unit 102.

The measurement device 21 is an electronic apparatus such as the earphone 21A and the HMD 21B described above. As in the measurement device 20 of FIG. 13, the measurement device 21 includes the electrodes 201-1 to 201-n, the reference electrode 202, the sensor unit 203, the sound output unit 204, the display unit 205, the input signal processing unit 206, the signal recording unit 207, the communication unit 208, the output processing unit 209, and the battery 210.

The input signal processing unit 206 processes the biometric signals from the electrodes 201-1 to 201-n and the reference electrode 202, reads the brain wave signal, and performs a predetermined signal process.

Another Configuration Example

Figure 36:
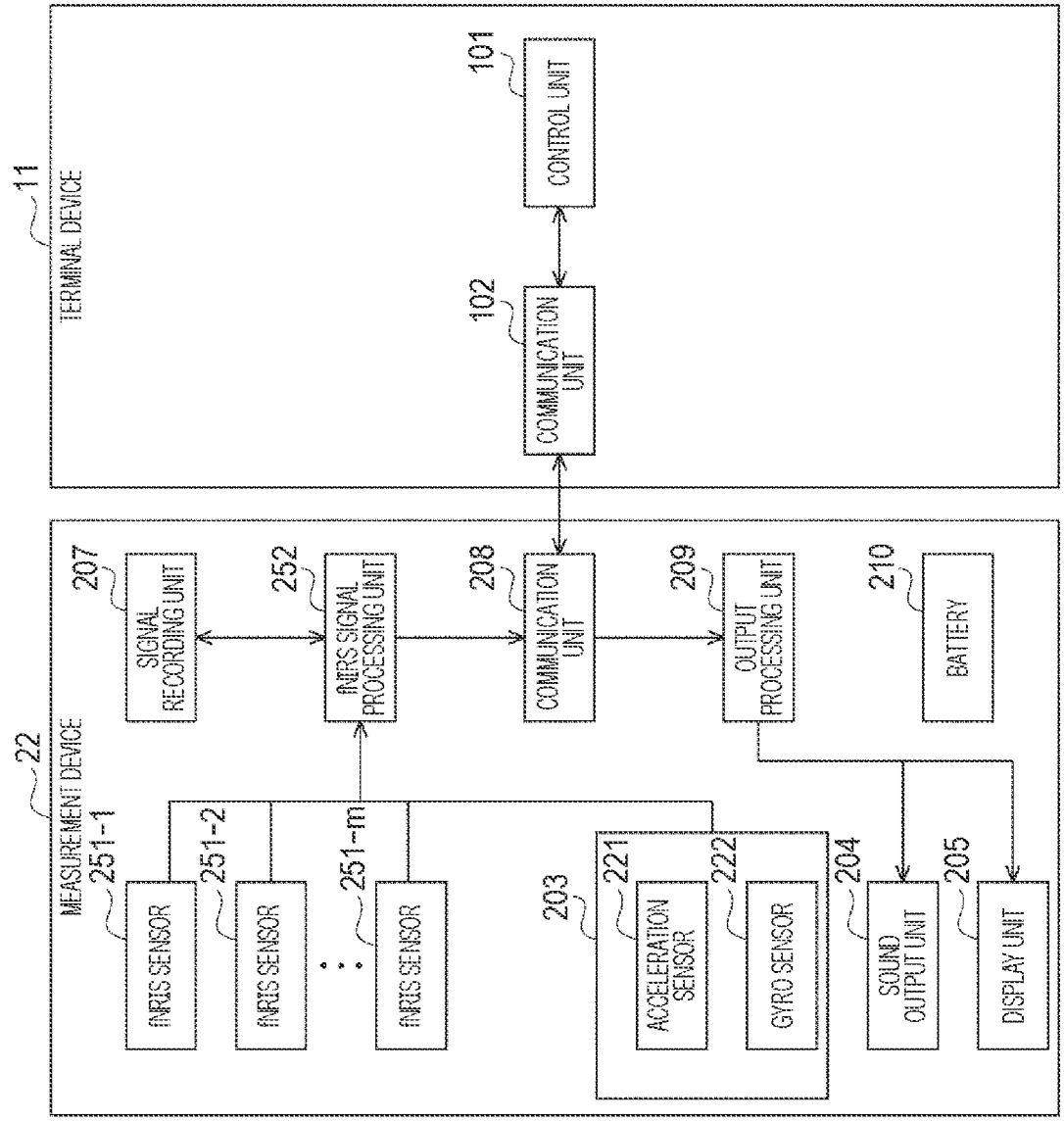
FIG. 36 is a block diagram illustrating another configuration example of a brain information system to which the present technology is applied.

FIG. 36 illustrates another configuration example of the brain information system to which the present technology is applied.

In FIG. 36, the authentication system includes the terminal device 11 and a measurement device 22. The same components as those in the configuration example in FIG. 35 are denoted by the same reference numerals, and the description thereof will be omitted because it is repeated.

In FIG. 36, the measurement device 22 is an electronic apparatus such as an earphone or an HMD. The measurement device 22 is different from the measurement device 21 of FIG. 35 in that instead of the electrodes 201-1 to 201-n, the reference electrode 202, and the input signal processing unit 206, fNIRS sensors 251-1 to 251-m (m: an integer of one or more) and an fNIRS signal processing unit 252 are included.

The fNIRS sensors 251-1 to 251-m are attached to parts such as the user's head and ear. The measured fNIRS signals of the fNIRS sensors 251-1 to 251-m are supplied to the fNIRS signal processing unit 252. The fNIRS signal processing unit 252 performs a predetermined signal process on the fNIRS signals from the fNIRS sensors 251-1 to 251-m.

Figure 37:
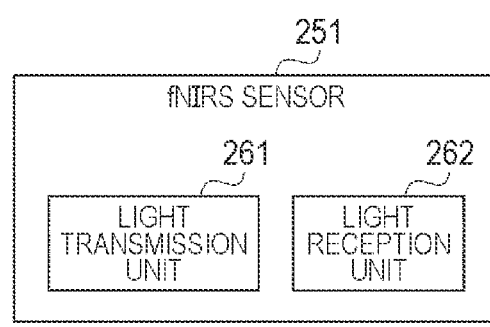
FIG. 37 is a block diagram illustrating a configuration example of an fNIRS sensor.

FIG. 37 illustrates a configuration example of the fNIRS sensor 251. In FIG. 37, the fNIRS sensor 251 includes a light transmission unit 261 and a light reception unit 262.

The light transmission unit 261 and the light reception unit 262 are attached so as to be in close contact with the scalp of the user, and the near-infrared light emitted by the light transmission unit 261 is transmitted through the skin tissue and received by the light reception unit 262. In this way, the fNIRS signal is measured by using a measurement method applying the principle of optical functional imaging in which the brain function is non-invasively mapped from the scalp using near-infrared light.

Arrangement Example of fNIRS Sensors

Figure 38:
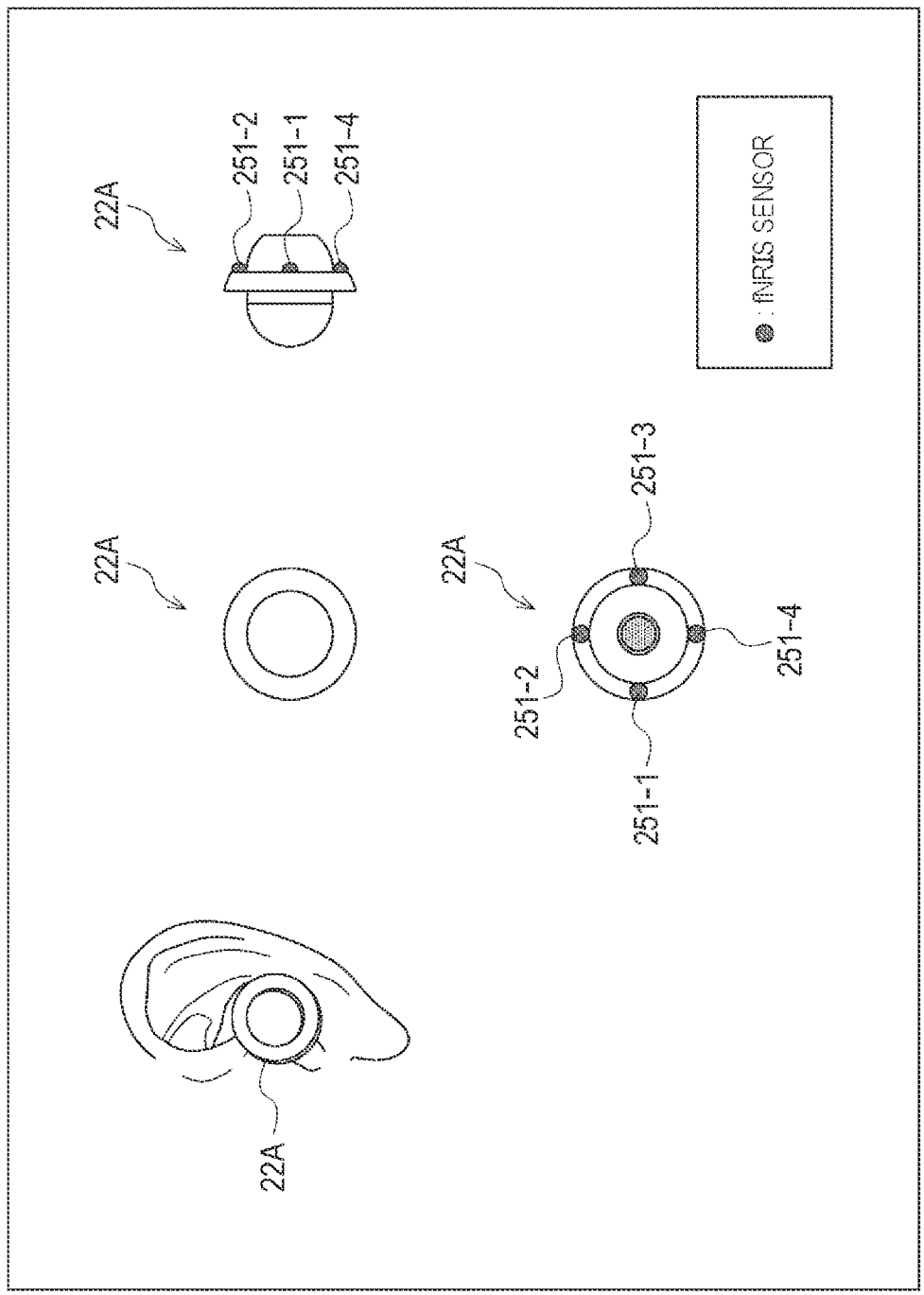
FIG. 38 is a diagram illustrating an arrangement example of fNIRS sensors provided in an earphone.

FIG. 38 illustrates an arrangement example of the fNIRS sensor 251 provided in an earphone 22A.

As illustrated in FIG. 38, four fNIRS sensors 251-1 to 251-4 are disposed at substantially equal intervals on the same circumference around the portion that outputs a sound on the face in contact with the ear of the user, and the fNIRS signal can be measured.

Figure 39:
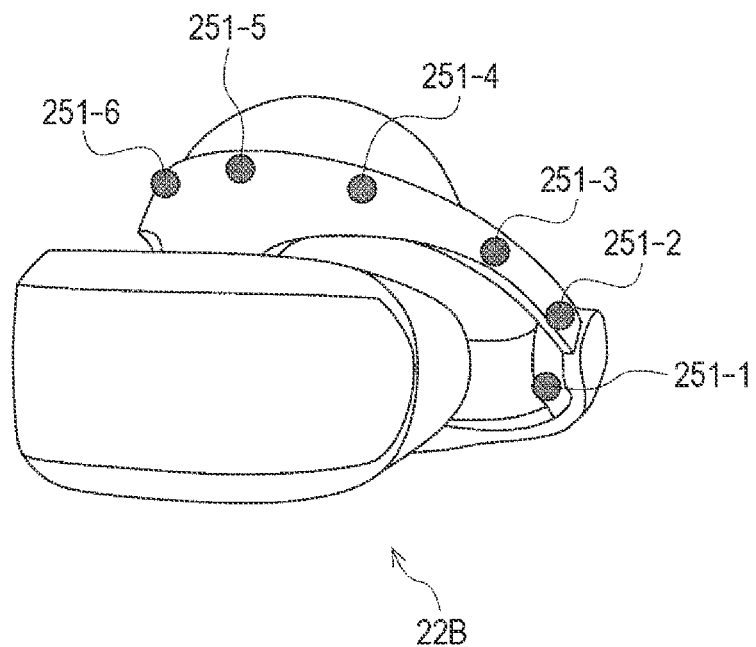
FIG. 39 is a diagram illustrating an arrangement example of fNIRS sensors provided in an HMD.

FIG. 39 illustrates an arrangement example of the fNIRS sensor 251 provided in the HMD 22B.

As illustrated in FIG. 39, in the HMD 22B, eight fNIRS sensors 251-2 to 251-9 are disposed in a straight line at substantially equal intervals on the face in contact with the forehead of the user, and the fNIRS sensor 251-1 is disposed, away from the eight sensors, at a predetermined position on the face in contact with the back of the head, and the fNIRS signal can be measured.

Note that, in the perspective view of FIG. 15, among the fNIRS sensor 251-1 to 251-9, the three fNIRS sensors 251-7 to 251-9 are not illustrated because they are in blind spots. In addition, for convenience of explanation, the fNIRS sensor 251 is illustrated to appear in the appearance of the HMD 22B, but is actually provided on the face in contact with the forehead of the user, that is, at a position not visible in the perspective view of FIG. 39.

Configuration Example of Table

Figure 40:
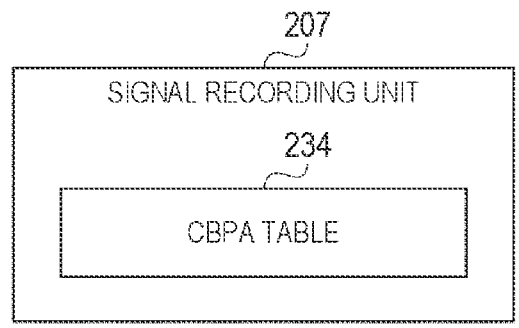
FIG. 40 is a diagram illustrating a configuration example of a table recorded in a signal recording unit.

FIG. 40 illustrates a configuration example of a table recorded in the signal recording unit 207 of FIG. 35 or 36.

The signal recording unit 207 records a CBPA table 234. The CBPA table 234 is a table in which registration information including induction media such as an induction sound and an induction video and data such as brain information such as brain wave information (brain wave signal) and cerebral blood flow information (fNIRS signal and the like) is recorded in time series. Continuous brainwave personal authentication (CBPA) means electroencephalogram personal authentication that enhances security while changing the induction medium by continuous use.

As illustrated in FIG. 41, in the CBPA table 234, registration information including the induction sound #1 and the brain wave signal #31, registration information including the induction sound #2 and the brain wave signal #32, registration information including the induction sound #3 and the brain wave signal #33, registration information including the induction sound #4 and the brain wave signal #34, registration information including the induction sound #5 and the brain wave signal #35, registration information including the induction sound #6 and the brain wave signal #36, and the like are recorded in time series. In the authentication process, the induction sound registered last time and the response brain wave signal thereof are read from the CBPA table 234, and authentication is performed. In the registration process, a newly generated induction sound and a response brain wave signal thereof are newly registered in the CBPA table 234.

Note that, although not illustrated because the description is repeated, as in the electroencephalogram system illustrated in FIGS. 20 to 22 described above, the brain information system illustrated in FIG. 35 or 36 may adopt various configurations such as a configuration in which the server 30 is provided and a configuration in which the terminal device 10 is omitted.

(Flow of Processing)

Next, the authentication registration process of electroencephalogram personal authentication will be described with reference to the flowcharts of FIGS. 42 and 43.

In this authentication registration process, after receiving a command to start the authentication process from the CBPA implementation application executed by the terminal device 11 or the measurement device 21 ("Yes" in S311), the process proceeds to step S312.

In step S312, the input signal processing unit 206 refers to the CBPA table 234 of the signal recording unit 207 to determine whether there is a registered brain wave signal for personal authentication of the CBPA implementation application.

In the determination process of step S312, when it is recognized that there is no registered brain wave signal, that is, it is the first time due to the first confirmation, the process proceeds to step S313. In step S313, the output processing unit 209 reproduces the new registration induction medium to output the medium from the sound output unit 204 or the display unit 205.

In step S314, the input signal processing unit 206 processes the biometric signal from the electrode 201 and the reference electrode 202, and determines whether the brain wave signal according to the response by the induction medium has been read.

In a case where it is determined in the determination process of step S314 that the response brain wave signal has not been read, the process proceeds to step S315. In step S315, notification of an error is provided to the CBPA implementation application executed by the terminal device 11 or the measurement device 21.

Note that, in a case where retry is defined by the CBPA implementation application, the process returns to step S313, and the subsequent processes are repeated, and reading of the response brain wave signal according to the new registration induction medium is retried.

On the other hand, in a case where it is determined in the determination process of step S314 that the response brain wave signal has been read, the process proceeds to step S316. In step S316, the input signal processing unit 206 records information regarding the induction medium, the response brain wave signal, and the time in the CBPA table 234 of the signal recording unit 207.

When the process of step S316 is completed, the process proceeds to step S317. In addition, in a case where it is determined in the determination process of step S312 that there is the registered brain wave signal, the process proceeds to step S317.

In step S317, the output processing unit 209 reproduces the induction medium registered last time to output the medium from the sound output unit 204 or the display unit 205.

In step S318, the input signal processing unit 206 processes the biometric signal from the electrode 201 and the reference electrode 202, and determines whether the brain wave signal according to the response by the induction medium has been read.

In a case where it is determined in the determination process of step S318 that the response brain wave signal has not been read, the process proceeds to step S319. In step S319, notification of an error is provided to the CBPA implementation application executed by the terminal device 11 or the measurement device 21.

Note that, in a case where retry is defined by the CBPA implementation application, the process returns to step S317, and the subsequent processes are repeated, and reading of the response brain wave signal according to the induction medium registered last time is retried.

Figure 42:
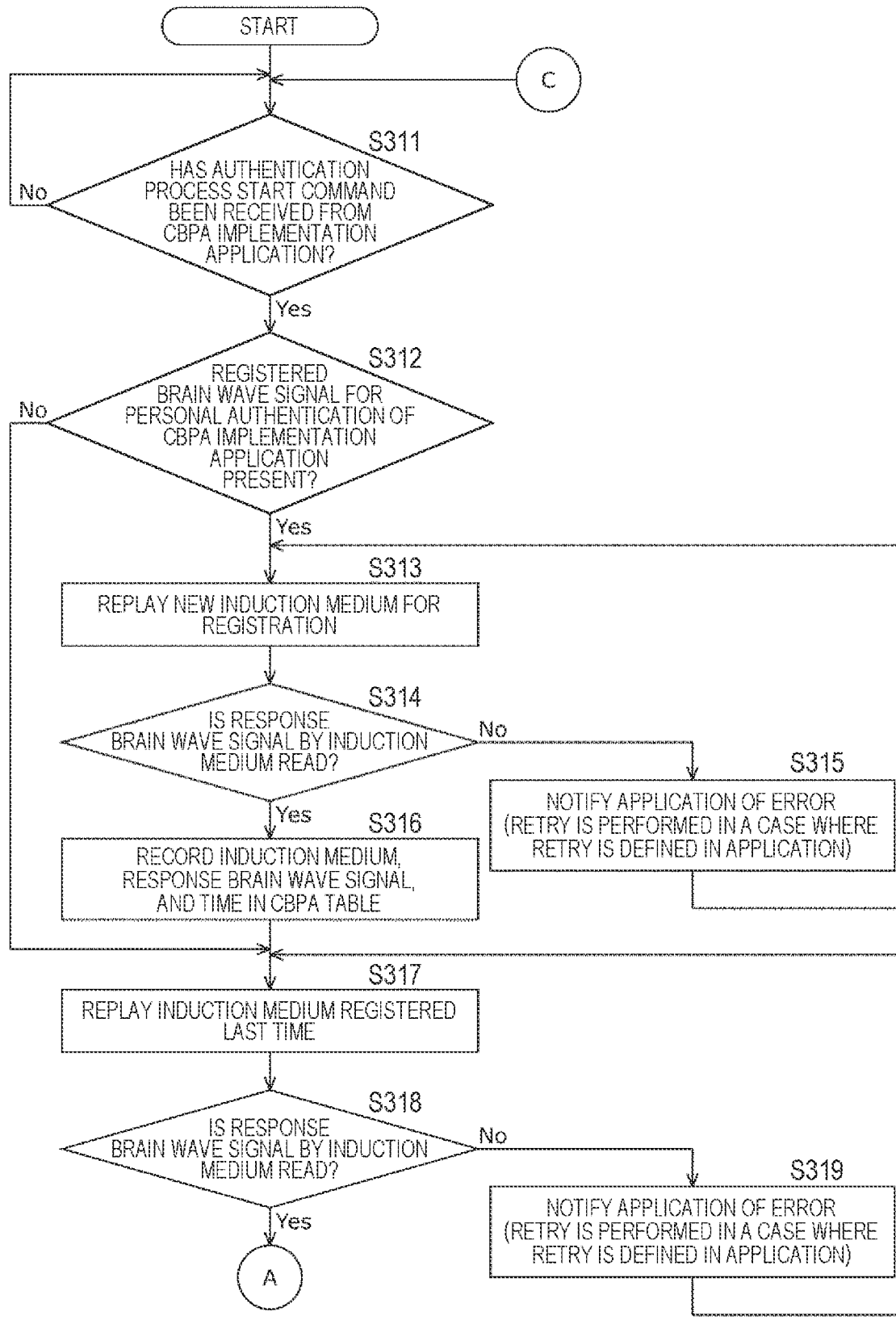
FIG. 42 is a flowchart illustrating a flow of an authentication registration process.
Figure 43:
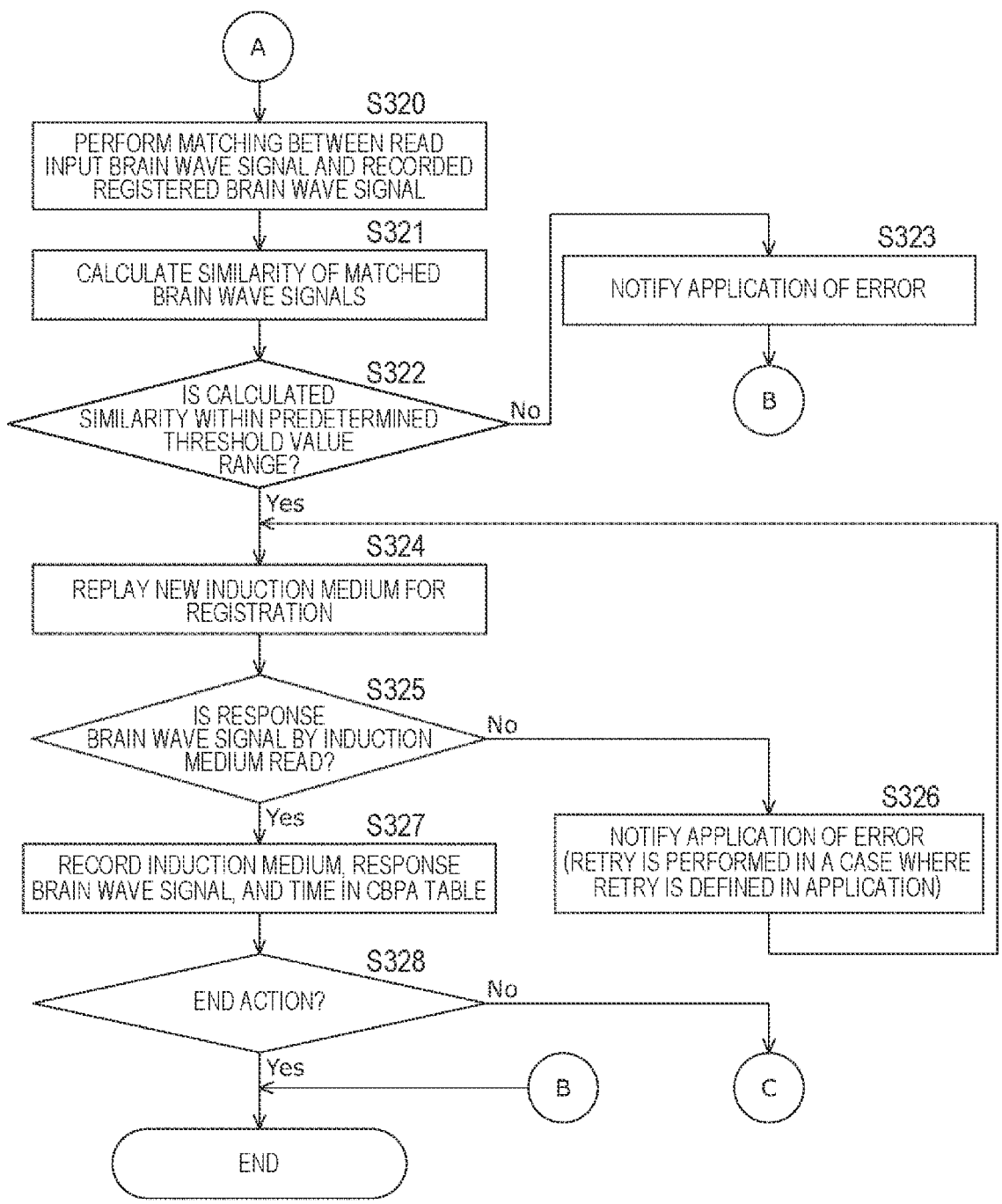
FIG. 43 is a flowchart illustrating a flow of an authentication registration process.

On the other hand, in a case where it is determined in the determination process of step S318 that the response brain wave signal has been read, the process proceeds to step S320 of FIG. 42.

In step S320, the input signal processing unit 206 performs matching between the input brain wave signal read by the process in step S318 and the registered brain wave signal recorded in the CBPA table 234 of the signal recording unit 207. In addition, in step S321, the input signal processing unit 206 calculates the similarity between the matched brain wave signals.

In step S322, the input signal processing unit 206 determines whether the calculated similarity is within a predetermined threshold value range.

In a case where it is determined in the determination process of step S322 that the similarity is out of the range of the predetermined threshold value, the process proceeds to step S323. In step S323, notification of an error is provided to the CBPA implementation application executed by the terminal device 11 or the measurement device 21, and the authentication registration process ends.

In addition, in a case where it is determined in the determination process of step S322 that the similarity falls within the range of the predetermined threshold value, the process proceeds to step S324. In step S324, the output processing unit 209 reproduces the new registration induction medium to output the medium from the sound output unit 204 or the display unit 205.

In step S325, the input signal processing unit 206 processes the biometric signal from the electrode 201 and the reference electrode 202, and determines whether the brain wave signal according to the response by the induction medium has been read.

In a case where it is determined in the determination process of step S325 that the response brain wave signal has not been read, the process proceeds to step S326. In step S326, an error is notified to the CBPA implementation application executed by the terminal device 11 or the measurement device 21.

Note that, in a case where retry is defined by the CBPA implementation application, the process returns to step S324, and the subsequent processes are repeated, and reading of the response brain wave signal according to the new registration induction medium is retried.

On the other hand, in a case where it is determined in the determination process of step S325 that the response brain wave signal has been read, the process proceeds to step S327. In step S327, the input signal processing unit 206 records information regarding the induction medium, the response brain wave signal, and the time in the CBPA table 234 of the signal recording unit 207.

When the process of step S327 is completed, the process proceeds to step S328. In step S328, it is determined whether to end the action, and in a case where it is determined that the action is not to be ended, the process returns to step S311 in FIG. 42, and the subsequent processes are repeated. In addition, in a case where it is determined that the action is to be ended, the authentication registration process ends.

As described above, the measurement device 21 or the measurement device 22 is continuously used to repeat authentication and registration using brain information such as a brain wave signal or an fNIRS signal according to a response of the user to the replayed induction medium while changing the induction medium such as auditory induction or visual induction, thereby enhancing security.

That is, in the present technology, control of a first authentication process of authenticating a user on the basis of first registration information based on first brain information about the user measured in response to a replay of a first induction medium, and control of a registration process of a second registration information used for a second authentication process of authenticating the user on the basis of second brain information about the user measured in response to a replay of a second induction medium are performed. Therefore, since the authentication process and the registration process are repeated while changing the induction medium, it is possible to suppress the possibility that the induction medium or the brain information leaks to the outside due to hacking or the like, and perform authentication with higher safety using the brain information.

Note that, in the above description, the induction sound as the auditory induction and the induction video as the visual induction have been exemplified as the induction medium, but an induction vibration as the tactile induction, the olfactory induction, or the like may be used. In addition, in each authentication, a replay is performed with a combination of the first induction medium and the second induction medium, and a combination of the first induction medium and the second induction medium replayed in each authentication is different. For example, the replay order of the first induction medium (for authentication) and the second induction medium (for registration) is not limited to the order of the first induction medium and the second induction medium, and may be the order of the second induction medium and the first induction medium, or the order may be changed each time in other than continuing a certain order.

3. Configuration of Computer

A series of processes of the terminal device 10, the measurement device 20, and the server 30 described above can be executed by hardware or software. In a case where the series of processes is executed by software, a program constituting the software is installed in a computer of each device.

Figure 44:
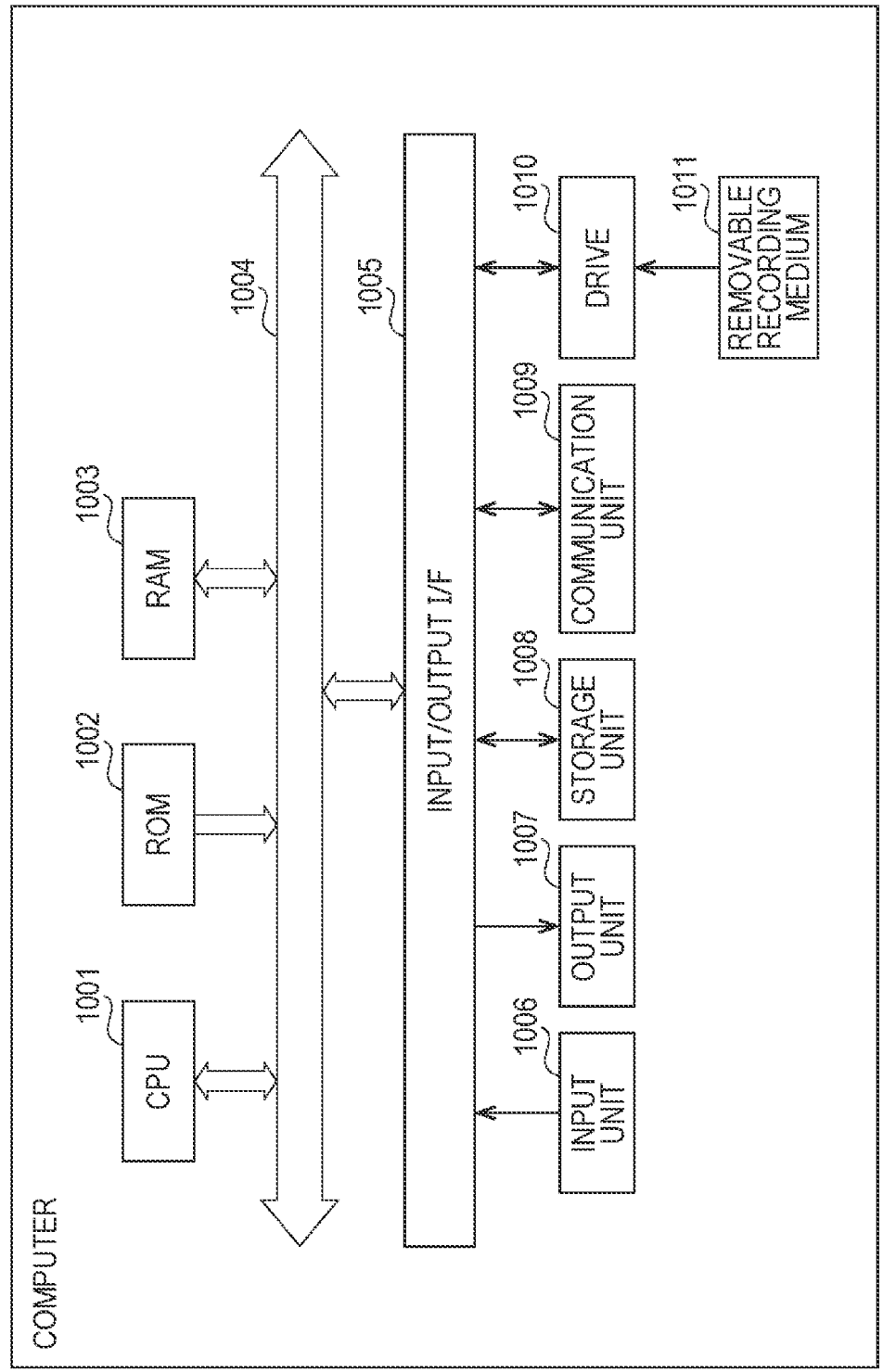
FIG. 44 is a block diagram illustrating a configuration example of a computer.

FIG. 44 is a block diagram illustrating a configuration example of hardware of a computer that executes the above-described series of processes by a program.

In a computer, a central processing unit (CPU) 1001, a read only memory (ROM) 1002, and a random access memory (RAM) 1003 are mutually connected by a bus 1004. An input/output interface 1005 is further connected to the bus 1004. An input unit 1006, an output unit 1007, a storage unit 1008, a communication unit 1009, and a drive 1010 are connected to the input/output interface 1005.

The input unit 1006 includes a microphone, a keyboard, a mouse, and the like. The output unit 1007 includes a speaker, a display, and the like. The storage unit 1008 includes a hard disk, a nonvolatile memory, and the like. The communication unit 1009 includes a network interface and the like. The drive 1010 drives a removable recording medium 1011 such as a magnetic disk, an optical disk, a magneto-optical disk, or a semiconductor memory.

In the computer configured as described above, the CPU 1001 loads a program recorded in the ROM 1002 or the storage unit 1008 into the RAM 1003 via the input/output interface 1005 and the bus 1004 and executes the program, whereby the above-described series of processes is performed.

The program executed by the computer (CPU 1001) can be provided by being recorded in the removable recording medium 1011 as a package medium or the like, for example. In addition, the program can be provided via a wired or wireless transmission medium such as a local area network, the Internet, or digital satellite broadcasting.

In the computer, the program can be installed in the storage unit 1008 via the input/output interface 1005 by attaching the removable recording medium 1011 to the drive 1010. In addition, the program can be received by the communication unit 1009 via a wired or wireless transmission medium and installed in the storage unit 1008. In addition, the program can be installed in the ROM 1002 or the storage unit 1008 in advance.

Here, in the present specification, the processing performed by the computer according to the program is not necessarily performed in time series in the order described as the flowchart. That is, the processing performed by the computer according to the program also includes processing executed in parallel or individually (for example, parallel processing or processing by an object).

In addition, the program may be processed by one computer (processor) or may be processed in a distributed manner by a plurality of computers. Further, the program may be transferred to a remote computer and executed.

Furthermore, in the present specification, a system means a set of a plurality of components (devices, modules (parts), etc.), and it does not matter whether or not all the components are in the same housing. Therefore, a plurality of devices housed in separate housings and connected via a network and one device in which a plurality of modules is housed in one housing are both systems.

Note that the embodiments of the present technology are not limited to the above-described embodiments, and various modifications can be made without departing from the gist of the present technology. For example, the present technology can have a configuration of cloud computing in which one function is shared and processed in cooperation by a plurality of devices via a network.

In addition, each step described in the above-described flowchart can be executed by one device or can be shared and executed by a plurality of devices. Furthermore, in a case where a plurality of processes is included in one step, the plurality of processes included in the one step can be executed by one device or can be shared and executed by a plurality of devices.

In addition, the effects described in the present specification are merely examples and are not limited, and other effects may be provided.

Note that the present technology can have the following configurations.

(1)

A control device including a detection unit configured to perform detection of a brain wave included in a measured biometric signal of a user and detection of a user action based on information other than the brain wave included in the biometric signal, and a processing unit configured to perform a predetermined process based on the brain wave in a case where the user action is a predetermined action.

(2)

The control device according to the item (1), in which the information other than the brain wave includes a myoelectric signal, and the detection unit detects the user action on the basis of the myoelectric signal measured from the user.

(3)

The control device according to the item (2), in which the predetermined action is a trigger action set according to an application using a brain wave.

(4)

The control device according to the item (3), in which in a case where a trigger action is detected as the user action, the processing unit performs a matching process between a first brain wave signal measured from the user and a second brain wave signal measured from the user at timing different from timing of the first brain wave signal.

(5)

The control device according to the item (2), in which the predetermined action is a trigger action set for each application using a brain wave.

(6)

The control device according to the item (2) or (5), in which the application is a personal authentication application using a brain wave, and in a case where a trigger action is detected as the user action, the processing unit performs a matching process between a first brain wave signal measured from the user and a second brain wave signal measured from the user at timing different from timing of the first brain wave signal.

(7)

The control device according to any one of the items (4) to (6), in which the first brain wave signal and the second brain wave signal are measured according to an instruction.

(8)

The control device according to any one of (4) to (6), in which the first brain wave signal and the second brain wave signal are event-related potentials.

(9)

The control device according to the item (2) or (5), in which the application is a search application using a brain wave, and a first brain wave signal measured from the user and a second brain wave signal measured from the user at timing different from timing of the first brain wave signal each include a brain wave signal regarding a thought of the user with respect to a same object.

(10)

The control device according to the item (9), in which the object includes information allowed to be presented to a terminal device used by the user, and provided by a specific medium.

(11)

The control device according to any one of the items (3) to (10), in which the processing unit performs a matching process between a first myoelectric signal measured from the user and a second myoelectric signal measured from the user at timing different from timing of the first myoelectric signal, and determines whether a trigger action is detected on the basis of a result of the matching process.

(12)

The control device according to the item (11), in which the first myoelectric signal is measured and registered in advance for each application, and the second myoelectric signal is measured at any timing when an application is activated.

(13)

The control device according to any one of the items (3) to (12), in which the trigger action includes a movement of each part of a head of the user or a combination of the movement of the each part and a movement of the head.

(14)

The control device according to the item (13), in which the trigger action is detected by a signal from an electrode provided to contact a head of the user or a signal from a sensor unit.

(15)

The control device according to the item (4), in which the brain wave signal and the myoelectric signal are each measured by a signal from an electrode provided to contact a head of the user.

(16)

The control device according to any one of the items (2) to (15), in which the control device has a first mode in which a myoelectric signal is measured and a second mode in which a brain wave signal is measured, and sets a time resolution and an amplification factor of a signal amplifier at a time of reading a signal in the first mode to be lower than a time resolution and an amplification factor at a time of reading a signal in the second mode.

(17)

The control device according to any one of the items (2) to (16), in which the control device is configured as a measurement device that measures a brain wave signal and a myoelectric signal, a terminal device connected to the measurement device in a wired or wireless manner, or a server connected to the measurement device via a network.

(18)
A control method including
a control device
detecting a brain wave included in a measured biometric signal of a user and detecting a user action based on information other than the brain wave included in the biometric signal, and
performing a predetermined process based on the brain wave in a case where the user action is a predetermined action.

REFERENCE SIGNS LIST 10, 11 Terminal device
10A, 11A Mobile terminal
20, 21, 22 Measurement device
20A, 21A Earphone
20B, 21B HMD
30 Server
40 Network
101 Control unit
102 Communication unit
103 Input signal processing unit
104 Signal recording unit
105 Output processing unit
106 Sound output unit
107 Display unit
201, 201-1 to 201-n Electrode
202 Reference electrode
203 Sensor unit
204 Sound output unit
205 Display unit
206 Input signal processing unit
207 Signal recording unit
208 Communication unit
209 Output processing unit
210 Battery
211 Control unit
221 Acceleration sensor
222 Gyro sensor
231 Trigger action signal recording table
232 Trigger action-specific electroencephalogram application table
233 Brain wave signal recording table
234 CBPA table
251, 251-1 to 251-m fNIRS sensor
252 fNIRS signal processing unit
261 Light transmission unit
262 Light reception unit
301 Control unit
302 Communication unit
303 Input signal processing unit
304 Signal recording unit
305 Output processing unit
1001 CPU

The invention claimed is:
1. A control device, comprising:
a detection unit configured to:
perform detection of a brain wave included in a measured biometric signal of a user and detection of a user action based on information other than the brain wave included in the measured biometric signal, wherein the information other than the brain wave includes a myoelectric signal;
detect the user action based on the myoelectric signal measured from the user; and
a processing unit configured to perform a predetermined process based on the brain wave in a case where the user action is a predetermined action, wherein
the control device has a first mode in which the myoelectric signal is measured and a second mode in which a brain wave signal is measured, and
the control device is configured to set a time resolution and an amplification factor of a signal amplifier at a time of reading a signal in the first mode to be lower than a time resolution and an amplification factor of the signal amplifier at a time of reading a signal in the second mode.
2. The control device according to claim 1, wherein the predetermined action is a trigger action set according to an application using the brain wave.
3. The control device according to claim 2, wherein in a case where the trigger action is detected as the user action, the processing unit is configured to perform a matching process between a first brain wave signal measured from the user and a second brain wave signal measured from the user at timing different from timing of the first brain wave signal.
4. The control device according to claim 1, wherein the predetermined action is a trigger action set for an application using the brain wave.
5. The control device according to claim 4, wherein the application is a personal authentication application using the brain wave, and
in a case where the trigger action is detected as the user action, the processing unit is further configured to perform a matching process between a first brain wave signal measured from the user and a second brain wave signal measured from the user at timing different from timing of the first brain wave signal.
6. The control device according to claim 5, wherein the first brain wave signal and the second brain wave signal are measured according to an instruction.
7. The control device according to claim 5, wherein the first brain wave signal and the second brain wave signal are event-related potentials.
8. The control device according to claim 4, wherein the application is a search application using the brain wave, and
each of a first brain wave signal measured from the user and a second brain wave signal, measured from the user at timing different from timing of the first brain wave signal, include the brain wave signal regarding a thought of the user with respect to an object.
9. The control device according to claim 8, wherein the object includes information allowed to be presented to a terminal device used by the user, and provided by a specific medium.
10. The control device according to claim 2, wherein the processing unit is further configured to:
perform a matching process between a first myoelectric signal measured from the user and a second myoelectric signal measured from the user at timing different from timing of the first myoelectric signal, and
determine whether the trigger action is detected based on a result of the matching process.
11. The control device according to claim 10, wherein the first myoelectric signal is measured and registered in advance for each application, and
the second myoelectric signal is measured at any timing when an application is activated.

12. The control device according to claim 2, wherein
the trigger action includes a movement of each part of a head of the user or a combination of the movement of each part of the head and a movement of the head.

13. The control device according to claim 12, wherein
the trigger action is detected by a signal from an electrode provided to contact the head of the user or a signal from a sensor unit.

14. The control device according to claim 1, wherein
the brain wave signal and the myoelectric signal are each measured by a signal from an electrode provided to contact a head of the user.

15. The control device according to claim 1, wherein
the control device is configured as a measurement device that measures the brain wave signal and the myoelectric signal, a terminal device connected to the measurement device in a wired or wireless manner, or a server connected to the measurement device via a network.

16. A control method, comprising:
a control device:
  detecting a brain wave included in a measured biometric signal of a user and a user action, based on information other than the brain wave included in the measured biometric signal, wherein the information other than the brain wave includes a myoelectric signal;
  detecting the user action based on the myoelectric signal measured from the user;
  performing a predetermined process based on the brain wave in a case where the user action is a predetermined action; and
  setting a time resolution and an amplification factor of a signal amplifier at a time of reading a signal in a first mode to be lower than a time resolution and an amplification factor of the signal amplifier at a time of reading a signal in a second mode, wherein
  the myoelectric signal is measured the first mode and a brain wave signal is measured in the second mode.

17. A control device, comprising:
a detection unit configured to:
  perform detection of a brain wave included in a measured biometric signal of a user and detection of a user action based on information other than the brain wave included in the measured biometric signal, wherein the information other than the brain wave includes a myoelectric signal; and
  detect the user action based on the myoelectric signal measured from the user; and
a processing unit configured to:
  perform a predetermined process based on the brain wave in a case where the user action is a predetermined action, wherein the predetermined action is a trigger action set according to an application using the brain wave;
  perform a matching process between a first myoelectric signal measured from the user and a second myoelectric signal measured from the user at timing different from timing of the first myoelectric signal; and
  determine whether the trigger action is detected based on a result of the matching process.

* * * * *